United States Patent
Cohen et al.

(10) Patent No.: US 9,763,993 B2
(45) Date of Patent: *Sep. 19, 2017

(54) PROCESS FOR MANUFACTURING GLATIRAMER ACETATE PRODUCT

(71) Applicant: Teva Pharmaceutical Industries, Ltd., Petach-Tikva (IL)

(72) Inventors: Rakefet Cohen, Kokhav Ya'ir-Tzur Yigal (IL); Sasson Habbah, Kokhav Ya'ir-Tzur Yigal (IL); Muhammad Safadi, Nazareth (IL)

(73) Assignee: TEVA PHARMACEUTICAL INDUSTRIES LTD., Petach Tikva (IL)

(*) Notice: Subject to any disclaimer, the term of this patent is extended or adjusted under 35 U.S.C. 154(b) by 0 days.

This patent is subject to a terminal disclaimer.

(21) Appl. No.: 14/860,053

(22) Filed: Sep. 21, 2015

(65) Prior Publication Data

US 2016/0213734 A1  Jul. 28, 2016

Related U.S. Application Data

(63) Continuation of application No. 14/608,126, filed on Jan. 28, 2015, now Pat. No. 9,155,775.

(51) Int. Cl.
| | |
|---|---|
| *A61K 38/16* | (2006.01) |
| *A61K 9/00* | (2006.01) |
| *A61K 47/26* | (2006.01) |
| *A61K 9/08* | (2006.01) |
| *A61K 38/02* | (2006.01) |

(52) U.S. Cl.
CPC ............ *A61K 38/02* (2013.01); *A61K 9/0019* (2013.01); *A61K 9/08* (2013.01); *A61K 38/16* (2013.01); *A61K 47/26* (2013.01)

(58) Field of Classification Search
CPC ........ A61K 38/02; A61K 9/0019; A61K 9/08; A61K 47/26
See application file for complete search history.

(56) References Cited

U.S. PATENT DOCUMENTS

| | | | |
|---|---|---|---|
| 3,849,550 A | 11/1974 | Teitelbaum et al. | |
| 4,350,156 A | 9/1982 | Malchesky et al. | |
| 4,455,256 A | 6/1984 | Urist | |
| 4,711,953 A | 12/1987 | Roger et al. | |
| 5,631,347 A | 5/1997 | Baker et al. | |
| 5,800,808 A | 9/1998 | Konfino et al. | |
| 5,981,589 A | 11/1999 | Konfino et al. | |
| 6,048,898 A | 4/2000 | Konfino et al. | |
| 6,054,430 A | 4/2000 | Konfino et al. | |
| 6,103,502 A | 8/2000 | Moller et al. | |
| 6,214,791 B1 | 4/2001 | Arnon et al. | |
| 6,342,476 B1 | 1/2002 | Konfino et al. | |
| 6,362,161 B1 | 3/2002 | Konfino et al. | |
| 6,514,938 B1 | 2/2003 | Gad et al. | |
| 6,620,847 B2 | 9/2003 | Konfino et al. | |
| 6,800,285 B2 | 10/2004 | Rodriguez et al. | |
| 6,800,287 B2 | 10/2004 | Gad et al. | |
| 6,939,539 B2 | 9/2005 | Konfino et al. | |
| 7,022,663 B2 | 4/2006 | Gilbert et al. | |
| 7,033,582 B2 | 4/2006 | Yong et al. | |
| 7,049,399 B2 | 5/2006 | Bejan et al. | |
| 7,074,580 B2 | 7/2006 | Gad et al. | |
| 7,163,802 B2 | 1/2007 | Gad et al. | |
| 7,199,098 B2 | 4/2007 | Konfino et al. | |
| 7,279,172 B2 | 10/2007 | Aharoni et al. | |
| 7,425,332 B2 | 9/2008 | Sela et al. | |
| 7,429,374 B2 | 9/2008 | Klinger | |
| 7,495,072 B2 | 2/2009 | Dolitzky | |
| 7,560,100 B2 | 7/2009 | Pinchasi et al. | |
| 7,566,767 B2 | 7/2009 | Strominger et al. | |

(Continued)

FOREIGN PATENT DOCUMENTS

| | | |
|---|---|---|
| CN | 100569282 C | 12/2009 |
| EP | 2334394 | 9/2013 |

(Continued)

OTHER PUBLICATIONS

Djukic et al., Eur J Paediatric Neurology 19S: S8 (OP23-2759) (2015).*

Nov. 20, 2015 Yeda's Patent Owner Response filed in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).

Nov. 20, 2015 Yeda's Patent Owner Response filed in connection with *Mylan Pharmaceuticals Inc.* v. *Yeda Research & Development Co. Ltd.* for U.S. Pat. No. 8,399,413 in the United States Patent and Trademark Office Patent Trial and Appeal Board (Case No. IPR2015-00644).

(Continued)

*Primary Examiner* — Sue Liu
*Assistant Examiner* — Thor Nielsen
(74) *Attorney, Agent, or Firm* — John P. White; Gary J. Gershik; Cooper & Dunham LLP

(57) ABSTRACT

The patent provides a process of preparing a pharmaceutical preparation of glatiramer acetate and mannitol in a suitable container comprising the steps of:
 (i) obtaining an aqueous pharmaceutical solution of glatiramer acetate and mannitol;
 (ii) filtering the aqueous pharmaceutical solution at a temperature of from above 0° C. up to 17.5° C. to produce a filtrate; and
 (iii) filling the suitable container with the filtrate obtained after performing step (ii), so as to thereby prepare the pharmaceutical preparation of glatiramer acetate and mannitol in the suitable container.

This patent further provides an aqueous pharmaceutical solution comprising 40 mg/ml glatiramer acetate and 40 mg/ml mannitol, wherein the aqueous pharmaceutical solution
 a) has a viscosity in the range of 2.0-3.5 cPa; or
 b) has an osmolality in the range of 275-325 mosmol/Kg.
This patent also provides a prefilled syringe, an automated injector and a method of treatment of a human patient.

35 Claims, 11 Drawing Sheets

(56) References Cited

U.S. PATENT DOCUMENTS

| | | |
|---|---|---|
| 7,615,359 B2 | 11/2009 | Gad et al. |
| 7,625,861 B2 | 12/2009 | Konfino et al. |
| 7,855,176 B1 | 12/2010 | Altman et al. |
| 7,923,215 B2 | 4/2011 | Klinger |
| 7,968,511 B2 | 6/2011 | Vollmer et al. |
| 8,008,258 B2 | 8/2011 | Aharoni et al. |
| 8,075,919 B2 | 12/2011 | Brown et al. |
| 8,232,250 B2 | 7/2012 | Klinger |
| 8,367,605 B2 | 2/2013 | Konfino et al. |
| 8,389,228 B2 | 3/2013 | Klinger |
| 8,399,413 B2 | 3/2013 | Klinger |
| 8,536,305 B2 | 9/2013 | Ray et al. |
| 8,546,363 B2 | 10/2013 | Ye |
| 8,709,433 B2 | 4/2014 | Kasper |
| 8,729,229 B2 | 5/2014 | Ray et al. |
| 8,759,302 B2 | 6/2014 | Dhib-Jalbut |
| 8,815,511 B2 | 8/2014 | Tchelet et al. |
| 8,920,373 B2 | 12/2014 | Altman et al. |
| 8,969,302 B2 | 3/2015 | Klinger |
| 9,018,170 B2 | 4/2015 | Altman et al. |
| 9,063,153 B2 | 6/2015 | Kasper |
| 9,155,775 B1 | 10/2015 | Cohen et al. |
| 2002/0077278 A1 | 6/2002 | Yong et al. |
| 2004/0124143 A1 | 7/2004 | Kee et al. |
| 2005/0019322 A1 | 1/2005 | Rodriguez et al. |
| 2005/0143568 A1 | 6/2005 | Schwindt |
| 2005/0170004 A1 | 8/2005 | Rosenberger |
| 2006/0172942 A1 | 8/2006 | Dolitzky |
| 2006/0189527 A1 | 8/2006 | Rasmussen et al. |
| 2006/0194725 A1 | 8/2006 | Rasmussen et al. |
| 2006/0240463 A1 | 10/2006 | Lancet |
| 2006/0264354 A1 | 11/2006 | Aharoni et al. |
| 2007/0021324 A1 | 1/2007 | Dolitzky |
| 2007/0037740 A1 | 2/2007 | Pinchasi et al. |
| 2007/0054857 A1 | 3/2007 | Pinchasi et al. |
| 2007/0059798 A1 | 3/2007 | Gad |
| 2007/0161566 A1 | 7/2007 | Pinchasi |
| 2007/0244056 A1 | 10/2007 | Hayardeny et al. |
| 2008/0021192 A1 | 1/2008 | Iyer et al. |
| 2008/0118553 A1 | 5/2008 | Frenkel et al. |
| 2008/0207526 A1 | 8/2008 | Strominger |
| 2008/0261894 A1 | 10/2008 | Kreitman et al. |
| 2009/0048181 A1 | 2/2009 | Schipper et al. |
| 2009/0149541 A1 | 6/2009 | Stark et al. |
| 2010/0167983 A1 | 7/2010 | Kreitman et al. |
| 2010/0285600 A1 | 11/2010 | Lancet et al. |
| 2010/0298227 A1 | 11/2010 | Aharoni et al. |
| 2010/0305023 A1 | 12/2010 | Stark et al. |
| 2010/0324265 A1 | 12/2010 | Kota et al. |
| 2011/0060279 A1 | 3/2011 | Altman et al. |
| 2011/0066112 A1 | 3/2011 | Altman et al. |
| 2012/0027718 A1 | 2/2012 | Kreitman et al. |
| 2012/0309671 A1 | 12/2012 | Klinger |
| 2013/0165387 A1 | 6/2013 | Klinger |
| 2013/0323771 A1 | 12/2013 | Sathe et al. |
| 2014/0107208 A1 | 4/2014 | Comabella et al. |
| 2014/0193827 A1 | 7/2014 | Schwartz et al. |
| 2014/0271532 A1 | 9/2014 | Kreitman et al. |
| 2014/0271630 A1 | 9/2014 | Vollmer |
| 2014/0294899 A1 | 10/2014 | Kasper et al. |
| 2014/0322158 A1 | 10/2014 | Dhib-Jalbut |
| 2015/0045306 A1 | 2/2015 | Tchelet et al. |
| 2015/0110733 A1 | 4/2015 | Tchelet et al. |
| 2015/0164977 A1 | 6/2015 | Klinger |
| 2015/0202247 A1 | 7/2015 | Klinger |
| 2015/0241446 A1 | 8/2015 | Kasper et al. |
| 2015/0250845 A1 | 9/2015 | Klinger |

FOREIGN PATENT DOCUMENTS

| | | |
|---|---|---|
| WO | WO 98/30227 | 7/1998 |
| WO | WO 00/05250 | 2/2000 |
| WO | WO 00/05249 | 3/2000 |
| WO | WO 00/18794 | 4/2000 |
| WO | WO 00/20010 | 4/2000 |
| WO | WO 00/27417 | 5/2000 |
| WO | WO 01/60392 | 8/2001 |
| WO | WO 01/93828 | 12/2001 |
| WO | WO 01/97846 | 12/2001 |
| WO | WO 03/048735 | 6/2003 |
| WO | WO 2004/103297 | 2/2004 |
| WO | WO 2004/064717 | 8/2004 |
| WO | WO 2004/091573 | 10/2004 |
| WO | WO 2005/041933 | 5/2005 |
| WO | WO 2006/029036 | 3/2006 |
| WO | WO 2006/029393 | 3/2006 |
| WO | WO 2006/029411 | 3/2006 |
| WO | WO 2006/050122 | 5/2006 |
| WO | WO 2006/083608 | 8/2006 |
| WO | WO 2006/089164 | 8/2006 |
| WO | WO 2006/116602 | 11/2006 |
| WO | WO 2007/030573 | 3/2007 |
| WO | WO 2007/081975 | 7/2007 |
| WO | WO 2008/006026 | 1/2008 |
| WO | WO 2008/157697 | 12/2008 |
| WO | WO 2009/070298 | 6/2009 |
| WO | WO 2011/008274 | 1/2011 |
| WO | WO 2011/022063 | 2/2011 |
| WO | WO 2011/064114 | 6/2011 |
| WO | WO 2012/051106 | 4/2012 |
| WO | WO 2013/055683 | 4/2013 |
| WO | WO 2014/058976 | 4/2014 |
| WO | WO 2014/107533 | 7/2014 |
| WO | WO 2014/128079 | 8/2014 |
| WO | WO 2014/165280 | 10/2014 |
| WO | WO 2015/061367 | 4/2015 |

OTHER PUBLICATIONS

Nov. 25, 2015 Yeda's Patent Owner Response filed in connection with *Mylan Pharmaceuticals Inc.* v. *Yeda Research & Development Co. Ltd.* for U.S. Pat. No. 8,969,302 in the United States Patent and Trademark Office Patent Trial and Appeal Board (Case No. IPR2015-00830).

Declaration of Edward J. Fox, MD., PhD in Support of Patent Owner Yeda's Response to Institution of Inter Partes Review filed on Nov. 20, 2015, submitted as Exhibit 2129 in Inter Partes Review Case No. IPR2015-00643.

Declaration of Edward J. Fox, MD., PhD in Support of Patent Owner Yeda's Response to Institution of Inter Partes Review filed on Nov. 20, 2015, submitted as Exhibit 2129 in Inter Partes Review Case No. IPR2015-00644.

Declaration of Edward J. Fox, MD., PhD in Support of Patent Owner Yeda's Response to Institution of Inter Partes Review filed on Nov. 25, 2015, submitted as Exhibit 2129 in Inter Partes Review Case No. IPR2015-00830.

Declaration of Henry G. Grabowski, Ph.D. in Support of Patent Owner Yeda's Response to Institution of Inter Partes Review filed on Nov. 20, 2015, submitted as Exhibit 2133 in Inter Partes Review Case No. IPR2015-00643.

Declaration of Henry G. Grabowski, Ph.D. in Support of Patent Owner Yeda's Response to Institution of Inter Partes Review filed on Nov. 20, 2015, submitted as Exhibit 2133 in Inter Partes Review Case No. IPR2015-00644.

Declaration of Henry G. Grabowski, Ph.D. in Support of Patent Owner Yeda's Response to Institution of Inter Partes Review filed on Nov. 25, 2015, submitted as Exhibit 2133 in Inter Partes Review Case No. IPR2015-00830.

Declaration of Robert William Gristwood, Ph.D. in Support of Patent Owner Yeda's Response to Institution of Inter Partes Review filed on Nov. 20, 2015, submitted as Exhibit 2134 in Inter Partes Review Case No. IPR2015-00643.

Declaration of Robert William Gristwood, Ph.D. in Support of Patent Owner Yeda's Response to Institution of Inter Partes Review filed on Nov. 20, 2015, submitted as Exhibit 2134 in Inter Partes Review Case No. IPR2015-00644.

Declaration of Robert William Gristwood, Ph.D. in Support of Patent Owner Yeda's Response to Institution of Inter Partes Review filed on Nov. 25, 2015, submitted as Exhibit 2134 in Inter Partes Review Case No. IPR2015-00830.

(56) References Cited

OTHER PUBLICATIONS

Declaration of Tjalf Ziemssen, M.D., Ph.D in Support of Patent Owner Yeda's Response to Institution of Inter Partes Review filed on Nov. 20, 2015, submitted as Exhibit 2135 in Inter Partes Review Case No. IPR2015-00643.
Declaration of Tjalf Ziemssen, M.D., Ph.D in Support of Patent Owner Yeda's Response to Institution of Inter Partes Review filed on Nov. 20, 2015, submitted as Exhibit 2135 in Inter Partes Review Case No. IPR2015-00644.
Declaration of Tjalf Ziemssen, M.D., Ph.D in Support of Patent Owner Yeda's Response to Institution of Inter Partes Review filed on Nov. 25, 2015, submitted as Exhibit 2135 in Inter Partes Review Case No. IPR2015-00830.
Deposition of Stephen J. Peroutka, M.D., Ph.D., taken on behalf of the Patent Owner Yeda, at 901 New York Avenue, Washington, D.C., beginning at 9:30 a.m. on Oct. 29, 2015, before Michele E. Eddy, RPR, CRR, CLR, and Notary Public for the District of Columbia, submitted as Exhibit 1066 in Inter Partes Review Case Nos. IPR2015-00643, IPR2015-00644 and IPR2015-00830 on Nov. 18, 2015.
Slides of G. Comi, Forte: Results from a phase II, 1-year, Randomized, Double-blind, Parallel-Group, Dose Comparison Study with Glatiramer Acetate in Relapsing-remitting Multiple Sclerosis, Presented at World Congress on Treatment and Research in Multiple Sclerosis: 2008 Joint Meeting of the American, European, and Latin America Committees on Treatment and Research in Multiple Sclerosis, San Raffaele, Italy (ACTRIMS, ECTRIMS, LACTRIMS) (2008), submitted as Exhibit 2028 in Inter Partes Review Case Nos. IPR2015-00643, IPR2015-00644 and IPR2015-00830.
Jerry S. Wolinsky et al., "GLACIER: An open-label, randomized, multicenter study to assess the safety and tolerability of glatiramer acetate 40 mg three times weekly versus 20 mg daily in patients with relapsing-remitting multiple sclerosis", 4 Multiple Sclerosis and Related Disorders 370 (2015), submitted as Exhibit 2029 in Inter Partes Review Case Nos. IPR2015-00643, IPR2015-00644 and 1PR2015-00830.
C. Farina et al., "Treatment of multiple sclerosis with Copaxone (COP): Elispot assay detects COP-induced interleukin-4 and interferon-gamma response in blood cells." 124 Brain 705 (2001), submitted as Exhibit 2030 in Inter Partes Review Case Nos. IPR2015-00643, IPR2015-00644 and IPR2015-00830.
PRA, Multiple Sclerosis: Transform Your Clinical Trial with PRA (2012), submitted as Exhibit 2031 in Inter Partes Review Case Nos. IPR2015-00643, IPR2015-00644 and IPR2015-00830.
Opinion, *Endo Pharmaceuticals, Inc.* v. *Mylan Pharmaceuticals, Inc.*, No. 11-cv-00717, Document 226 (Jan. 28, 2014), submitted as Exhibit 2032 in Inter Partes Review Case Nos. IPR2015-00643, IPR2015-00644 and IPR2015-00830.
Donna Oksenberg et al., "A single amino acid difference confers major pharmacological variation between human and rodent 5-HT-1B receptors", 360 Nature 161 (1992), submitted as Exhibit 2033 in Inter Partes Review Case Nos. IPR2015-00643, IPR2015-00644 and IPR2015-00830.
Shalit et al., "Copolymer-1 (Copaxone®) induces in non-immunologic activation of connective tissue type mast cells", 97(1) J. Allergy and Clinical Immunology 345 (1996), submitted as Exhibit 2034 in Inter Partes Review Case Nos. IPR2015-00643, IPR2015-00644 and IPR2015-00830.
Order, *Endo Pharmaceuticals, Inc.* v. *Mylan Pharmaceuticals, Inc.*, No. 11-cv-00717, Document 310 (Apr. 8, 2014), submitted as Exhibit 2035 in Inter Partes Review Case Nos. IPR2015-00643, IPR2015-00644 and IPR2015-00830.
M. Fridkis-Hareli et al., "Binding motifs of copolymer 1 to multiple sclerosis- and rheumatoid arthritis-associated HLA-DR molecules." 15;162(8):4697-704. (Apr. 1999), submitted as Exhibit 2036 in Inter Partes Review Case Nos. IPR2015-00643, IPR2015-00644 and IPR2015-00830.
Notice of Abandonment issued Mar. 9, 2010 for U.S. Appl. No. 11/651,212, submitted as Exhibit 2037 in Inter Partes Review Case Nos. IPR2015-00643, IPR2015-00644 and IPR2015-00830.

B. Meibohm et al., "Basic concepts of pharmacokinetic/ pharmacodynamic (PK/PD) modelling." 35(10), 401-413 (1997), submitted as Exhibit 2038 in Inter Partes Review Case Nos. IPR2015-00643, IPR2015-00644 and IPR2015-00830.
P.H. Lambert et al., "Intradermal vaccine delivery: will new delivery systems transform vaccine administration?" 26(26) Vaccine, 3197-208 (2008); submitted as Exhibit 2039 in Inter Partes Review Case Nos. IPR2015-00643, IPR2015-00644 and IPR2015-00830.
G. Glenn et al., "Transcutaneous immunization and immunostimulant strategies", 23(4) Immunology and Allergy Clinics of N. Am., 787-813 (2003), submitted as Exhibit 2040 in Inter Partes Review Case Nos. IPR2015-00643, IPR2015-00644 and IPR2015-00830.
C.D. Partidos et al., "Immunity under the skin: potential application for topical delivery of vaccines", 21 Vaccine 776 (2003), submitted as Exhibit 2041 in Inter Partes Review Case Nos. IPR2015-00643, IPR2015-00644 and IPR2015-00830.
C. Ghose et al., "Transcutaneous immunization with Clostridium difficile toxoid A induces systemic and mucosal immune responses and toxin A-neutralizing antibodies in mice", 75 Infection & Immunity 2326 (2007), submitted as Exhibit 2042 in Inter Partes Review Case Nos. IPR2015-00643, IPR2015-00644 and IPR2015-00830.
G. Glenn et al., "Transcutaneous immunization with cholera toxin protects mice against lethal mucosal toxin challenge", 161(7) J. Immunology 3211 (1998), submitted as Exhibit 2043 in Inter Partes Review Case Nos. IPR2015-00643, IPR2015-00644 and IPR2015-00830.
R. Aharoni et al., "Specific Th2 cells accumulate in the central nervous system of mice protected against experimental autoimmune encephalomyelitis by copolymer 1", vol. 97 No. 21, Proc. Nat'l Acad. Sci. U.S.A., 11472 (2000), submitted as Exhibit 2044 in Inter Partes Review Case Nos. IPR2015-00643, IPR2015-00644 and 2015-00830.
R. Arnon et al., "Mechanism of action of glatiramer acetate in multiple sclerosis and its potential for the development of new applications" vol. 101 Supp. 2, Proc. Nat'l Acad. Sci U.S.A., 14593 (2004), submitted as Exhibit 2045 in Inter Partes Review Case Nos. IPR2015-00643, IPR2015-00644 and IPR2015-00830.
H. Varkony et al., "The Glatiramoid Class of Immunomodulator Drugs", 10 Expert Opinion Pharmacotherapy 656 (2009), submitted as Exhibit 2046 in Inter Partes Review Case Nos. IPR2015-00643, IPR2015-00644 and IPR2015-00830.
Comi et al., "Glatiramer acetate", 17 Neurologia 244 (2002), submitted as Exhibit 2047 in Inter Partes Review Case Nos. 1PR2015-00643, IPR2015-00644 and IPR2015-00830.
Chabot et al., "Cytokine production in T lymphocyte-microglia interaction is attenuated by glatiramer acetate: a mechanism for therapeutic efficacy in multiple sclerosis", 8 Multiple Sclerosis 299 (2002), submitted as Exhibit 2048 in Inter Partes Review Case Nos. IPR2015-00643, IPR2015-00644 and IPR2015-00830.
T. Ziemssen, "Neuroprotection and glatiramer acetate: the possible role in the treatment of multiple sclerosis", 541 Advanced Experimental Med. Biology 111 (2004), submitted as Exhibit 2049 in Inter Partes Review Case Nos. IPR2015-00643, IPR2015-00644 and IPR2015-00830.
Schmeisser et al., "Radioiodination of human interferon-alpha2 interferes with binding of C-terminal specific antibodies." 238 J. Immunological Methods 81 (2000), submitted as Exhibit 2050 in Inter Partes Review Case Nos. IPR2015-00643, IPR2015-00644 and IPR2015-00830.
Efimova et al., "Changes in the secondary structure of proteins labeled with 125I: CD spectroscopy and enzymatic activity studies", 264 J. of Radioanalytical and Nuclear Chemistry, 91-96 (2005), submitted as Exhibit 2051 in Inter Partes Review Case Nos. IPR2015-00643, IPR2015-00644 and IPR2015-00830.
Toutain P.L. et al., "Plasma terminal half-life", 27 J. Veterinary Pharmacological Therapy 427 (2004), submitted as Exhibit 2052 in Inter Partes Review Case Nos. IPR2015-00643, IPR2015-00644 and IPR2015-00830.
G.B. Ryan et al., Acute inflammation. A review, 86(1) Am. J. Pathology 183 (1977) submitted as Exhibit 2053 in Inter Partes Review Case Nos. IPR2015-00643, IPR2015-00644 and IPR2015-00830.

(56) References Cited

OTHER PUBLICATIONS

Shalit et al., "Copolymer-1 (Copaxone®) induces in non-immunologic activation of connective tissue type mast cells", abstract 650, J. Allergy & Clinical Immunology, 345 (1996), submitted as Exhibit 2054 in Inter Pastes Review Case Nos. IPR2015-00643, IPR2015-00644 and IPR2015-00830.

Imming et al., "Drugs, their targets and the nature and number of drug targets", 5 Nature Revs. Drug Discov. 821 (2006), submitted as Exhibit 2055 in Inter Partes Review Case Nos. IPR2D15-00643, IPR2015-00644 and IPR2015-00830.

C.B. Pert et al., "Properties of opiate-receptor binding in rat brain", 70 Proc. Natl. Acad. Sci. U.S.A. 2243 (1973), submitted as Exhibit 2056 in Inter Partes Review Case Nos. IPR2015-00643, IPR2015-00644 and IPR2015-00830.

B. Petty et al., "The effect of systemically administered recombinant human nerve growth factor in healthy human subjects." 36 Annals Neurol. 244 (1994), submitted as Exhibit 2057 in Inter Partes Review Case Nos. IPR2015-00643, IPR2015-00644 and IPR2015-00830.

S.J. Peroutka, "Antimigraine drug interactions with serotonin receptor subtypes in human brain." 23 Annals Neurol. 500 (1988), submitted as Exhibit 2058 in Inter Partes Review Case Nos. IPR2015-00643, IPR2015-00644 and IPR2015-00830.

Alk Hestvik et al., "Multiple sclerosis: glatiramer acetate induces anti-inflammatory T cells in the cerebrospinal fluid", 14 Multiple Sclerosis 749 (2008), submitted as Exhibit 2059 in Inter Partes Review Case Nos. IPR2015-00643, IPR2015-00644 and IPR2015-00830.

R. Aharoni, "The mechanism of action of glatiramer acetate in multiple sclerosis and beyond." 12 Autoimmun Rev. 543 (2013), submitted as Exhibit 2060 in Inter Partes Review Case Nos. IPR2015-00613, IPR2015-00644 and IPR2015-00830.

D. Burger et al., "Glatiramer acetate increases IL-1 receptor antagonist but decreases T cell-induced IL-1beta in human monocytes and multiple sclerosis." 106 Proc. Natl. Acad. Sci. U.S.A. 4355 (2009), submitted as Exhibit 2061 in Inter Partes Review Case Nos. IPR2015-00643, IPR2015-00644 and IPR2015-00830.

A. Mendes et al., "Classical immunomodulatory therapy in multiple sclerosis: how it acts, how it works", 69 Arq. Neuropsiquiatr. 536 (2011), submitted as Exhibit 2062 in Inter Partes Review Case Nos. IPR2015-00643, IPR2015-00644 and IPR2015-00830.

R. Aharoni et al., "Copolymer 1 induces T cells of the T helper type 2 that crossreact with myelin basic protein and suppress experimental autoimmune encephalomyelitis." 94 Proc. Natl. Acad. Sci. U.S.A. 10821 (1997), submitted as Exhibit 2063 in Inter Partes Review Case Nos. IPR2015-00643, IPR2015-00644 and IPR2015-00830.

R. Aharoni et al., "Bystander suppression of experimental autoimmune encephalomyelitis by T cell lines and clones of the Th2 type induced by copolymer 1." 91 J. Neuroimmunol. 135 (1998), submitted as Exhibit 2064 in Inter Partes Review Case Nos. IPR2015-00643, IPR2015-00644 and IPR2015-00830.

O. Neuhaus et al., "Mechanisms of action of glatiramer acetate in multiple sclerosis." 56 Neurology 702 (2001), submitted as Exhibit 2065 in Inter Partes Review Case Nos. IPR2015-00643, IPR2015-00644 and IPR2015-00830.

T. Ziemssen et al., "Glatiramer acetate-specific T-helper 1- and 2-type cell lines produce BDNF: implications for multiple sclerosis therapy." 125 Brain 2381 (2002), submitted as Exhibit 2066 in Inter Partes Review Case Nos. IPR2015-00643, IPR2015- 00644 and IPR2015-00830.

Miller et al., "Treatment of multiple sclerosis with copolymer-1 (Copaxone): implicating mechanisms of Th1 to Th2/Th3 immune-deviation." 92 J. Neuroimmunol. 113 (1998), submitted as Exhibit 2067 in Inter Partes Review Case Nos. IPR2015-00643, IPR2015-00644 and IPR2015-00830.

Neuhaus et al., "Multiple sclerosis: comparison of copolymer-1-reactive T cell lines from treated and untreated subjects reveals cytokine shift from T helper 1 to T helper 2 cells." 97 Proc. Natl. Acad. Sci. U.S.A. 7452 (2000), submitted as Exhibit 2068 in Inter Partes Review Case Nos. IPR2015-00643, IPR2015-00644 and IPR2015-00830.

Duda et al., "Glatiramer acetate (Copaxone) induces degenerate, Th2-polarized immune responses in patients with multiple sclerosis." 105 J. Clin. Invest. 967 (2000), submitted as Exhibit 2069 in Inter Partes Review Case Nos. IPR2015-00643, IPR2015-00644 and IPR2015-00830.

Hori et al., "Control of regulatory T cell development by the transcription factor Foxp3." 299 Science 1057 (2003), submitted as Exhibit 2070 in Inter Partes Review Case Nos. IPR2015-00643, IPR2015-00644 and IPR2015-00830.

Brunkow et al., "Disruption of a new forkhead/winged-helix protein, scurfin, results in the fatal lymphoproliferative disorder of the scurfy mouse", 27 Nature Genet. 68 (2001), submitted as Exhibit 2071 in Inter Partes Review Case Nos. IPR2015-00643, IPR2015-00644 and IPR2015-00830.

Viglietta et al., "DA. Loss of functional suppression by CD4+CD25+ regulatory T cells in patients with multiple sclerosis." 199 J. Exp. Med. 971 (2005), submitted as Exhibit 2072 in Inter Partes Review Case Nos. IPR2015-00643, IPR2015-00644 and IPR2015-00830.

Hong et al., "Induction of CD4+CD25+ regulatory T cells by copolymer-I through activation of transcription factor Foxp3", 102 Proc. Natl. Acad. Sci. U.S. A. 6449 (2005), submitted as Exhibit 2073 in Inter Partes Review Case Nos. IPR2015-00643, IPR2015-00644 and IPR2015-00830.

Wekerle et al., "Cellular immune reactivity within the CNS." Trends Neurosci. 9 TINS 271-277 (1986), submitted as Exhibit 2074 in Inter Partes Review Case Nos. IPR2015-00643, IPR2015-00644 and IPR2015-00830.

W.F. Hickey, "Migration of hematogenous cells through the blood-brain barrier and the initiation of CNS inflammation." 1 Brain Pathol. 97 (1999), submitted as Exhibit 2075 in Inter Partes Review Case Nos. IPR2015-00643, IPR2015-00644 and IPR2015-00830.

Weber et al., "Multiple sclerosis: glatiramer acetate inhibits monocyte reactivity in vitro and in vivo." 127 Brain 1370 (2004), submitted as Exhibit 2076 in Inter Partes Review Case Nos. IPR2015-00643, IPR2015-00644 and IPR2015-00830.

Menge et al., "Disease-modifying agents for multiple sclerosis: recent advances and future prospects", 68 Drugs 2445 (2008), submitted as Exhibit 2077 in Inter Partes Review Case Nos. IPR2015-00643, IPR2015-00644 and IPR2015-00830.

Sodoyez et al., "125I-insulin: kinetics of interaction with its receptors and rate of degradation in vivo." 239 Am. J. Physiol. E3-8. (1980), submitted as Exhibit 2078 in Inter Partes Review Case Nos. IPR2015-00643, IPR2015-00644 and IPR2015-00830.

Wroblewski VJ. "Mechanism of deiodination of 125I-human growth hormone in vivo. Relevance to the study of protein disposition", 42 Biochem. Pharmacol. 889 (1991), submitted as Exhibit 2079 in Inter Partes Review Case Nos. IPR2015-00643, IPR2015-00644 and IPR2015-00830.

Alastair Monro, "The paradoxical lack of interspecies correlation between plasma concentrations and chemical carcinogenicity", 18 Regulatory Toxicology & Pharmacology 115 (1993), submitted as Exhibit 2080 in Inter Partes Review Case Nos. IPR2015-00643, IPR2015-00644 and IPR2015-00830.

Robert T. O'Neill, "Secondary endpoints cannot be validly analyzed if the primary endpoint does not demonstrate clear statistical significance", 18 Controlled Clinical Trials 550 (1997), submitted as Exhibit 2081 in Inter Partes Review Case Nos. IPR2015-00643, IPR2015-00644 and IPR2015-00830.

Karsten Beer et al., "The prevalence of injection-site reactions with disease-modifying therapies and their effect on adherence in patients with multiple sclerosis: an observational study", 11 BMC Neurology 144 (2011), submitted as Exhibit 2082 in Inter Partes Review Case Nos. IPR2015-00643, IPR2015-00644 and IPR2015-00830.

Tjalf Ziemssen et al., "Glatiramer acetate: mechanisms of action in multiple sclerosis", 79 Int'l Rev. Neurobiology 537 (2007), submitted as Exhibit 2083 in Inter Partes Review Case Nos. IPR2015-00643, IPR2015-00644 and IPR2015-00830.

(56) References Cited

OTHER PUBLICATIONS

Tjalf Ziemssen, "Modulating processes within the central nervous system is central to therapeutic control of multiple sclerosis", 252 J. Neurology Suppl. 5 V/38-V.45 (2005), submitted as Exhibit 2084 in Inter Partes Review Case Nos. IPR2015-00643, IPR2015-00644 and IPR2015-00830.

Tjalf Ziemssen et al., "Presence of glatiramer acetate-specific TH2 cells in the cerebrospinal fluid of patients with multiple sclerosis 12 months after the start of therapy with glatiramer acetate." 1 J. Neurodegeneration & Regeneration 1 (Sep. 9, 2008), submitted as Exhibit 2085 in Inter Partes Review Case Nos. IPR2015-00643, IPR2015-00644 and IPR2015-00830.

H.P. Rang et. al., "8. Drug Elimination and Pharmacokinetics" in: H.P. Rang et. al., *Pharmacology* (Elsevier 2005, 5th ed., 1987), pp. 106-119, submitted as Exhibit 2086 in Inter Partes Review Case Nos. IPR2015-00643, IPR2015-00644 and IPR2015-00830.

Donald W. Paty, "The Interferon-β1b Clinical Trial and Its Implications for Other Trials", 36 Annals Neurology S113 (Supp. 1994), submitted as Exhibit 2087 in Inter Partes Review Case Nos. IPR2015-00643, IPR2015-00644 and IPR2015-00830.

Leonora K. Fisniku, "Gray Matter Atrophy is Related to Long-Term Disability in Multiple Sclerosis", 64 Annals Neurology 247 (2008), submitted as Exhibit 2088 in Inter Partes Review Case Nos. IPR2015-00643, IPR2015-00644 and IPR2015-00830.

Omar Kahn et al., "Three Times Weekly Glatiramer Acetate in Relapsing-Remitting Multiple Sclerosis", 73 Annals of Neurology 705 (2013), submitted as Exhibit 2089 in Inter Partes Review Case Nos. IPR2015-00643, IPR2015-00644 and IPR2015-00830.

Phillip D. Rumrill Jr., "Multiple sclerosis: Medical and psychosocial aspects, etiology, incidence, and prevalence", 31 J. Vocational Rehabilitation 75 (2009), submitted as Exhibit 2090 in Inter Partes Review Case Nos. IPR2015-00643, IPR2015-00644 and IPR2015-00830.

H.T. Katz et al., "Successful desensitization to glatiramer acetate (Copaxone) in two patients with multiple sclerosis" in: Abstract Book of 2003 Annual Meeting, American College of Allergy, Asthma & Immunology, New Orleans, LA (vol. 92, Jan. 2004), submitted as Exhibit 2091 in Inter Partes Review Case Nos. IPR2015-00643, IPR2015-00644 and IPR2015-00830.

Maria Zellner et al., "Quantitative validation of different protein precipitation methods in proteome analysis of blood platelets", 26 Electrophoresis 2481 (2005), submitted as Exhibit 2092 in Inter Partes Review Case Nos. IPR2015-00643, IPR2015-00644 and IPR2015-00830.

Mariana Castells, "Rapid Desensitization for Hypersensitivity Reactions to Medications", 29 Immunology and Allergy Clinics of North America 585 (2009), submitted as Exhibit 2093 in Inter Partes Review Case Nos. IPR2015-00643, IPR2015-00644 and IPR2015-00830.

Robert Zivadinov et al., Poster titled "MRI Indicators of Brain Tissue Loss: 3-Year Results of the Glatiramer Acetate Low-Frequency Administration (GALA) Open-Label Extension Study in Relapsing-Remitting Multiple Sclerosis", Presented at The American Academy of Neurology 2015 Annual Meeting, Washington, DC (Apr. 18-25, 2015), submitted as Exhibit 2094 in Inter Partes Review Case Nos. IPR2015-00643, IPR2015-00644 and IPR2015-00830.

E. Rubinchik et al., "Responsiveness of human skin mast cells to repeated activation: an in vitro study", 53 Allergy 14 (1998), submitted as Exhibit 2095 in Inter Partes Review Case Nos. IPR2015-00643, IPR2015-00644 and IPR2015-00830.

Daniel Wynn et.al., Poster titled "Patient Experience with Glatiramer Acetate 40mg/1 ml Three-Times Weekly Treatment for Relapsing-Remitting Multiple Sclerosis: Results from the Glacier Extension Study", Presented at the 8th Congress of the Pan-Asian Committee for Treatment and Research in Multiple Sclerosis, Seoul, Republic of Korea (Nov. 19-21, 2015), submitted as Exhibit 2096 in Inter Partes Review Case Nos. IPR2015-00643, IPR2015- 00644 and IPR2015-00830.

Avonex® (Inferon beta-1a) IM Injection, published 2008 by Biogen Idec Inc., submitted as Exhibit 2097 in Inter Partes Review Case Nos. IPR2015-00643, IPR2015-00644 and IPR2015-00830.

Rebif Prescribing Information, published 2009 by Pfizer, submitted as Exhibit 2098 in Inter Partes Review Case Nos. IPR2015-00643, IPR2015-00644 and IPR2015-00830.

Extavia Highlights of Prescribing Information, published Aug. 2009 by Novartis, submitted as Exhibit 2099 in Inter Partes Review Case Nos. IPR2015-00643, IPR2015-00644 and IPR2015-00830.

Curriculum Vitae of Edward J. Fox. MD., PhD., FAAN, submitted as Exhibit 2100 in Inter Partes Review Case Nos. IPR2015-00643 and IPR2015-00644 on Nov. 20, 2015 and in IPR2015-00830 on Nov. 25, 2015.

Soelberg Sorensen et al., "Clinical Importance of neutralizing antibodies against interferon beta in patients with rerlapsing-remitting multiple sclerosis", 362 The Lancet 1184 (Oct. 11, 2003), submitted as Exhibit 2101 in Inter Partes Review Case Nos. IPR2015-00643, IPR2015-00644 and IPR2015-00830.

Jan J.M. de Vijlder, "Primary congenital hypothyroidism: defects in iodine pathway", 149 Eur. J. Endocrinology 247 (2003), submitted as Exhibit 2102 in Inter Partes Review Case Nos. IPR2015-00643, IPR2015-00644 and IPR2015-00830.

C.S. Randall, "5. Approaches to the Analysis of Peptides" in: Vincent H. L. Lee ed. *Peptide and Protein Drug Delivery*, New York, Marcel Dekker, Inc. 1991, pp. 203-246, submitted as Exhibit 2103 in Inter Partes Review Case Nos. IPR2015-00643, IPR2015-00644 and IPR2015-00830.

Curriculum Vitae of Dr. Henry George Grabowski, submitted as Exhibit 2104 in Inter Partes Review Case Nos. IPR2015-00643 and IPR2015-00644 on Nov. 20, 2015 and in IPR2015-00830 on Nov. 25, 2015.

List of Testimony of Henry G. Grabowski, submitted as Exhibit 2105 in Inter Partes Review Case Nos. IPR2015-00643 and IPR2015-00644 on Nov. 20, 2015 and in IPR2015-00830 on Nov. 25, 2015.

Documents Relied Upon by Grabowski, submitted as Exhibit 2106 in Inter Partes Review Case Nos. IPR2015-00643 and IPR2015-00644 on Nov. 20, 2015 and in IPR2015-00830 on Nov. 25, 2015.

Table: Approval Timeline, Multiple Sclerosis Drugs, submitted as Exhibit 2107 in Inter Partes Review Case Nos. IPR2015-00643 and IPR2015-00644 on Nov. 20, 2015 and in IPR2015-00830 on Nov. 25, 2015.

Redacted Figure: Copaxone® 40mg/mL Wholesale Dollar Sales (Q1 2014-Q3 2015), submitted as Exhibit 2108 in Inter Partes Review Case Nos. IPR2015-00643 and IPR2015-00644 on Nov. 20, 2015 and in IPR2015-00830 on Nov. 25, 2015.

Redacted Figure: Copaxone® 40mg/mL Extended Units (Q1 2014-Q3 2015), submitted as Exhibit 2109 in Inter Partes Review Case Nos. IPR2015-00643 and IPR2015-00644 on Nov. 20, 2015 and in IPR2015-00830 on Nov. 25, 2015.

Redacted Figure: Copaxone® 40mg/mL Total Prescriptions (Q1 2014-Q3 2015), submitted as Exhibit 2110 in Inter Partes Review Case Nos. IPR2015-00643 and IPR2015-00644 on Nov. 20, 2015 and in IPR2015-00830 on Nov. 25, 2015.

Redacted Figure: Copaxone® 40mg/mL New Prescriptions (Q1 2014-Q3 2015), submitted as Exhibit 2111 in Inter Partes Review Case Nos. IPR2015-00643 and IPR2015-00644 on Nov. 20, 2015 and in IPR2015-00830 on Nov. 25, 2015.

Redacted Figure: Multiple Sclerosis Drugs Share of Wholesale Dollar Sales (Q4 2009-Q3 2015), submitted as Exhibit 2112 in Inter Partes Review Case Nos. IPR2015-00643 and IPR2015-00644 on Nov. 20, 2015 and in IPR2015-00830 on Nov. 25, 2015.

Redacted Figure: Multiple Sclerosis Drugs Share of Total Prescriptions (Q4 2009-Q3 2015), submitted as Exhibit 2113 in Inter Partes Review Case Nos. IPR2015-00643 and IPR2015-00644 on Nov. 20, 2015 and in IPR2015-00830 on Nov. 25, 2015.

Redacted Figure: Multiple Sclerosis Drugs Share of New Prescriptions (Q4 2009-Q3 2015), submitted as Exhibit 2114 in Inter Partes Review Case Nos. IPR2015-00643 and IPR2015-00644 on Nov. 20, 2015 and in IPR2015-00830 on Nov. 25, 2015.

(56) References Cited

OTHER PUBLICATIONS

Figure: Rationale for Requesting Copaxone, submitted as Exhibit 2115 in Inter Partes Review Case Nos. IPR2015-00643 and IPR2015-00644 on Nov. 20, 2015 and in IPR2015-00830 on Nov. 25, 2015.
Figure: Perception of 3-times-a-week Copaxone 40mg compared to Daily Copaxone 20mg, submitted as Exhibit 2116 in Inter Partes Review Case Nos. IPR2015-00643 and IPR2015-00644 on Nov. 20, 2015 and in IPR2015-00830 on Nov. 25, 2015.
Figure: Rationale for Discussing 20mg and 40mg for First Line Patients, submitted as Exhibit 2117 in Inter Partes Review Case Nos. IPR2015-00643 and IPR2015-00644 on Nov. 20, 2015 and in IPR2015-00830 on Nov. 25, 2015.
Figure: Perceptions of Copaxone® 40mg compared to Daily Generic GA, submitted as Exhibit 2118 in Inter Partes Review Case Nos. IPR2015-00643 and IPR2015-00644 on Nov. 20, 2015 and in IPR2015-00830 on Nov. 25, 2015.
Figure: Perceptions of Copaxone® 40mg vs. 20mg, submitted as Exhibit 2119 in Inter Partes Review Case Nos. IPR2015-00643 and IPR2015-00644 on Nov. 20, 2015 and in IPR2015-00830 on Nov. 25, 2015.
Redacted Figure: Copaxone® Total Prescriptions (Q4 2009-Q3 2015), submitted as Exhibit 2120 in Inter Partes Review Case Nos. IPR2015-00643 and IPR2015-00644 on Nov. 20, 2015 and in IPR2015-00830 on Nov. 25, 2015.
Redacted Figure: Copaxone® 20 mg/mL, Copaxone® 40 mg/mL, and Glatopa™ Net Prescriptions Flow (Oct. 26, 2012-Oct. 9, 2015), submitted as Exhibit 2121 in Inter Partes Review Case Nos. IPR2015-00643 and IPR2015-00644 on Nov. 20, 2015 and in IPR2015-00830 on Nov. 25, 2015.
Table: Total Promotional Spending to Sales Ratio, submitted as Exhibit 2122 in Inter Partes Review Case Nos. IPR2015-00643 and IPR2015-00644 on Nov. 20, 2015 and in IPR2015-00830 on Nov. 25, 2015.
G. Comi et al., "Early Treatment with glatiramer acetate is efficacious in delaying conversion to clinically definite multiple sclerosis in patients presenting with clinically isolated syndrome and brain lesions detected by MRI", 374 Lancet 1503 (Oct. 31, 2009), submitted as Exhibit 2123 in Inter Partes Review Case Nos. IPR2015-00643, IPR2015-00644 and IPR2015-00830.
R.M. Valenzuela et al., "Clinical response to glatiramer acetate correlates with modulation of IFN-γ and IL-4 expression in multiple sclerosis", 13 Multiple Sclerosis 754 (2007), submitted as Exhibit 2124 in Inter Partes Review Case Nos. IPR2015-00643, 1PR2015-00644 and IPR2015-00830.
Y. Blanco et al., "Effect of glatiramer acetate (Copaxone®) on the immunophenotypic and cytokine profile and BDNF production in multiple sclerosis: A longitudinal study", 406 Neuroscience Letters 270 (2006), submitted as Exhibit 2125 in Inter Partes Review Case Nos. IPR2015-00643, IPR2015-00644 and IPR2015-00830.
M. Chen et al., "Sustained immunological effects of Glatiramer acetate in patients with multiple sclerosis treated for over 6 years", 201 J. of Neurological Sciences 71 (2002), submitted as Exhibit 2126 in Inter Partes Review Case Nos. IPR2015-00643, IPR2015-00644 and 1PR2015-00830.
Zhao Rong Chen et al., "MU Receptor Binding of Some Commonly Used Opioids and Their Metabolites", 48 Life Sciences 2165 (1991), submitted as Exhibit 2127 in Inter Partes Review Case Nos. IPR2015-00643, IPR2015-00644 and IPR2015-00830.
Alison Palkhivala, "Doubling the Dose of Glatiramer Acetate Does Not Increase Efficacy", Medscape Medical News (Sep. 22, 2008), submitted as Exhibit 2128 in Inter Partes Review Case Nos. IPR2015-00643, IPR2015-00644 and IPR2015-00830.
Curriculum Vitae of Robert William Gristwood PhD, submitted as Exhibit 2130 in Inter Partes Review Case Nos. IPR2015-00643 and IPR2015-00644 on Nov. 20, 2015 and in IPR2015-00830 on Nov. 25, 2015.
Curriculum Vitae of Tjalf Ziemssen, submitted as Exhibit 2131 in Inter Partes Review Case Nos. IPR2015-00643 and IPR2015-00644 on Nov. 20, 2015 and in IPR2015-00830 on Nov. 25, 2015.

Ziemssen's MS clinical trials, submitted as Exhibit 2132 in Inter Partes Review Case Nos. IPR2015-00643 and IPR2015-00644 on Nov. 20, 2015 and in IPR2015-00830 on Nov. 25, 2015.
Deposition of Stephen J. Peroutka, taken at Washington, D.C., on Oct. 29, 2015, submitted as Exhibit 1066 in Inter Partes Review Case Nos. IPR2015-00643, IPR2015-00644 and IPR2015-00830 on Nov. 18, 2015.
Aug. 25, 2015 Decision on Institution of Inter Partes Review, entered in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).
Aug. 25, 2015 Decision on Institution of Inter Partes Review, entered in connection with *Mylan Pharmaceuticals Inc.* v. *Yeda Research & Development Co. Ltd.* for U.S. Pat. No. 8,399,413 in the United States Patent and Trademark Office Patent Trial and Appeal Board (Case No. IPR2015-00644).
Sep. 1, 2015 Decision on Institution of Inter Partes Review, entered in connection with *Mylan Pharmaceuticals Inc.* v. *Yeda Research & Development Co. Ltd.* for U.S. Pat. No. 8,969,302 in the United States Patent and Trademark Office Patent Trial and Appeal Board (Case No. IPR2015-00830).
Apr. 10, 2015 Complaint, filed in connection with *Teva Pharmaceuticals USA, Inc.*, et al., v. *Doctor Reddy's Laboratories, Ltd., et al.* in the United States District Court for the District of Delaware (Case. No. 1:15-cv-00306-GMS).
May 7, 2015 First Amended Complaint, filed in connection with *Teva Pharmaceuticals Usa, Inc.*, et al., v. *Doctor Reddy's Laboratories, Ltd., et al.* in the United States District Court for the District of Delaware (Case. No. 1:15-cv-00306-GMS).
Jun. 12, 2015 Answer to Amneal's Counterclaims in the United States District Court for District of Delaware (Case No. 1:14-cv-01171-GMS) (Consolidated).
Jun. 15, 2015 Answer to Sandoz, Inc. and Momenta Pharmaceuticals, Inc.'s Counterclaims in the United States District Court for District of Delaware (Case No. 1:14-cv-01171-GMA) (Consolidated).
Jun. 15, 2015 Answer to Amneal's Counterclaims in the United States District Court for District of Delaware (Case No. 1:14-cv-01171-GMS) (Consolidated).
Jun. 15, 2015 Answer to Synthon Pharmaceuticals Inc., Synthon B.V., and Synthon S.R.O.'s Counterclaims in the United States District Court for District of Delaware (Case No. 1:14-cv-01171-GMS) (Consolidated).
Jun. 15, 2015 Answer to DRL's Counterclaims in the United States District Court for District of Delaware (Case No. 1:14-cv-01171-GMS) (Consolidated).
Aug. 14, 2015 Joint Claim Construction Chart in the United States District Court for District of Delaware (Case No. 1:14-cv-01171-GMS) (Consolidated).
Oct. 2, 2015 Second Declaration of Edward J. Fox, M.D., Ph.D. in the United States District Court for District of Delaware (Case No. 1:14-cv-01171-GMS) (Consolidated).
Oct. 2, 2015 Second Declaration of Andrew R. Pachner, M.D. in the United States District Court for District of Delaware (Case No. 1:14-cv-01171-GMS) (Consolidated).
Oct. 2, 2015 Defendant's Responsive Claim Construction Brief in the United States District Court for District of Delaware (Case No. 1:14-cv-01171-GMS) (Consolidated).
Oct. 9, 2015 Plaintiff's Answering Claims Construction Brief in the United States District Court for District of Delaware (Case No. 1:14-cv-01171-GMA) (Consolidated).
Sep. 11, 2015 Defendant's Opening Claims Construction Brief in the United States District Court for District of Delaware (Case No. 1:14-cv-01171-GMS) (Consolidated).
Sep. 11, 2015 Plaintiff's Opening Claims Construction Brief in the United States District Court for District of Delaware (Case No. 1:14-cv-01171-GMS) (Consolidated).
Sep. 11, 2015 Declaration of Edward J. Fox, M.D., Ph.D. in the United States District Court for District of Delaware (Case No. 1:14-cv-01171-GMS) (Consolidated).

(56) References Cited

OTHER PUBLICATIONS

Sep. 11, 2015 Declaration of Andrew R. Pachner, M.D. in the United States District Court for District of Delaware (Case No. 1:14-cv-01171-GMS) (Consolidated).
Mar. 3, 2015 Petition for Inter Partes Review, filed in connection with *Mylan Pharmaceuticals Inc.* v. *Yeda Research & Development Co. Ltd.* for U.S. Pat. No. 8,969,302 in the United States Patent and Trademark Office Patent Trial and Appeal Board (Case No. IPR2015-00830).
Declaration of Stephen J. Peroutka, M.D., Ph.D., submitted as Exhibit 1003 in Inter Parties review Case No. IPR2015-00830).
Expert Declaration of Ari Green, M.D. in Support of Petition for Inter Partes Review of U.S. Pat. No. 8,969,302, submitted as Exhibit 1004 in Inter Partes Review Case No. IPR2015-00830.
Zeev Meiner et al., "Copolymer 1 in relapsing-remitting multiple sclerosis: a multi-centre trial" in: Abramsky et al., *Frontiers in Multiple Sclerosis: Clinical Research and Therapy* (London, Martin Dunitz, 1997), pp. 213-221, submitted as Exhibit 1009 in Inter Partes Review Case Nos. IPR2015-00643, IPR2015-00644 and IPR2015-00830.
Flechter et al., "Comparison of glatiramer acetate (Copaxone®) and interferon β-1b (Betaferon®) in multiple sclerosis patients: an open-label 2-year follow up", 197 Journal of the Neurological Sciences, 51-55 (2002), submitted as Exhibit 1012 in Inter Partes Review Case Nos. IPR2015-00643, IPR2015-00644 and IPR2015-00830.
Miller, The importance of early diagnosis of multiple sclerosis, 10(3) (Suppl. S-b) J.Manag. Care Pharm., S4-11 (2004), submitted as Exhibit 1013 in Inter Partes Review Case Nos. IPR2015-00643, IPR2015-00644 and IPR2015-00830.
Bornstein, "Multiple Sclerosis: Trial of a Synthetic Polypeptide", 11:3 Annals of Neurology, 317-19 (1982), submitted as Exhibit 1014 in Inter Partes Review Case Nos. IPR2015-00643, IPR2015-00644 and IPR2015-00830.
Bornstein et al., "Clinical Trials of Copolymer I in Multiple Sclerosis", 436 Annals New York Academy of Sciences, 366-372 (1984), submitted as Exhibit 1015 in Inter Partes Review Case Nos. IPR2015-00643, IPR2015-00644 and IPR2015-00830.
Bornstein et al., "A Pilot Trial of COP 1 in Exacerbating-Remitting Multiple Sclerosis", 317:7 The New England Journal of Medicine, 408-14 (1987), submitted as Exhibit 1016 in Inter Partes Review Case Nos. IPR2015-00643, IPR2015-00644 and IPR2015-00830.
FDA, Guideline for Industry: Dose-Response Information to Support Drug Registration (1994), submitted as Exhibit 1017 in Inter Partes Review Case Nos. IPR2015-00643, IPR2015-00644 and IPR2015-00830.
Johnson et al., "Copolymer 1 reduces relapse rate and improves disability in relapsing-remitting multiple sclerosis", 43 Neurology, 1268-1276 (1995), submitted as Exhibit 1018 in Inter Partes Review Case Nos. IPR2015-00643, IPR2015-00644 and IPR2015-00830.
Affidavit of Marlene S. Bobka dated Jan. 5, 2015, submitted as Exhibit 1019 in Inter Partes Review Case Nos. IPR2015-00643, IPR2015-00644 and IPR2015-00830.
Arnon, The Development of Cop 1(Copaxone®), An Innovative Drug for the Treatment of Multiple Sclerosis: Personal Reflections, 50 Immunology Letters 1-15 (1996), submitted as Exhibit 1020 in Inter Partes Review Case Nos. IPR2015-00643, IPR2015-00644 and IPR2015-00830.
Benet et al., "Pharmacokinetics: The Dynamics of Drug Absorption, Distribution, and Elimination" in: Goodman & Gilman, *The Pharmacological Basis of Therapeutics* (New York, McGraw-Hill, 1995), pp. 3-27, submitted as Exhibit 1021 in Inter Partes Review Case Nos. IPR2015-00643, IPR2015-00644 and IPR2015-00830.
Lobel et al., "Copolymer-1", 21(2) Drugs of the Future, 131-134 (1996), submitted as Exhibit 1022 in Inter Partes Review Case Nos. IPR2015-00643, IPR2015-00644 and IPR2015-00830.
Haines et al., Linkage of the MHC to Familial Multiple Sclerosis Suggests Genetic Heterogeneity. The Multiple Sclerosis Genetics Group, Hum.Mol. Genet. 7:1229-34 (Aug. 1998), submitted as Exhibit 1023 in Inter Partes Review Case Nos. IPR2015-00643, IPR2015-00644 and IPR2015-00830.
U.S. Pat. No. 6,342,476, issued Jan. 29, 2002 (Konfino, et al.), submitted as Exhibit 1024 in Inter Partes Review Case Nos. IPR2015-00643, IPR2015-00644 and IPR2015-00830.
Ge et al., Glatiramer Acetate (Copaxone) Treatment in Relapsing-Remitting MS: Quantitative MR Assessment, 54 Neurology, 813-17 (2000), submitted as Exhibit 1025 in Inter Partes Review Case Nos. IPR2015-00643, IPR2015-00644 and IPR2015-00830.
Comi et al. "European/Canadian multicenter, double-blind, randomized, placebo-controlled study of the effects of glatiramer acetate on magnetic resonance imagine-measured disease activity and burden in patients with relapsing multiple sclerosis". Ann Neurol. 49:290-7 (2001), submitted as Exhibit 1026 in Inter Partes Review Case Nos. IPR2015-00643, IPR2015-00644 and IPR2015-00830.
Jean-Pierre Boissel et al. "Using pharmacokinetic-pharmacodynamic relationships to predict the effect of poor compliance," Clin. Pharmacol. 41:1-6 (2002), submitted as Exhibit 1027 in Inter Partes Review Case Nos. IPR2015-00643 and IPR2015-00643.
McDonald et al., Recommended Diagnostic Criteria for Multiple Sclerosis: Guidelines from the International Panel on the Diagnosis of Multiple Sclerosis, Ann. Neurol. 50:121-27 (2001), submitted as Exhibit 1027 in Inter Partes Review Case No. IPR2015-00830.
McBride, "Nonadherence to Immunomodulation in Multiple Sclerosis," abstract for Second International Multiple Sclerosis Week Multiple Sclerosis: A World View, a conference held on Jun. 5-9, 2002 at Chicago, Illinois, submitted as Exhibit 1028 in Inter Partes Review Case Nos. IPR2015-00643, IPR2015-00644 and IPR2015-00830.
Simpson et al., Adis Drug Evaluation—Glatiramer Acetate A Review of its use in Relapsing-Remitting Multiple Sclerosis, 16:12 CNS Drugs, 825-50, 834 (2002), submitted as Exhibit 1029 in Inter Partes Review Case Nos. IPR2015-00643, IPR2015-00644 and IPR2015-00830.
Edgar, et al., "Lipoatrophy in Patients with Multiple Sclerosis on Glatiramer Acetate", 31 Can. J. Neurol. Sci., 58-63 (2004), submitted as Exhibit 1030 in Inter Partes Review Case Nos. IPR2015-00643, IPR2015-00644 and IPR2015-00830.
Rich et al., Stepped-care approach to treating MS: A managed care treatment algorithm, J. Managed Care Pharm. 10:S26-S32 (Jun. 2004), submitted as Exhibit 1031 in Inter Partes Review Case Nos. IPR2015-00643 and IPR2015-00643, and Exhibit 1058 in Inter Partes Review Case No. IPR2015-00830.
Ziemssen et al., Effects of Glatiramer Acetate on Fatigue and Days of Absence from Work in First-Time Treated Relapsing-Remitting Multiple Sclerosis, Hlth. &Qual. Life Outcomes 6:67 (2008), submitted as Exhibit 1045 in Inter Partes Review Case Nos. IPR2015-00643 and IPR2015-00643, and Exhibit 1031 in Inter Partes Review Case No. IPR2015-00830.
Stuart, Clinical Management of Multiple Sclerosis: The Treatment Paradigm and Issues of Patient Management, J. Managed Care Pharmacy 10:S19-S25 (Jun. 2004), submitted as Exhibit 1032 in Inter Partes Review Case Nos. IPR2015-00643, IPR2015-00644 and IPR2015-00830.
Bakshi et al., Imaging of Multiple Sclerosis: Role in Neurotherapeutics, 2(2) Neurorx, 277-303 (2005), submitted as Exhibit 1033 in Inter Partes Review Case Nos. IPR2015-00643, IPR2015-00644 and IPR2015-00830.
Beringer et al., "Clinical Pharmacokinetics and Pharmacodynamics", in Remington: The Science and Practice of Pharmacy, 1191-1205, 1197, 1201 (Paul Beringer ed., 2005), submitted as Exhibit 1034 in Inter Partes Review Case Nos. IPR2015-00643, IPR2015-00644 and IPR2015-00830.
Franklin et al., "Drug Absorption, Action, and Disposition", in Remington: The Science and Practice of Pharmacy \, 1142-1170, 1167 (Paul Beringer ed., 2005), submitted as Exhibit 1035 in Inter Partes Review Case Nos. IPR2015-00643, IPR2015-00644 and IPR2015-00830.
PCT International Application Publication No. WO 2005/120542, published Dec. 22, 2005 (Rasmussen), submitted as Exhibit 1036 in Inter Partes Review Case Nos. IPR2015-00643, IPR2015-00644 and IPR2015-00830.

(56) References Cited

OTHER PUBLICATIONS

Devonshire et al., "The Global Adherence Project—A Multicentre Observational Study on Adherence to Disease-Modifying Therapies in Patients Suffering from Relapsing-Remitting Multiple Sclerosis", Multiple Sclerosis 12:S1(P316) (2006), submitted as Exhibit 1037 in Inter Partes Review Case Nos. IPR2015-00643, IPR2015-00644 and IPR2015-00830.
Ford et al., "A Prospective Open-Label Study of Glatiramer Acetate: Over a Decade of Continuous Use in Multiple Sclerosis Patients", 12 Multiple Sclerosis, 309-320 (2006), submitted as Exhibit 1038 in Inter Partes Review Case Nos. IPR2015-00643, IPR2015-00644 and IPR2015-00830.
Frohman, Multiple Sclerosis—The Plaque and its Pathogenesis, New England J.Med. 354:942-55 (2006), submitted as Exhibit 1039 in Inter Partes Review Case Nos. IPR2015-00643, IPR2015-00644 and IPR2015-00830.
Kragt et al., How Similar are Commonly Combined Criteria for EDSS Progression in Multiple Sclerosis?, 12(6) Multiple Sclerosis 782-786 (2006), submitted as Exhibit 1040 in Inter Partes Review Case Nos. IPR2015-00643, IPR2015-00644 and IPR2015-00830.
Manso et al., "Life Cycle Management of Ageing Pharmaceutical Assets", 3:7 Pharmaceutical Law Insight, (2006), submitted as Exhibit 1041 in Inter Partes Review Case Nos. IPR2015-00643, IPR2015-00644 and IPR2015-00830.
Soares et al., Localized Panniculitis Secondary to Subcutaneous Glatiramer Acetate Injections for the Treatment of Multiple Sclerosis: A Clinicopathologic and Immunohistochemicl Study, J. Am. Aced. Derm. 55:968-74 (2006), submitted as Exhibit 1042 in Inter Partes Review Case Nos. IPR2015-00643, IPR2015-00644 and IPR2015-00830.
Klauer and Zettl, "Compliance, Adherence and the Treatment of Multiple Sclerosis", J. Neurol. 255 [Suppl.6]:87-92 (2008), submitted as Exhibit 1043 in Inter Partes Review Case Nos. IPR2015-00643, IPR2015-00644 and IPR2015-00830.
Pelidou et al., Multiple Sclerosis Presented as Clinically Isolated Syndrome: The Need for Early Diagnosis and Treatment, Ther. Clin. Riskmanagement 4:627-30 (Jun. 2008), submitted as Exhibit 1044 in Inter Partes Review Case Nos. IPR2015-00643, IPR2015-00644 and IPR2015-00830.
Copaxone®, Food and Drug Administration Approved Labeling, 2001 (NDA 20-622/S-015/S-015), submitted as Exhibit 1047 in Inter Partes Review Case Nos. IPR2015-00643, IPR2015-00644 and IPR2015-00830.
Rebif® (interferon beta-1a), Product Label, 2003, submitted as Exhibit 1049 in Inter Partes Review Case Nos. IPR2015-00643, IPR2015-00644 and IPR2015-00830.
Avonex® (interferon beta-1a) IM Injection, Product Label, 2006, submitted as Exhibit 1050 in Inter Partes Review Case Nos. IPR2015-00643, IPR2015-00644 and IPR2015-00830.
Tysabri®, Product Label, 2008, submitted as Exhibit 1051 in Inter Partes Review Case Nos. IPR2015-00643, IPR2015-00644 and IPR2015-00830.
Extavia®, Abbreviated Drug Monograph: Interferon beta 1b (Extavia®), Sep. 2010, submitted as Exhibit 1053 in Inter Partes Review Case Nos. IPR2015-00643, IPR2015-00644 and IPR2015-00830.
Rebif® (interferon beta-1a), Product Label, Jun. 2005, submitted as Exhibit 1059 in IPR2015-00643, Exhibit 1060 in Inter Partes Review Case No. IPR2015-00644 and Exhibit 1054 in Inter Partes Review Case No. IPR2015-00830.
Jacobs at al., (2000) "Intramuscular interferon beta-1a therapy initiated during a first demyelinating . . . " The New England Journal of Medicine, vol. 343, No. 13, pp. 898-904, submitted as Exhibit 1054 in Inter Partes Review Case Nos. IPR2015-00643 and IPR2015-00644.
Stedman's Medical Dictionary for Health Professionals and Nursing, sixth edition (2008), submitted as Exhibit 1055 in Inter Partes Review Case Nos. IPR2015-00643 and IPR2015-00644.

U.S. Pat. No. 3,849,550, issued Nov. 19, 1974 (Teitelbaum et al.), submitted as Exhibit 1055 in Inter Partes Review Case Nos. IPR2015-00643 and IPR2015-00644.
U.S. Patent Application Publication No. US 2009-0149541 A1, published Jun. 11, 2009 (Stark et al.), submitted as Exhibit 1056 in Inter Partes Review Case Nos. IPR2015-00643 and IPR2015-00644 and IPR2015-00830.
Copaxone®, Food and Drug Administration Approved Labeling, Jan. 2014, submitted as Exhibit 1057 in Inter Partes Review Case No. IPR2015-00643.
DiPiro et al., Concepts in clinical pharmacokinetics, Fifth Edition, in Introduction to Pharmacokinetics and Pharmacodynamics, American Society of Health-System Pharmacists® (2010), submitted as Exhibit 1062 in IPR2015-00643, and Exhibit 1057 in Inter Partes Review Case Nos. IPR2015-00644 and IPR2015-00830.
Multiple Sclerosis All about MS [online], Apr. 11, 2008 [retrieved on Feb. 5, 2015]. Retrieved from the Internet: <URL:scamparoo. wordpress.com/2008/04/11/ms-therapies-copaxone/>, submitted as Exhibit 1058 in Inter Partes Review Case No. IPR2015-00643, and Exhibit 1062 in Inter Partes Review Case Nos. IPR2015-00644.
M. Tintore et al., Baseline MRI predicts future attacks and disability in clinically isolated syndromes, 67 Neurology 968-972, (2006), submitted as Exhibit 1058 in Inter Partes Review Case No. IPR2015-00644.
Guidance for Industry Population Pharmacokinetics, Food and Drug Administration, Feb. 1999, submitted as Exhibit 1063 in IPR2015-00643 and Exhibit 1059 in Inter Partes Review Case Nos. IPR2015-00644 and IPR2015-00830.
U.S. Patent Application Publication No. US 2013-0165387 A1, published Jun. 27, 2013 (Klinger), submitted as Exhibit 1060 in Inter Partes Review Case Nos. IPR2015-00830.
Orange Book: Approved Drug Products with Therapeutic Equivalence Evaluations [online], accessdata.fda.gov [retrieved on Jan. 29, 2015]. Retrieved from the Internet: <URL://www.accessdata.fda. gov/scripts/cder/ob/docs/patexclnew.cfm?Appl_No=020622 &Product_No=003&table1=OB_Rx>, submitted as Exhibit 1060 in Inter Partes Review Case No. IPR2015-00643 and Exhibit 1061 in Inter Partes Review Case No. IPR2015-00644.
P.M. Rothwell et al. Doctors and Patients don't agree: cross sectional study of patients' and doctors' perceptions and assessments of disability in multiple sclerosis 314 The BMJ 1580 (May 31, 1997), submitted as Exhibit 1061 in Inter Partes Review Case No. IPR2015-00643.
Amendment in Response to Feb. 14, 2012 Office Action and Summary of May 8, 2012 Examiner Interview Pursuant to 37 C.F.R. § 1.133(b), filed in connection with U.S. Appl. No. 13/308,299, submitted as Exhibit 1064 in Inter Partes Review Case No. IPR2015-00643.
Redacted Expert Report of Ari Green, M.D., dated Apr. 19, 2016, which was prepared in connection with In Re Copaxone 40 Mg Cases, Case No. 1:14-cv-1171-GMS (Consolidated) in the United States District Court for District of Delaware.
Redacted Opening Expert Report of Andrew R. Pachner, Ph.D., dated Apr. 19, 2016, which was prepared in connection with In Re Copaxone 40 Mg Cases, Case No. 1:14-cv-1171-GMS (Consolidated) in the United States District Court for District of Delaware.
Redacted Opening Expert Report of Samuel J. Pleasure, M.D., Ph.D., dated Apr. 19, 2016, filed in connection with In Re Copaxone 40 Mg Cases, Case No. 1:14-cv-1171-GMS (Consolidated) in the United States District Court for District of Delaware.
Joint Claim Construction Chart, which is dated and filed on Aug. 14, 2015 in connection with In Re Copaxone 40 Mg Cases, Case No. 1:14-cv-1171-GMS (Consolidated) in the United States District Court for District of Delaware.
Second Declaration of Edward J. Fox, M.D., Ph.D., dated and filed on Oct. 2, 2015 in connection with In Re Copaxone 40 Mg Cases, Case No. 1:14-cv-1171-GMS (Consolidated) in the United States District Court for District of Delaware.
Second Declaration of Andrew R. Pachner, M.D., dated and filed on OCt. 2, 2015 in connection with In Re Copaxone 40 Mg Cases, Case No. 1:14-cv-1171-GMS (Consolidated) in the United States District Court for District of Delaware.

(56) References Cited

OTHER PUBLICATIONS

Defendant's Responsive Claim Construction Brief, dated and filed on Oct. 2, 2015 in connection with In Re Copaxone 40 Mg Cases, Case No. 1:14-cv-1171-GMS (Consolidated) in the United States District Court for District of Delaware.
Third Declaration of Edward J. Fox, M.D., Ph.D., dated and filed on Dec. 18, 2015 in connection with In Re Copaxone 40 Mg Cases, Case No. 1:14-cv-1171-GMS (Consolidated) in the United States District Court for District of Delaware.
Declaration of Samuel J. Pleasure, M.D., Ph.D., dated and filed on Dec. 18, 2015 in connection with In Re Copaxone 40 Mg Cases, Case No. 1:14-cv-1171-GMS (Consolidated) in the United States District Court for District of Delaware.
Defendant's Opening Claim Construction Brief Regarding U.S. Pat. No. 9,155,776, dated and filed on Dec. 18, 2015 in connection with In Re Copaxone 40 Mg Cases, Case No. 1:14-cv-1171-GMS (Consolidated) in the United States District Court for District of Delaware.
Plaintiff's Supplemental Opening Claim Construction Brief, dated and filed on Dec. 18, 2015 in connection with In Re Copaxone 40 Mg Cases, Case No. 1:14-cv-1171-GMS (Consolidated) in the United States District Court for District of Delaware.
Fourth Declaration of Edward J. Fox, M.D., Ph.D., dated and filed on Jan. 8, 2016 in connection with In Re Copaxone 40 Mg Cases, Case No. 1:14-cv-1171-GMS (Consolidated) in the United States District Court of Delaware.
Defendant's Reply Claim Construction Brief Regarding U.S. Pat. No. 9,155,776, dated and filed on Jan. 8, 2016 in connection with In Re Copaxone 40 Mg Cases, Case No. 1:14-cv-1171-GMS (Consolidated) in the United States District Court for District of Delaware.
Plaintiff's Supplemental Supplemental Answering Claim Construction Brief, dated and filed on Jan. 8, 2016 in connection with In Re Copaxone 40 Mg Cases, Case No. 1:14-cv-1171-GMS (Consolidated) in the United States District Court for District of Delaware.
Order Construing the Terms of U.S. Pat. Nos. 8,232,250, 8,399,413, 8,969302, and 9,155,776, issued on Mar. 7, 2016 in connection with In Re Copaxone 40 Mg Cases, Case No. 1:14-cv-1171-GMS (Consolidated) in the United States District Court for District of Delaware.
Stipulation and (Proposed) Order Concerning Claim Construction Dispute dated Feb. 10, 2016 and issued on Feb. 12, 2016 in connection with In Re Copaxone 40 Mg Cases, Case No. 1:14-cv-1171-GMS (Consolidated) in the United States District Court for District of Delaware.
Feb. 16, 2016 Petition for Post Grant Review of U.S. Patent No. 9,155,776 in the United States Patent and Trademark Office Patent Trial and Appeal Board (Case No. PGR2016-00010).
Expert Declaration of Ari Green, M.D. in Support of Petition for Post-Grant Review of U.S. Pat. No. 9,155,776, dated Feb. 7, 2016, submitted as Exhibit 1003 in Post Grant Review Case No. PGR2016-00010.
A Study in Subjects with Relapsing-Remitting Multiple Sclerosis (RRMS) to Assess the Efficacy, Safety and Tolerability of Glatiramer Acetate (GA) Injection 40 mg Administered Three Times a Week Compared to Placebo (GALA), NCT01067521 [online]. ClinicalTrials.gov [retrieved on Feb. 5, 2016]. Retrieved from the Internet: <URL:clinicaltrials.gov/ct2/show/NCT01067521>, submitted as Exhibit 1004 in Post Grant Review Case No. PGR2016-00010.
Safety and Tolerability of Glatiramer Acetate (GLACIER), NCT01874145 [online], ClinicalTrials.gov [retrieved on Feb. 5, 2016]. Retrieved from the Internet: <URL:clinicaltrials.gov/ct2/show/NCT01874145>, submitted as Exhibit 1005 in Post Grant Review Case No. FGR2016-00010.
Plaintiffs' Supplemental Opening Claim Construction Brief, In re Copaxone 40 mg Consolidated Cases, No. 1:14-cv-01171-GMS (D.Del), dated Dec. 18, 2015, submitted as Exhibit 1006 in Post Grant Review Case No. PGR2016-00010.

Citizen Petition Requesting That FDA Refrain from Approving any Abbreviated New Drug Application Referencing Copaxone® (glatiramer acetate injection) Until Certain Conditions Are Met, dated Jul. 2, 2014, filed with U.S. Food and Drug Administration, submitted as Exhibit 1009 in Post Grant Review Case No. PGR2016-00010.
Citizen Petition Requesting that FDA Consider New Scientific Information and Refrain from Approving Any Abbreviated New Drug Application Referencing Copaxone® (glatiramer acetate injection) Until Certain Conditions Are Met, dated Mar. 31, 2015, filed with U.S. Food and Drug Administration, submitted as Exhibit 1010 in Post Grant Review Case No. PGR2016-00010.
Kate McKeage, "Glatiramer Acetate 40 mg/mL in Relapsing-Remitting Multiple Sclerosis: A Review", CNS Drugs, Apr. 24, 2015, submitted as Exhibit 1011 in Post Grant Review Case No. PGR2016-00010.
Copaxone®, Food and Drug Administration Approved Labeling, Jan. 2014, submitted as Exhibit 1012 in Post Grant Review Case No. PGR2016-00010.
Defendant's Opening Claim Construction Brief Regarding U.S. Pat. No. 9,155,776, dated Dec. 18, 2015, In re Copaxone 40 mg Consolidated Cases, No. 1:14-cv-01171-GMS (D.Del.), submitted as Exhibit 1013 in Post Grant Review Case No. PGR2016-00010.
Plaintiff's Opening Claim Construction Brief, dated Sep. 11, 2015, In re Copaxone 40 mg Consolidated Cases, No. 1:14-cv-01171-GMS (D.Del.), submitted as Exhibit 1014 in Post Grant Review Case No. PGR2016-00010.
Yeda's Preliminary Patent Owner Response, dated May 26, 2015, for Case No. IPR2015-00643, submitted as Exhibit 1015 in Post Grant Review Case No. PGR2016-00010.
Deposition of Tjalf Ziemssen, dated Feb. 2, 2016, submitted as Exhibit 1016 in Post Grant Review Case No. PGR2016-00010.
Giancarlo Comi, et al., Phase III Dose-Comparison Study of Glatiramer Acetate for Multiple Sclerosis, Ann. Neurol. 2011; 69:75-82 (2011), submitted as Exhibit 1017 in Post Grant Review Case No. PGR2016-00010.
Teva Announces Top-line Results from GALA Phase III Trial Evaluating a New Dosage for Glatiramer Acetate Given Three Times Weekly for Relapsing-Remitting Multiple Sclerosis, [online]. [retrieved on Feb. 5, 2016]. Retrieved from the Internet: <URL: www.tevapharm.com/news/tevaannounces_top_line_results_from_gala_phase_iii_trial_evaluating_a_new_dosage_for_glatiramer_acetate_given_three_times_weekly_for_relapsing_remitting_multiple_sclerosis_06_12.aspx>, submitted as Exhibit 1018 in Post Grant Review Case No. PGR2016-00010.
Wolinsky et al. "Reduced frequency severity of injection site reactions with glatiramer acetate 40mg/mL three times weekly dosing" presented at the Joint Americas Committee for Treatment and Research in Multiple Sclerosis (ACTRIMS) European Committee for Treatment of Research in Multiple Sclerosis (ECTRIMS), Boston, MA, Sep. 10-13, 2014, poster, submitted as Exhibit 1019 in Post Grant Review Case No. PGR2016-00010.
Deposition of Edward J. Fox, M.D., dated Jan. 26, 2016, submitted as Exhibit 1020 in Post Grant Review Case No. PGR2016-00010.
Stipulation, In re Copaxone 40 mg Consolidated Cases, No. 1:14-cv-01171-GMS (D. Del.) (ECF No. 190), dated Feb. 10, 2016, submitted as Exhibit 1021 in Post Grant Review Case No. PGR2016-00010.
Plaintiffs' Opening Claim Construction Brief, In re Copaxone 40 mg Consolidated Cases, No. 1:14-cv-01171-GMS (D. Del.) (ECF No. 91), dated Sep. 11, 2015, submitted as Exhibit 1023 in Post Grant Review Case No. PGR2016-00010.
Yeda's Patent Owner Response, dated Nov. 20, 2015, for IPR2015-00643, submitted as Exhibit 1024 in Post Grant Review Case No. PGR2016-00010.
Yeda's Patent Owner Response, dated Nov. 20, 2015, for IPR2015-00644, submitted as Exhibit 1025 in Post Grant Review Case No. PGR2016-00010.
Yeda's Patent Owner Response, dated Nov. 25, 2015, for IPR2015-00830, submitted as Exhibit 1026 in Post Grant Review Case No. PGR2016-00010.

(56) References Cited

OTHER PUBLICATIONS

Miller, The Importance of Early Diagnosis of Multiple Sclerosis, J.Managed Care Pharmacy 10:S4-S11 (Jun. 2004), submitted as Exhibit 1027 in Post Grant Review Case No. PGR2016-00010.

Thomas M. Stewart, Injectable Multiple Sclerosis Medications: A Patient Survey of Factors Associated with Injection-Site Reactions, 14 Int'l J. MS Care 46, 48 (2012), submitted as Exhibit 1028 in Post Grant Review Case No. PGR2016-00010.

Pelidou et al., Multiple sclerosis presented as clinically isolated syndrome: the need for early diagnosis and treatment, Ther. Clin. Risk Management 4:627-30 (Jun. 2008), submitted as Exhibit 1029 in Post Grant Review Case No. PGR2016-00010.

Lynn McEwan et al., Best Practices in Skin Care for the Multiple Sclerosis Patient Receiving Injectable Therapies, 12 Int'l J. MS Care 177, 187 (2010), submitted as Exhibit 1030 in Post Grant Review Case No. PGR2016-00010.

Barry Singer et al., Comparative Injection-site Pain and Tolerability of Subcutaneous Serum-free Formulation of Interferonβ-1a Versus Subcutaneous interferonβ-1b: Results of the Randomized, Multicenter, Phase IIIb Reforms Study, 12 BMC Neurology, Dec. 2012, submitted as Exhibit 1031 in Post Grant Review Case No. PGR2016-00010.

U.S. Department of Health and Human Services, Common Terminology Criteria for Adverse Events (CTCAE) Version 4.0, published May 28, 2009, submitted as Exhibit 1032 in Post Grant Review Case No. PGR2016-00010.

Frohman, Multiple Sclerosis—The Plaque and its Pathogenesis, New England J.Med. 354:942-55 (2006), submitted as Exhibit 1033 in Post Grant Review Case No. PGR2016-00010.

Haines et al., Linkage of te MHC to familial multiple sclerosis suggests genetic heterogeneity. The multiple sclerosis genetics group, Hum.Mol. Genet. 7:1229-34 (1998), submitted as Exhibit 1034 in Post Grant Review Case No. PGR2016-00010.

Comi et al., European/Canadian multicenter, double-blind, randomized, placebo-controlled study of the effects of glatiramer acetate on magnetic resonance imaging measured disease activity and burden in patients with relapsing multiple sclerosis, Annals Neurol. 49:290-297 (2001), submitted as Exhibit 1035 in Post Grant Review Case No. PGR2016-00010.

Ge et al., Glatiramer acetate (Copaxone) treatment in relapsing-remitting MS, Quantitative MR assessment, Neurol. 54:813-17 (Feb. 2000), submitted as Exhibit 1036 in Post Grant Review Case No. PGR2016-00010.

Soares et al., Localized panniculitis secondary to subcutaneous glatiramer acetate injections for the treatment of multiple sclerosis: a clinicopathologic and immunohistochemical study, J. Am. Acad. Derm. 55:968-74 (2006), submitted as Exhibit 1037 in Post Grant Review Case No. PGR2016-00010.

Jerry S. Wolinsky et al., GLACIER: An Open-Label, Randomized, Multicenter Study to Assess the Safety and Tolerability of Glatiramer Acetate 40 MG Three-Times Weekly Versus 20 MG Daily in Patients with Relapsing-Remitting Multiple Sclerosis, 4 Multiple Sclerosis & Related Disorders 370, 371 (2015), submitted as Exhibit 1038 in Post Grant Review Case No. PGR2016-00010.

Rich et al., Stepped-care approach to treating MS: A managed care treatment algorithm, J.Managed Care Pharm. 10(3) (Suppl. S-b) :S26-S32 (Jun. 2004), submitted as Exhibit 1039 in Post Grant Review Case No. PGR2016-00010.

Bakshi et al., Imaging of multiple sclerosis: Role in neurotherapeutics, J. Am, Soc. Exper. Neurotherapeutics 2:277-303 (Apr. 2005), submitted as Exhibit 1040 in Post Grant Review Case No. PGR2016-00010.

Stuart, Clinical management of multiple sclerosis: The treatment paradigm and issues of patient management, J. Managed Care Pharmacy 10(3) (Suppl. S-b) :S19-S25 (Jun. 2004), submitted as Exhibit 1041 in Post Grant Review Case No. PGR2016-00010.

Edgar et al., Lipoatrophy in patients with multiple sclerosis on glatiramer acetate, Canadian J. Neurol. Sci. 31:58-63 (2004), submitted as Exhibit 1042 in Post Grant Review Case No. PGR2016-00010.

Johnson et al., Copolymer 1 reduces relapse rate and improves disability in relapsing-remitting multiple sclerosis, Neurology 454:1268-76 (1995), submitted as Exhibit 1043 in Post Grant Review Case No. PGR2016-00010.

Betaseron® Product Label (Oct. 2003), Berlex Laboratories, submitted as Exhibit 1044 in Post Grant Review Case No. PGR2016-00010.

Rebif® (interferon beta-1a) Product Label, Jun. 2015, Pfizer Inc., submitted as Exhibit 1045 in Post Grant Review Case No. PGR2016-00010.

Avonex® (Interferon beta-1a) Product Label, Feb. 2007, Biogen Idec Inc., submitted as Exhibit 1046 in Post Grant Review Case No. PGR2016-00010.

Interferon Beta 1b (Extavia®), Abbreviated National Drug Monograph, published Sep. 2010 by VA Pharmacy Benefits Management Services, Medical Advisory Panel and VISN Pharmacist Executives, submitted as Exhibit 1047 in Post Grant Review Case No. PGR2016-00010.

Tysabri® Product Label (Oct. 2008), Biogen Idec Inc., submitted as Exhibit 1048 in Post Grant Review Case No. PGR2016-00010.

Patent Owner Yeda Research & Development Co. Ltd.'s Preliminary Response, dated May 24, 2016, which was filed on May 24, 2016 in connection with *Mylan Pharmaceuticals Inc.* v. *Yeda Research & Development Co. Ltd.*, Post Grant Review of U.S. Pat. No. 9,155,776 in the United States Patent and Trademark Office Patent Trial and Appeal Board (Case No. PGR2016-00010).

Declaration of Edward J. Fox, M.D., Ph.D. in Support of Patent Owner Yeda's Preliminary Response, dated May 23, 2016, which was filed on May 24, 2016 as Exhibit 2001 in connection with *Mylan Pharmaceuticals Inc.* v. *Yeda Research & Development Co. Ltd.*, Post Grant Review of U.S. Pat. No. 9,155,776 in the United States Patent and Trademark Office Patent Trial and Appeal Board (Case No. PGR2016-00010).

U.S. Appl. No. 61/274,687, filed Aug. 20, 2009 submitted as Exhibit 2002 on May 24, 2016 in Post Grant Review Case No. PGR2016-00010.

Claim Chart of U.S. Pat. No. 9,155,776, issued Oct. 13, 2015 submitted as Exhibit 2003 on May 24, 2016 in Post Grant Review Case No. PGR2016-00010.

U.S. Appl. No. 13/770,677, filed Feb. 19, 2013 and Preliminary Amendment dated Feb. 19, 2013 filed in connection with U.S. Appl. No. 13/770,677, filed Feb. 19, 2013, submitted together as Exhibit 2004 on May 24, 2016 in Post Grant Review Case No. PGR2016-00010.

Defendant's Initial Joint Invalidity Contentions Regarding U.S. Pat. No. 9,155,776 B2, which was filed in connection with In Re Copaxone 40 Mg Cases, Case No. 1:14-cv-1171-GMS (Consolidated) in the United States District Court for District of Delaware, submitted as Exhibit 2005 on May 24, 2016 in Post Grant Review Case No. PGR2016-00010.

U.S. Appl. No. 12/806,684, filed Aug. 19, 2010 and Preliminary Amendment dated Aug. 19, 2010 filed in coneection with U.S. Appl. No. 12/806,684, filed Aug. 19, 2010, submitted together as Exhibit 2006 on May 24, 2016 in Post Grant Review Case No. PGR2016-00010.

U.S. Appl. No. 61/337,612, filed Feb. 11, 2010, submitted as Exhibit 2007 on May 24, 2016 in Post Grant Review Case No. PGR2016-00010.

Khan et al., "Three Times Weekly Glatiramer Acetate in Relapsing-Remitting Multiple Sclerosis," Ann. Neural., 2013; 73:705-713, submitted as Exhibit 2008 on May 24, 2016 in Post Grant Review Case No. PGR2016-00010.

Business Wire, "Teva Announces Top-Line Results from GALA Phase III Trial Evaluating a New Dosage for Glatiramer Acetate Given Three Times Weekly for Relapsing-Remitting Multiple Sclerosis," dated Jun. 14, 2012, submitted as Exhibit 2009 on May 24, 2016 in Post Grant Review Case No. PGR2016-00010.

Reuters Press Release, "New Data Presente at the 28th ECTRIMS Congress Showcase Teva's Ongoing Commitment to Multiple Sclerosis Research," dated Oct. 8, 2012, submitted as Exhibit 2010 on May 24, 2016 in Post Grant Review Case No. PGR2016-00010.

Khan et al., "A phase 3 trial to assess the efficacy and safety of glatiramer acetate injections 40 mg administered 3 times a week

(56) References Cited

OTHER PUBLICATIONS compared to placebo," Abstract 166, Multiple Sclerosis Journal 2012; 18(54)509-520, submitted as Exhibit 2011 on May 24, 2016 in Post Grant Review Case No. PGR2016-00010.
U.S. Appl. No. 14/630,326, filed Feb. 24, 2015, and Application Data Sheet dated Feb. 24, 2015 and Preliminary Amendment dated Feb. 24, 2015, filed in connection with U.S. Appl. No. 14/630,326, filed Feb. 24, 2015, submitted together as Exhibit 2012 on May 24, 2016 in Post Grant Review Case No. PGR2016-00010.
Cobert, et al., "Practical Drug Safety from A to Z," Jones and Bartlett Publishers, 2009, pp. 327-329, submitted as Exhibit 2013 on May 24, 2016 in Post Grant Review Case No. PGR2016-00010.
World Health Organization, "A Practical Handbook on the Pharmacovigilance of Antiretroviral Medicines," 2009, 129-133, submitted as Exhibit 2014 on May 24, 2016 in Post Grant Review Case No. PGR2016-00010.
Patent Owner's Exhibit List, dated May 24, 2016, submitted as Exhibit 2000 on May 24, 2016 in Post Grant Review Case No. PGR2016-00010.
Decision Denying Institution of Post Grant Review issued on Aug. 15, 2016 by the United States Patent and Trademark Office Patent Trial and Appeal Board (Case No. PGR2016-00010).
Written Opinion of the International Searching Authority dated Dec. 21, 2015 in connection with PCT International application No. PCT/US2015/051203.
International Search Report dated Dec. 21, 2015 in connection with PCT International application No. PCT/US2015/051203.
Patent Examination Report No. 1 issued Aug. 18, 2016 by IP Australian in connecion with Australian Patent Application No. 2015380381.
Innovation Patent Examination Report No. 1 issued Oct. 6, 2016 by IP Australia in connection with Australian Patent Application No. 2016101453.
Communication regarding the extended European search report dated on Nov. 20, 2015 by the European Patent Office in connection with European Patent Application No. 15186721.5.
Corning Inc., "Corning Filtration Guide" [online], 2013, XP002750000 [retrieved on Nov. 2, 2015]. Retrieved from the internet: <URL:csmedia2.corning.com/lifesciences/media/pdf/t_filterselectionguide.pdf>.
Dec. 7, 2015 Information on Oral Proceedings issued by the European Patent Office in connection with Opposition filed against EP2405749B.
U.S. Patent Application Publication No. 2007-0161566, published Jul. 12, 2007 (Pinchasi), submitted as Exhibit D1 of Opposition filed against EP2405749B.
Fletcher et al., "Comparison of glatiramer acetate (Copaxone®) and interferon β-1b (Betaferon®) in multiple sclerosis patients: an open-label 2-year follow-up" J. Neural Sci vol. 197, pp. 51-55, submitted as Exhibit D2 of Opposition filed against EP2405749B.
Fletcher et al., "Copolymer 1 (Glatiramer Acetate) in Relapsing Forms of Multiple Sclerosis: Open Multicenter Study of Alternate-Day Adnlinistration" Clin Neuropharm 2002, vol. 25(1), pp. 11-15, submitted as Exhibit D3 of Opposition filed against EP2405749B.
Khan et al., Randomized, prospective, rater-blinded, four-year, pilot study to compare the effect of daily versus every-other-day glatiramer acetate 20 mg subcutaneous injections in relapsing-remitting multiple sclerosis Multiple Sclerosis 2008, vol. 14, S295, submitted as Exhibit D4 of Opposition filed against EP2405749B.
Simpson et al., "Glatiramer Acetate: A review of its Use in relapsing-Remitting Multiple Sclerosis" Adis Drug Evaluation, Glatiramer Acetate, 2002, submitted as Exhibit D7 of Opposition filed against EP2405749B.
"News Release, Teva to Present Positive Data for Glatiramer Acetate 40 mg/1ml Given Three Times Weekly for Relapsing-Remitting MS" [online] Teva Pharmaceutical Industries Ltd. Oct. 10, 2012 [retrieved on Apr. 2, 2013]. Retrieved from the Internet: <URL://www.tevapharm.com/Media/News/Pages/2012/1743500.aspx?year=2012&page . . . >, submitted as Exhibit D9 of Opposition filed against EP2405749B.

Kahn et al, "Late Breaking News II: A phase 3 trial to assess the efficacy and Safety of glatiramer acetate injections 40mg administered 3 times a week compared to placebo", abstract presented on Oct. 13, 2012 at the 28th Congress of the European Committee for Treatment and Research in Multiple Sclerosis held at Lyon France on Oct. 10-13, 2012, submitted as Exhibit D10 of Opposition filed against EP2405749B.
"Copaxone 20mg/ml, Solution for Injection, Pre-filled Syringe" [online] Teva Pharmaceutical Ltd., Feb. 3, 2009 [retrieved on Jan. 27, 2013], Retrieved from the Internet: <URL://www.medicines.org.uk/EMC/printfriendlydocument.aspx?documentid=17516>>, submitted as Exhibit D11 of Opposition filed against EP2405749B.
PCT International Application Publication No. WO 2005/00120542, Published Dec. 22, 2005 (Rasmussen at al.), submitted as Exhibit D12 of Opposition filed against EP2405749B.
US Application Publication No. 2005-0014696, published Jan. 20, 2005 (Yong et al.), submitted as Exhibit D13 of Opposition filed against EP2405749B.
US Application Publication No. 2009-0149541, published Jun. 11, 2009 (Stark et al.), submitted as Exhibit D14 of Opposition filed against EP2405749B.
Yong et al. "Immunological response to different doses of GA in MS: Analyses from the FORTE trial" dated Apr. 28 2009, Abstract only, submitted as Exhibit D15 of Opposition filed against EP2405749B.
Jul. 1, 2009 Response to Apr. 2, 2009 Final Office Action filed with the U.S. Patent and Trademark Office in connection with U.S Appl. No. 11/651,212, submitted as Exhibit D16 of Opposition filed against EP2405749B.
Comi et al. "Results from a phase III, 1-year, Randomized, Double-blind, Parallel-Group, Dose Comparison Study with Glatiramer Acetate in Relapsing-remitting Multiple Sclerosis", abstract at the World Congress on Treatment and Research in Multiple Sclerosis—Montreal 2008, presented on Sep. 20, 2008, [online] [retrieved on Aug. 21, 2015]. Retrieved from the Internet: <URL://www.multiwebcast.com/wctrims/2008/msmontreal/2448/chair.giancarlo.comi.r . . . >submitted as Exhibit D19 of Opposition filed against EP2405749B.
Slides of G. Comi, Forte: Results from a phase II, 1-year, Randomized, Double-blind, Parallel-Group, Dose Comparison Study with Glatiramer Acetate in Relapsing-remitting Multiple Sclerosis, Presented at World Congress on Treatment and Research in Multiple Sclerosis: 2008 Joint Meeting of the American, European, and Latin America Committees on Treatment and Research in Multiple Sclerosis, San Raffaele, Italy (ACTRIMS, ECTRIMS, LACTRIMS) (2008), submitted as Exhibit D19a of Opposition filed against EP2405749B.
"Medscape Medical News: Doubling the Dose of Glatiramer Acetate Does Not Increase Efficacy" [online] Medscape, Sep. 22, 2008, [retrieved on Jan. 6, 2015], Retrieved from the Internet: <URL://www.medscape.com/viewartice/580865>, submitted as Exhibit D23 of Opposition filed against EP2405749B.
"Daily News: High-dosage Copaxone trial results are bad news for Teva" [online] PharmaTimes, Jul. 7, 2008, [retrieved on Nov. 6, 2015]. Retrieved from the Internet: <URL://http://www.pharmatimes.com/article/08-07-07/High-dosage_Copaxone_trial_results_. . . >, submitted as Exhibit D24 of Opposition filed against EP2405749B.
Committee for Medicinal Products for Human Use (CHMP) "Guidelines on Clinical Investigation of Medicinal Products for the Treatment of Multiple Sclerosis", European Medicines Agency, Nov. 16, 2006, submitted as Exhibit D25 of Opposition filed against EP2405749B.
Varkoni et al. "The glatiramoid class of immunomodulator Drugs" Expert Opinion on Pharmacotherapy 2009 10(4) 657-668, submitted as Exhibit D26 of Opposition filed against EP2405749B.
McKeage "Glatiramer Acetate 40 mg/mL in Relapsing-Remitting Multiple Sclerosis: A Review" ADIS Drug Evaluation, Apr. 2015, submitted as Exhibit D28 of Opposition filed against EP2405749B.
Wolinski "Reduced frequency severity of injection site reactions with glatiramer acetate 40mg/mL three times weekly dosing" ECTRIMS/ECTRIMS Conference, 10-13 Sep. 2014, poster, submitted as Exhibit D29 of Opposition filed against EP2405749B.

(56) References Cited

OTHER PUBLICATIONS

Approval procedure for Copaxone in the US, file No. NDA 20-622, submitted as Exhibit D34 of Opposition filed against EP2405749B.
Statement of Grounds for Appeal against the decision of the Opposition Division dated Jan. 19, 2016 to maintain EP 2405749, filed by Generics [UK] Limited Co., Ltd on May 29, 2016 with the European Patent Office in connection with an appeal filed against EP2405749B (Appeal No. T0599/16-3.3.04).
Grounds of Appeal filed by Synthon BV on May 23, 2016 with the European Patent Office in connection with an appeal filed against EP2405749B (Appeal No. T0599/16-3.3.04).
Grounds of appeal filed by Actavis Group ehf on May 30, 2016 with the European Patent Office in connection with an appeal filed against EP2405749B (Appeal No. T0599/16-3.3.04).
U.S. Appl. No. 61/274,687, filed Aug. 20, 2009, submitted as Exhibit D36 with the European Patent Office in connection with an appeal filed against EP2405749B (Appeal No. T0599/16-3.3.04).
View of CNCT01067521 on Feb. 10, 2010 [online]. ClinicalTrials.gov, 1993 [retrieved on Jan. 19, 2016]. Retrieved from the Internet: <URL: clinicaltrials.gov/archive/NCT01067521/2010 02 10>, submitted as Exhibit D37 with the European Patent Office in connection with an appeal filed against EP2405749B (Appeal No. T0599/16-3.3.04).
Shi et al., Impact of dose frequency on compliance and health outcomes: a literature review (1966-2006), Expert Rev Pharmacoeconomics Outcomes Res 2007 7(2) 187-202, submitted as Exhibit D38 with the European Patent Office in connection with an appeal filed against EP2405749B (Appeal No. T0599/16.3.3.04).
Costello et al., Recognizing Nonadherence in Patients with Multiple Sclerosis and Maintaining Treatment Adherence in the Long Term, Medscape J Med 2008 10(9) 225, submitted as Exhibit D39 with the European Patent Office in connection with an appeal filed against EP2405749B (Appeal No. T0599/16-3.3.04).
Koch J., Product Life-Cycle Management for Injectable Drugs: A Good Outlook for Proactive Market Players [online]. Pharmatech.com, Dec. 2, 2006 [retrieved on Jan. 15, 2016]. Retrieved from the Internet: <URL:pharmtech.com/print/235072?page=full>, submitted as Exhibit D40 with the European Patent Office in connection with an appeal filed against EP2405749B (Appeal No. T0599/16-3.3.04).
Rovaris M et al. Abstract P570, "Results of a randomized, double-blind, parallel-group study assessing safety and efficacy of 40mg vs. 20mg of glatiramer acetate on MRI-measured disease activity in relapsing-remitting multiple sclerosis", abstract of Sixteenth Meeting of the European Neurological Society May 27-31, 2006, Lausanne, Switzerland, published in J Neurol (2006) 253 (Suppl. 2), submitted as Exhibit D41 with the European Patent Office in connection with an appeal filed against EP2405749B (Appeal No. T0599/16-3.3.04).
Declaration of John Owen King, May 20, 2016, submitted as Exhibit D42 with the European Patent Office in connection with an appeal filed against EP2405749B (Appeal No. T0599/16-3.3.04).
Polman et al., Diagnostic Criteria for Multiple Sclerosis: 2005 Revisions to the "McDonald Criteria", Ann Neurol. 2005 58 840-846, submitted as Exhibit D42-2 with the European Patent Office in connection with an appeal filed against EP2405749B (Appeal No. T0599/16-3.3.04).
MIMS Annual, Thirty Third Edition, Jun. 2009, pp. 10-1480 to 10-1482, 10-1456 to 10-1458, 10-1396 to 10-1400, 10-1406 to 10-1408 and 9-1206 to 9-1207, submitted as Exhibit D42-3 with the European Patent Office in connection with an appeal filed against EP2405749B (Appeal No. T0599/16-3.3.04).
Neuhaus et al., Mechanisms of action of glatiramer acetate in multiple sclerosis, Neurology 2001 56 702-708, submitted as Exhibit D42-4 with the European Patent Office in connection with an appeal filed against EP2405749B (Appeal No. T0599/16-3.3.04).
Khan et al., Three Times Weekly Glatiramer Acetate in Relapsing-Remitting Multiple Sclerosis, Ann Neurol 2013 73 705-713, submitted as Exhibit D42-5 and D46 with the European Patent Office in connection with an appeal filed against EP2405749B (Appeal No. T0599/16-3.3.04).
Devonshire et al., The Global Adherence Project—A Multicentre Observational Study on Adherence to Disease-Modifying Therapies in Patients Suffering from Relapsing-Remitting Multiple Sclerosis, Multiple Sclerosis 12:S1(P316) (2006), submitted as Exhibit D43 with the European Patent Office in connection with an appeal filed against EP2405749B (Appeal No. T0599/16-3.3.04)
Declaration of Pablo Villoslada, dated May 2, 2016, submitted as Exhibit D44 with the European Patent Office in connection with an appeal filed against EP2405749B (Appeal No. T0599/16-3.3.04).
Medication Guide Rebif® (Re-bif)—Interferon beta-1a, Mar. 2002, Serono, Inc., submitted as Exhibit D45 with the European Patent Office against in connection with an appeal filed EP2405749B (Appeal No. T0599/16-3.3.04).
Second Expert Report of Professor Wolfgang Brück, dated Oct. 9, 2016, submitted as Exhibit D47 with the European Patent Office in connection with an appeal filed against EP2405749B (Appeal No. T0599/16-3.3.04).
Second Expert Report of Dr Simon Day, dated Oct. 10, 2016, submitted as Exhibit D48 with the European Patent Office in connection with an appeal filed against EP2405749B (Appeal No. T0599/16-3.3.04).
Calabresi F., Investigating glatiramer acetate for relapsing-remitting multiple sclerosis at the double dose—is more better?, Nature Clinical Practice, Oct. 2007 540-541, submitted as Exhibit D49 with the European Patent Office in connection with an appeal filed against EP2405749B (Appeal No. T0599/16-3.3.04).
Manfredonia et al., Review of the clinical evidence for interferon β1a (Rebif®) in the treatment of multiple sclerosis, Neuropsychiatric Disease and Treatment 2008:4(2) 321-336, submitted as Exhibit D50 with the European Patent Office in connection with an appeal filed against EP2405749B (Appeal No. T0599/16-3.3.04).
Haas and Firzlaff, Twenty-four-month comparison of immunomodulatory treatments—a retrospective open label study in 308 ARMS patients treated with beta interferons or glatiramer acetate (Copaxone®), European J. of Neurology, 12, 425-31, 429 (2005), submitted as Exhibit D51 with the European Patent Office in connection with an appeal filed against EP2405749B (Appeal No. T0599/16-3.3.04).
Reply to the Grounds of Appeal, dated Oct. 10, 2016, filed by Yeda Research Development Co Ltd, with the European Patent Office in connection with an appeal filed against EP2405749B (Appeal No. T0599/16-3.3.04).
Mar. 9, 2016 Mylan's Reply to Yeda's Patent Owner Response filed in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).
Mar. 9, 2016 Mylan's Reply to Yeda's Patent Owner Response filed in connection with *Mylan Pharmaceuticals Inc.* v. *Yeda Research & Development Co. Ltd.* for U.S. Pat. No. 8,399,413 in the United States Patent and Trademark Office Patent Trial and Appeal Board (Case No. IPR2015-00644).
Mar 9, 2016 Mylan's Reply to Yeda's Patent Owner Response filed in connection with *Mylan Pharmaceuticals Inc.* v. *Yeda Research & Development Co. Ltd.* for U.S. Pat. No. 8,969,302 in the United States Patent and Trademark Office Parent Trial and Appeal Board (Case No. IPR2015-00830).
Expert Declaration of Ari Green, M.D. in Support of Petitioner's Reply to Patent Owner's Response, dated Mar. 9, 2016, submitted as Exhibit 1085 on Mar. 8, 2016 in Inter Partes Review Case Nos. IPR2015-00643, IPR2015-00644 and IPR2015-00830.
Declaration of Prof. Joel W. Hay (public version), dated Mar. 9, 2016, submitted as Exhibit 1099 on Mar. 22, 2016 in Inter Partes Review Case Nos. IPR2015-00643, IPR2015-00644 and IPR2015-00830.
Deposition Transcript of Joel W. Hay, Ph.D., which deposition took place on Apr. 4, 2016, submitted as Exhibit 1141 on Apr. 12, 2016 in Inter Partes Review Case Nos. IPR2015-00643, IPR2015-00644 and IPR2015-00830.

(56) References Cited

OTHER PUBLICATIONS

Deposition Transcript of Ari Green, M.D., which deposition took place on Apr. 4, 2016, submitted as Exhibit 1142 on Apr. 12, 2016 in Inter Partes Review Case Nos. IPR2015-00643, IPR2015-00644 and IPR2015-00830.

Deposition Transcript of Dr. Jerry S. Wolinsky (public version) taken in In re Copaxone 40 mg Consolidated Cases, No. 14-1171 (D. Del), which deposition took place on Feb. 15, 2016, submitted as Exhibit 1140 on Apr. 12, 2016 in Inter Partes Review Case Nos. IPR2015-00643, IPR2015-00644 and IPR2015-00830.

Deposition Transcript of Robert W. Gristwood, Ph.D., which deposition took place on Jan. 13, 2016, submitted as Exhibit 2145 on Mar. 1, 2016 in Inter Partes Review Case Nos. IPR2015-00643, IPR2015-00644 and IPR2015-00830.

Deposition Transcript of Edward J. Fox, M.D., which deposition took place on Jan. 26, 2016, submitted as Exhibit 2146 on Mar. 1, 2016 in Inter Partes Review Case Nos. IPR2015-00643, IPR2015-00644 and IPR2015-00830.

Deposition Transcript of Tjalf Ziemssen, which deposition took place on Feb. 2, 2016, submitted as Exhibit 2147 on Mar. 1, 2016 in Inter Partes Review Case Nos. IPR-2015-00643, IPR2015-00644 and IPR2015-00830.

Deposition Transcript, of Henry G. Grabowski, Ph.D., which deposition took place on Feb. 10, 2016, submitted as Exhibit 2148 on Mar. 7, 2016 in Inter Partes Review Case Nos. IPR2015-00643, IPR2015-00644 and IPR2015-00830.

O. Khan, et al., Glatiramer acetate 20mg subcutaneous twice—weekly versus daily injections: results of a pilot, prospective, randomised, and rater-blinded clinical and MRI 2-year study in relapsing-remitting multiple sclerosis, Multiple Sclerosis 2009; 15:S151-S269, S249-S250 (2009), submitted as Exhibit 1068 on Mar. 8, 2016 in Inter Partes Review Case Nos. IPR2015-00643, IPR2015-00644 and IPR2015-00830.

G. Pardo, et al., Impact of an oral antihistamine on local injection site reactions with glatiramer acetate, Multiple Sclerosis, 2007; 13:S7-S2753, S134 (2007), submitted as Exhibit 1069 on Mar. 8, 2016 in Inter Partes Review Case Nos. IPR2015-00643, IPR2015-00644 and IPR2015-00830.

S. Bains, et al., Glatiramer acetate: successful desensitazation for treatment of multiple sclerosis, Annals of Allergy, Asthma & Immunology, 2010;104:321-325, submitted as Exhibit 1070 on Mar. 8, 2016 in Inter Partes Review Case Nos. IPR2015-00643, IPR2015-00644 and IPR2015-00830.

E. Fisher, et al., Gray Matter Atrophy in Multiple Sclerosis: A Longitudinal Study, Annals of Neurology, 2008;64:255-265, submitted as Exhibit 1071 on Mar. 8, 2016 in Inter Partes Review Case Nos. IPR2015-00643, IPR2015-00644 and IPR2015-00830.

Fourth Declaration of Edward J. Fox, M.D., Ph.D., In re Copaxone 40 mg Consolidated Cases, Civil Action No. 1:14-cv-001171, ECF No. 155 (D. Del.) dated Jan. 8, 2016 together with Exhibits A-C, submitted as Exhibit 1072 on Mar. 8, 2016 in Inter Partes Review Case Nos. IPR2015-00643, IPR2015-00644 and IPR2015-00830.

G. Anderson, et al., Tolerability and safety of novel half milliliter formulate of glatiramer acetate for subcutaneous injection : an open-label, multicenter, randomized comparative study, Journal of Neurology (2010) 257:1917-1923, submitted as Exhibit 1073 on Mar. 8, 2016 in Inter Partes Review Case Nos. IPR2015-00643, IPR2015-00644 and IPR2015-00830.

G. Shaw, Exorbitant Drug Costs May Price Out Patients, The Washington Diplomat (Apr. 27, 2011), submitted as Exhibit 1074 on Mar. 8, 2016 in Inter Partes Review Case Nos. IPR2015-00643, IPR2015-00644 and IPR2015-00830.

T. Ziemssen, et al., A 2-year observational study of patients with relapsing-remitting multiple sclerosis converting to glatiramer acetate from other disease-modifying therapies: the Coptimize trial, Journal of Neurology (2014) 261:2101-2111, submitted as Exhibit 1079 on Mar. 8, 2016 in Inter Partes Review Case Nos. IPR2015-00643, IPR2015-00644 and IPR2015-00830.

T. Ziemssen, et al., Sub-analysis of geographical variations in the 2-year observational Coptimize trial of patients with relapsing-remitting multiple sclerosis converting to glatiramer acetate, BMC Neurology (2015) 15:189, submitted as Exhibit 1080 on Mar. 8, 2016 in Inter Partes Review Case Nos. IPR2015-00643, IPR2015-00644 and IPR2015-00830.

T. Ziemssen, et al., QualiCOP: An Open-Label, Prospective, Observational Study of Glatiramer Acetate in Patients with Relapsing-Remitting Multiple Sclerosis, submitted as Exhibit 1081 on Mar. 8, 2016 in Inter Partes Review Case Nos. IPR2015-00643, IPR2015-00644 and IPR2015-00830.

N. Kleiner, et al., Immunological Response to Glatiramer Acetate in MS Patients after Different Pretreatments—The CopImmunoNet Study, P06.178, A554 Neurology 74, Suppl 2 (Mar. 2, 2010), submitted as Exhibit 1082 on Mar. 8, 2016 in Inter Partes Review Case Nos. IPR2015-00643, IPR2015-00644 and IPR2015-00830.

Teva News Release, New Study Demonstrated Significant Reduction in Annualized Relapse Rate and Halting of Disability Progression in MS Patients Switching to Copaxone® (Apr. 14, 2011), submitted as Exhibit 1083 on Mar. 8, 2016 in Inter Partes Review Case Nos. IPR2015-00643, IPR2015-00644 and IPR2015-00830.

R. Aharoni, et al., Glatiramer acetate-specific T cells in the brain express T helper 2/3 cytokines and brain-derived neurotrophic factor in situ, PNAS 100(24):14157-14162 (Nov. 25, 2003), submitted as Exhibit 1084 on Mar. 8, 2016 in Inter Partes Review Case Nos. IPR2015-00643, IPR2015-00644 and IPR2015-00830.

Teva's Shared Solutions® How to Prepare for Your Injection, "Preparation" [online]. Teva Neuroscience [retrieved on Mar. 7, 2016]. Retrieved from the internet: <URL://www.copaxone.com/injection-assistance/preparing-your-injection.html>, submitted as Exhibit 1086 on Mar. 9, 2016 in Inter Partes Review Case Nos. IPR2015-00643, IPR2015-00644 and IPR2015-00830.

Louise Gagnon, "Every-Other-Day Dosing of Glatiramer Acetate Reduces Adverse Reactions with Comparable Efficacy to Daily Dosing: Presented at WCTRMS" [online]. Peerview Press, Sep. 21, 2008 [etrieved on Mar. 8, 2016]. Retrieved from the internet: <URL://peerviewpress.com/every-other-day-dosing-glatiramer-acetate-reduces-adverse-reactions-comparable-efficacy-daily-dosing-presented-wctrms>, submitted as Exhibit 1087 on Mar. 9, 2016 in Inter Partes Review Case Nos. IPR2015-00643, IPR2015-00644 and IPR2015-00830.

J. Wolinsky, Glatiramer acetate for the treatment of multiple sclerosis, Expert Opinion on Pharmacotherapy, 5(4):875-891 (2004), submitted as Exhibit 1088 on Mar. 9, 2016 in Inter Partes Review Case Nos. IPR2015-00643, IPR2015-00644 and IPR2015-00830.

O. Khan et al., Glatiramer acetate 20mg subcutaneous twice-weekly versus daily injections: results of a pilot, prospective, randomised, and rater blinded clinical and MRI 2-year study in relapsing-remitting multiple sclerosis, Multiple Sclerosis, 15:S151-S269 (2009), submitted as Exhibit 1089 on Mar. 9, 2016 in Inter Partes Review Case Nos. IPR2015-00643, IPR2015-00644 and IPR2015-00830.

M.S. Weber et al., Mechanism of Action of Glatiramer Acetate in Treatment of Multiple Sclerosis, Neurotherapeutics, 4(4):647-653 (2007), submitted as Exhibit 1090 on Mar. 9, 2016 in Inter Partes Review Case Nos. IPR2015-00643, IPR2015-00644 and IRP2015-00830.

W.F. Hickey et al., T-Lymphocyte Entry Into the Central Nervous System, J. of Neuroscience Research, 28(2):254-260 (1991), submitted as Exhibit 1091 on Mar. 9, 2016 in Inter Partes Review Case Nos. IPR2015-00643, IPR2015-00644 and IPR2015-00830.

T.M. Stewart et al., Injectable Multiple Sclerosis medications: A Patient Survey of Factors Associated with Injection-Site Reactions, Int'l J. MS Care, 14(1):46-53 (2012), submitted as Exhibit 1092 on Mar. 9, 2016 in Inter Partes Review Case Nos. IPR2015-00643, IPR2015-00644 and IPR2015-00830.

U.S. Dep't Health & Human Services., Common Terminology Criteria for Adverse Events (CTCAE) (Version 4.03 Jun. 14, 2010), published May 28, 2009, submitted as Exhibit 1093 on Mar. 9, 2016 in Inter Partes Review Case Nos. IPR2015-00643, IPR2015-00644 and IPR2015-00830.

B. Singer et al., Comparative injection-site pain and tolerability of subcutaneous serum-free formulation of interferonβ-1a versus subcutaneous interferonβ-1b: results of the randomized, multicenter, Phase IIIb Reforms study, BMC Neurology, 12:154 (2012), sub-

(56) References Cited

OTHER PUBLICATIONS mitted as Exhibit 1094 on Mar. 9, 2016 in Inter Partes Review Case Nos. IPR2015-00643, IPR2015-00644 and IPR2015-00830.
L. McEwan et al., Best Practices in Skin Care for the Multiple Sclerosis Patient Receiving Injectable Therapies, Int'l J. MS Care, 12:177-189 (2010), submitted as Exhibit 1095 on Mar. 9, 2016 in Inter Partes Review Case Nos. IPR2015-00643, IPR2015-00644 and IPR2015-00830.
R. Bermel et al., The measurement and clinical relevance of brain atrophy in multiple sclerosis, LANCET NEUROL., 5(2):158-70 (2006), submitted as Exhibit 1096 on Mar. 9, 2016 in Inter Partes Review Case Nos. IPR2015-00643, IPR2015-00644 and IPR2015-00830.
E. Fisher et al., Gray Matter Atrophy in Multiple Sclerosis: A Longitudinal Study, Ann. Neurol., 4:255-265 (2008), submitted as Exhibit 1097 on Mar. 9, 2016 in Inter Partes Review Case Nos. IPR2015-00643, IPR2015-00644 and IPR2015-00830.
Lauren LeBano, Gray Matter Atrophy May Serve as an Effective Outcome measure for MS Clinical Trials [online] Neurol. Reviews, 20(2):8 (2012) [retrieved on Mar. 8, 2016]. Retrieved from the internet: <URL://www.neurologyreviews.com/specialty-focus/multiple-sclerosis-ms/article/gray-matter-atrophy-may-serve-as-an-effective-outcome-measure-for-ms-clinical-trials/5flc2ba3adde725b8a583502b5c332e1.html?trendmd-shared=1>, submitted as Exhibit 1098 on Mar. 9, 2016 in Inter Partes Review Case Nos. IPR2015-00643, IPR2015-00644 and IPR2015-00830.
Xinke Zhang et al., Cost Effectiveness of Fingolimod, Teriflunomide, Dimethyl Fumarate and Intramuscular Interferon-β1a in Relapsing-Remitting Multiple Sclerosis, 29(1) CNS Drugs 71 (2015), submitted as Exhibit 11000 on Mar. 9, 2016 in Inter Partes Review Case Nos. IPR2015-00643, IPR2015-00644 and IPR2015-00830.
Matthew Herper, Inside The Secret World of Drug Company Rebates, Forbes Pharma & Healthcare [online] Forbes.com LLC™ 2015, [retrieved on Dec. 31, 2015]. Retrieved from the internet: <URL://www.forbes.com/sites/matthewherper/2012/05/10/why-astrazeneca-gives-insurers-60-discounts-on-nexiums-list-price/#155191dd4fd6>, submitted as Exhibit 1103 on Mar. 9, 2016 in Inter Partes Review Case Nos. IPR2015-00643, IPR2015-00644 and IPR2015-00830.
Thomas Reinke, MS Drug Going Generic Without Making Waves [online] Managed Care, Jun. 2015, [retrieved on Dec. 31, 2015]. Retrieved from the internet: <URL://www.managedcaremag.com/archives/2015/6/ms-drug-going-generic-without-making-waves>, submitted as Exhibit 1104 on Mar. 9, 2016 in Inter Partes Review Case Nos. IPR2015-00643, IPR2015-00644 and IPR2015-00830.
Carly Helfand, Why is Novartis' Copaxone copy lagging? It's all about coverage, analyst explains [online] Fierce Pharma, Sep. 11, 2015, [retrieved on Dec. 28, 2015]. Retrieved from the internet: <URL://www.fiercepharma.com/story/why-novartis-copaxone-copy-lagging-its-all-about-coverage-analyst-explains/2015-09-11>, submitted as Exhibit 1105 on Mar. 9, 2016 in Inter Partes Review Case Nos. IPR2015-00643, IPR2015-00644 and IPR2015-00830.
Biogen Press Release, Biogen 2015 Revenues Increase 11% to $10.8 Billion [online] biogen.com, Jan. 27, 2016, Retrieved from the internet: <URL://media.biogen.com/press-release/investor-relations/biogen-2015-revenues-increase-11-108-billion>, submitted as Exhibit 1107 on Mar. 9, 2016 in Inter Partes Review Case Nos. IPR2015-00643, IPR2015-00644 and IPR2015-00830.
A to Z of MS Alemtuzumab (Lemtrada), Multiple Sclerosis Trust—information, education, research and support [online] Multiple Sclerosis Trust, Dec. 16, 2014 [retrieved on Jun. 2, 2015]. Retrieved from the internet: <URL://www.mstrust.org.uk/atoz/alemtuzumab-lemtrada.jsp>, submitted as Exhibit 1108 on Mar. 9, 2016 in Inter Partes Review Case Nos. IPR2015-00643, IPR2015-00644 and IPR2015-00830.
R. Osborne, Buzz around Campath proof-of-concept trial in MS, 27(1) Nature Biotechnology 6 (2009), submitted as Exhibit 1109 on Mar. 9, 2016 in Inter Partes Review Case Nos. IPR2015-00643, IPR2015-00644 and IPR2015-00830.
J. A. Cohen et al., Alemtuzumab versus interferon beta 1a as first-line treatment for patients with relapsing-remitting multiple sclerosis: a randomized controlled phase 3 trial, 380 Lancet, 3801819 (2012), submitted as Exhibit 1110 on Mar. 9, 2016 in Inter Partes Review Case Nos. IPR2016-00643, IPR2015-00644 and IPR2015-00830.
IMS Institute for Health Informatics, Medicine Use and Shifting Costs of Healthcare, Chart Notes, Apr. 2014, submitted as Exhibit 1111 on Mar. 9, 2016 in Inter Partes Review Case Nos. IPR2015-00643, IPR2015-00644 and IPR2015-00830.
IMS Institute for Health Informatics, Declining Medicine Use and Costs: For Better or Worse, May 2013, submitted as Exhibit 1112 on Mar. 9, 2016 in Inter Partes Review Case Nos. IPR2015-00643, IPR2015-00644 and IPR2015-00830.
Valeant Pharms. Int'l, Inc., Transcript of Jun. 17, 2014 Investor Presentation [online] SEC.gov [retrieved on May 26, 2015]. Retrieved from the internet: <URL://www.sec.gov/Archives/edgar/data/850693/000119312514239987/d745316d425.htm>, submitted as Exhibit 1113 on Mar. 9, 2016 in Inter Partes Review Case Nos. IPR2015-00643, IPR2015-00644 and IPR2015-00830.
Brian Orelli, Momenta Slowed (Temporarily) [online] The Motley Fool, Nov. 7, 2015 [retrieved on Dec. 28, 2015]. Retrieved from the internet: <URL://www.fool.com/investing/general/2015/11/07/momenta-slowed-temporarily.aspx>, submitted as Exhibit 1114 on Mar. 9, 2016 in Inter Partes Review Case Nos. IPR2015-00643, IPR2015-00644 and IPR2015-00830.
Carly Helfand, The top 10 best-selling multiple sclerosis drugs of 2013 [online]. FiercePharma, Sep. 9, 2014 [retrieved on May 27, 2015]. Retrieved from the internet: <URL://www.fiercepharma.com/special-reports/top-10-best-selling-multiple-sclerosis-drugs-2013>, submitted as Exhibit 1115 on Mar. 9, 2016 in Inter Partes Review Case Nos. IPR2015-00643, IPR2015-00644 and IPR2015-00830.
Tracy Staton, Sanofi tags newly OK'd MS drug Lemtrada at $158K, ready to tout head-to-head Rebif data [online], FiercePharmaMarketing, Nov. 17, 2014 [retrieved on May 27, 2015]. Retrieved from the internet: <URL://www.fiercepharmamarketing.com/node/2101/print>, submitted as Exhibit 1116 on Mar. 9, 2016 in Inter Partes Review Case Nos. IPR2015-00643, IPR2015-00644 and IPR2015-00830.
Kim Frick et al., Serono to sell Amgen multiple sclerosis drug [Novantrone] in U.S. [online], Firstword Pharma, Nov. 13, 2002 [retrieved on May 27, 2015]. Retrieved from the internet: <URL://firstwordpharma.com/print/212958?tsid=17>, submitted as Exhibit 1117 on Mar. 9, 2016 in Inter Partes Review Case Nos. IPR2015-00643, IPR2015-00644 and IPR2015-00830.
Christopher Luzzio & B. Mark Keegan, Multiple Sclerosis Medication [online], Medscape Reference, Nov. 24, 2014 [retrieved on May 28, 2015]. Retrieved from the internet: <URL://emedicine.medscape.com/article/1146199-medication#1>, submitted as Exhibit 1118 on Mar. 9, 2016 in Inter Partes Review Case Nos. IPR2015-00643, IPR2015-00644 and IPR2015-00830.
IMS Health, U.S. Pharmaceutical Market: Trends Issues & Outlook, Sep. 15, 2013, submitted as Exhibit 1120 on Mar. 9, 2016 in Inter Partes Review Case Nos. IPR2015-00643, IPR2015-00644 and IPR2015-00830.
Jesse David & Marion B. Stewart, Commercial Success: Economic Principles Applied to Patent Litigation, in Exonomic Damages in Intellectual Property: A Hands-on Guide to Litigation 159-170, Daniel Slottje ed., John Wiley & Sons, Inc. 2006, submitted as Exhibit 1121 on Mar. 9, 2016 in Inter Partes Review Case Nos. IPR2015-00643, IPR2015-00644 and IPR2015-00830.
Angela Maas, New Copaxone Formulation Could Help Teva Retain Market Share [online[, AIS Health, Feb. 19, 2014 [retrieved on Dec. 31, 2015[. Retrieved from the internet: <URL://aishealth.com/blog/pharmacy-benefit-management/new-copaxone-formulation-could-help-teva-retain-market-share>, submitted as Exhibit 1122 on Mar. 9, 2016 in Inter Partes Review Case Nos. IPR2015-00643, IPR2015-00644 and IPR2015-00830.
Gina Shaw, Glatopa is Strong out of the Gate [online], Specialty Pharmacy Continuum (Jul. 22, 2015), Retrieved from the internet: <URL://www.specialtypharmacycontinuum.com/Article/PrintArticle?articleID=33101>, submitted as Exhibit 1124 on Mar.

(56) References Cited

OTHER PUBLICATIONS 9, 2016 in Inter Partes Review Case Nos. IPR2015-00643, IPR2015-00644 and IPR2015-00830.

David Risinger et al., Morgan Stanley Analyst Report: Teva Pharmaceutical Industries Ltd. (Mar. 14, 2014), submitted as Exhibit 1125 on Mar. 9, 2016 in Inter Partes Review Case Nos. IPR2015-00643, IPR2015-00644 and IPR2015-00830.

Organization Disclosures [online], MS Coalition [retrieved on Mar. 6, 2016], Retrieved from the internet: <URL://www.ms-coalition.org/emergingtherapies/disclosures/organization-disclosures>, submitted as Exhibit 1128 on Mar. 9, 2016 in Inter Partes Reivew Case Nos. IPR2015-00643, IPR2015-00644 and IPR2015-00830.

Alisa Woods, The Costs of Multiple Sclerosis Treatment [online], Everyday Health (Feb. 22, 2016) [retrieved on Mar. 6, 2016], Retrieved from the internet: <URL://www.everydayhealth.com/multiple-sclerosis/treatment/costs-of-ms-treatment/>, submitted as Exhibit 1129 on Mar. 9, 2016 in Inter Partes Review Case Nos. IPR2015-00643, IPR2015-00644 and IPR2015-00830.

Geeta Anand, Through Charities, Drug Makers Help People—and Themselves [online], Wall St. J. (Dec. 1, 2005) [retrieved on Mar. 8, 2016]. Retrieved from the internet: <URL://www.wsj.com/articles/SB113339802749110822>, submitted as Exhibit 1130 on Mar. 9, 2016 in Inter Partes Review Case Nos. IPR2015-00643, IPR2015-00644 and IPR2015-00830.

Malcolm Gladwell, High Prices: How to think about prescription drugs [online], New Yorker (Oct. 25, 2004) [retrieved on Sep. 8, 2012]. Retrieved from the internet: <URL://www.newyorker.com/magazine/2004/10/25/high-prices>, submitted as Exhibit 1131 on Mar. 9, 2016 in Inter Partes Review Case Nos. IPR2015-00643, IPR2015-00644 and IPR2015-00830.

Ernst R. Berndt et al., An Analysis of the Diffusion of New Antidepressants: Variety, Quality, and Marketing Efforts, 5(1) J. of Mental Health Pol'y and Econs. 3 (2002), submitted as Exhibit 1132 on Mar. 9, 2016 in Inter Partes Review Case Nos. IPR2015-00643, IPR2015-00644 and IPR2015-00830.

Ernst R. Berndt et al., Information, marketing, and pricing in the U.S. antiulcer drug market, 85(2) Am. Econ. Rev. 100 (1995), submitted as Exhibit 1133 on Mar. 9, 2016 in Inter Partes Review Case Nos. IPR2015-00643, IPR2015-00644 and IPR2015-00830.

FDA approves new MS treatment regimen developed at Wayne State University by Dr. Omar Khan [online], Division of Research—research@wayne [retrieved on Mar. 8, 2016]. Retrieved from the internet: <URL://research.wayne.edu/rwnews/article.php?id=1319>, submitted as Exhibit 1134 on Mar. 9, 2016 in Inter Partes Review Case Nos. IPR2015-00643, IPR2015-00644 and IPR2015-00830.

Order Construing the Terms of U.S. Pat. Nos. 8,232,250, 8,399,413, 8,969,302, and 9,155,776, In Re Copaxone 40 mg Consolidated Cases, No. 14-1171-GMS (consolidated) (D. Del. Mar. 7, 2016), ECF No. 214, submitted as Exhibit 1136 on Mar. 9, 2016 in Inter Partes Review Case Nos. IPR2015-00643, IPR2015-00644 and IPR2015-00830.

Stipulation and [Proposed] Order Concerning Claim Construction Dispute, In Re Copaxone 40 mg Consolidated Cases, No. 14-1171-GMS (consolidated) (D. Del. Feb. 12, 2016), ECF No. 194, submitted as Exhibit 1137 on Mar. 9, 2016 in Inter Partes Review Case Nos. IPR2015-00643, IPR2015-00644 and IPR2015-00830.

Transcript of Trial Testimony, Teva Pharms. *USA, Inc. v. Sanzo, Inc.*, No. 1:09-cv-08824 (S.D.N.Y. Sep. 7, 2011), ECF No. 205, submitted as Exhibit 1138 on Mar. 9, 2016 in Inter Partes Review Case Nos. IPR2015-00643, IPR2015-00644 and IPR2015-00830.

Ampyra® Prescribing Information, published Dec. 2014 by Acorda Therapeutics, Inc, submitted as Exhibit 1139 on Mar. 9, 2016 in Inter Partes Review Case Nos. IPR201600643, IPR2015-00644 and IPR2015-00830.

Xinke Zhang & Joel W. Hay, Cost-effectiveness of Fingolimod, Teriflunomide, Dimethyl Fumarate and Intramuscular Interferon Beta-1a in Relapsing-remitting Multiple Sclerosis, poster presentation allegedly at Monday Morning, PND20, ISPOR 19th Annual International Conference, Montreal, Quebec, Canada, allegedly on May 2014, submitted as Exhibit 1101 on Mar. 9, 2016 in Inter Partes Review Case Nos. IPR2015-00643, IPR2015-00644 and IPR2015-00830.

Xinke Zhang & Joel W. Hay, Cost-effectiveness of Fingolimod, Teriflunomide, Dimethyl Fumarate and Intramuscular Interferon Beta-1a in Relapsing-remitting Multiple Sclerosis, poster presentation allegedly at the American Society for Health Economics 5th Biennial Conference, Los Angeles, CA, allegedly on Jun. 2014, submitted as Exhibit 1102 on Mar. 9, 2016 in Inter Partes Review Case Nos. IPR2015-00643, IPR2015-00644 and IPR2015-00830.

3-Times-A-Week Copaxone® 40 MG [online], Teva [retrieved date unknown]. Retrieved from the internet: <URL://www.copaxone.com/about-copaxone/copaxone-40-mg>, submitted as Exhibit 1106 on Mar. 9, 2016 in Inter Partes Review Case Nos. IPR2015-00643, IPR2015-00644 and IPR2015-00830.

10 Disease-modifying Treatments [online], MomentumMagazineOnline.com, allegedly on Nov. 2013 [retrieved date unknown]. Retrieved from the internet: <URL://bit.ly/1eVa0jT>, submitted as Exhibit 1119 on Mar. 9, 2016 in Inter Partes Review Case Nos. IPR2015-00643, IPR2015-00644 and IPR2015-00830.

Specialty Maximum Allowable Cost (MAC) [online], Missouri Dep't of Soc. Servs., alleged date Mar. 1, 2016 [retrieved date unknown]. Retrieved from the internet: <URL://dss.mo.gov/mhd/cs/pharmacy/pdf/macspec.pdf>, submitted as Exhibit 1123 on Mar. 9, 2016 in Inter Partes Review Case Nos. IPR2015-00643, IPR2015-00644 and IPR2015-00830.

Financial Support [online], Teva Neuroscience 2015, [Retrieved allegedly on Dec. 2, 2015]. Retrieved from the internet: <URL://www.copaxone.com/shared-solutions/copaxone-savings-and-benefits>, submitted as Exhibit 1126 on Mar. 9, 2016 in Inter Partes Review Case Nos. IPR2015-00643, IPR2015-00644 and IPR2015-00830.

Copaxone [online], Teva Neuroscience 2015, [Retrieved allegedly on Jan. 8, 2016]. Retrieved from the internet: <URL://www.copaxone.com>, submitted as Exhibit 1127 on Mar. 9, 2016 in Inter Partes Review Case Nos. IPR2015-00643, IPR2015-00644 and IPR2015-00830.

U.S. Appl. No. 11/651,212, dated Jan. 9, 2007 to Mar. 9, 2010, submitted as Exhibit 1135 on Mar. 9, 2016 in Inter Partes Review Case Nos. IPR2015-00643, IPR2015-00644 and IPR2015-00830.

Deposition Transcript of Dr. Ari Green, which deposition took place on Oct. 22, 2015, submitted as Exhibit 1065 on Nov. 18, 2015 in Inter Partes Review Case Nos. IPR2015-00643, IPR2015-00644 and IPR2015-00830.

Final Written Decision under 35 U.S.C. § 318(a) and 37 C.F.R. § 42.73, issued on Aug. 24, 2016 by the United States Patent and Trademark Office Patent Trial and Appeal Board in connection with *Mylan Pharmaceuticals Inc. v. Yeda Research & Development Co. Ltd.* for U.S. Pat. No. 8,232,250 (Case No. IPR2015-00643).

Final Written Decision under 35 U.S.C. § 318(a) and 37 C.F.R. § 42.73, issued on Aug. 24, 2016 by the United States Patent and Trademark Office Patent Trial and Appeal Board in connection with *Mylan Pharmaceuticals Inc. v. Yeda Research & Development Co. Ltd.* for U.S. Pat. No. 8,399,413 (Case No. IPR2015-00644).

Final Written Decision under 35 U.S.C. § 318(a) and 37 C.F.R. § 42.73, issued on Sep. 1, 2016 by the United States Patent and Trademark Office Patent Trial and Appeal Board in connection with *Mylan Pharmaceuticals Inc. v. Yeda Research & Development Co. Ltd.* for U.S. Pat. No. 8,969,302 (Case No. IPR2015-00830).

Complaint, dated Jan. 13, 2017, filed in connection with *Teva Pharmaceuticals USA, Inc., Teva Pharmaceutical Industries Ltd., and Teva Neuroscience, Inc., v. Sandoz Inc. and Momenta Pharmaceuticals Inc.*, in Case No. 3:17-cv-00275-FLW-DEA, in the United States District Court for the District of New Jersey.

Complaint, dated Jan. 17, 2017, filed in connection with *Teva Pharmaceuticals USA, Inc., Teva Pharmaceutical Industries Ltd., and Teva Neuroscience, Inc., v. Mylan Pharmaceuticals Inc., Mylan Inc., and Natco Pharma Ltd.*, in Case No. 1:17-cv-00007-IMK, in the United States District Court for the Northern District of West Virginia.

Complaint, dated Jan. 17, 2017, filed in connection with *Teva Pharmaceuticals USA, Inc., Teva Pharmaceutical Industries Ltd., and Teva Neuroscience, Inc., v. Synthon Pharmaceuticals Inc.,*

(56) References Cited

OTHER PUBLICATIONS

*Synthon B.V., Synthon S.R.O., and Pfizer Inc.*, in Case No. 1:17-cv-00345-LGS, in the United States District Court for the Southern District of New York.

Complaint, dated Jan. 25, 2017, filed in connection with *Teva Pharmaceuticals USA, Inc., Teva Pharmaceutical Industries Ltd., and Teva Neuroscience, Inc.,* v. *Anneal Pharmaceuticals LLC and Amneal Pharmaceuticals Co. GMBH*, in Case No. 2:17-cv-00416-JMA-AYS, in the United States District Court for the Eastern District of New York.

Complaint, dated Jan. 25, 2017, filed in connection with *Teva Pharmaceuticals USA, Inc., Teva Pharmaceutical Industries Ltd., and Teva Neuroscience, Inc.,* v. *Dr. Reddy's Laboratories, Ltd. and Dr. Reddy's Laboratories, Inc.*, in Case No. 3:17-cv-00517-FLW-DEA, in the United States District Court for the District of New Jersey.

Complaint for Declaratory Judgment, dated Jan. 25, 2017, filed in connection with *Anneal Pharmaceuticals LLC and Amneal Pharmaceuticals Company GMBH* v. *Teva Pharmaceuticals USA, Inc., Teva Pharmaceutical Industries Ltd., and Teva Neuroscience, Inc.*, in Case No. 1:17-cv-00074-UNA, in the United States District Court for the District of Delaware.

Complaint for Declaratory Judgment, dated Feb. 2, 2017, filed in connection with *Momenta Pharmaceuticals, Inc.* v. *Teva Pharmaceuticals USA, Inc., Teva Pharmaceutical Industries Ltd., and Teva Neuroscience, Inc.*, in Case No. 1:17-cv-00109-GMS, in the United States District Court for the District of Delaware.

Communication under Rule 71(3) EPC, dated on Jan. 11, 2017, issued by the European Patent Office in connection with European Patent Application No. 15186721.5.

Certificate of Grant Standard Patent, dated Feb. 2, 2017, issued by the Australian Government IP Australia in connection with Australian patent application No. 2015380381.

Office Action dated Nov. 17, 2016 issued by the Canadian Intellection Property Office in connection with Canadian Application No. 2,945,537.

Nov. 23, 2016 Amendment in Response to Oct. 20, 2016 Office Action submitted with the Eurasian Patent Office in connection with Eurasian Patent Application No. 201500881, including English language version of a draft of the Nov. 23, 2016 Amendment and of the Oct. 20, 2016 Office Action.

Dec. 9, 2016 Amendment in Response to Oct. 31, 2016 Office Action submitted with the Colombian Patent Office in connection with Colombian Patent Application No. NC2016/0002988, including English language version of a draft of the Dec. 9, 2016 Amendment and of the Oct. 31, 2016 Office Action.

Office Action dated Dec. 28, 2016 issued by the Austrian Patent Office in connection with Austrian Utility Model Application No. 4A GM50174/2016-2, including an English language machine translation of the Dec. 28, 2016 Office Action.

Apr. 21, 2015 Office Action issued by the U.S. Patent and Trademark Office in connection with U.S. Appl. No. 14/608,126 (Exhibit 1); and.

Jun. 2, 2015 Amendment to Apr. 21, 2015 Office Action filed with the U.S. Patent and Trademark Office in connection with U.S. Appl. No. 14/608,126 (Exhibit 2).

Dec. 7, 2015 Information on Oral Proceedings issued by the European Patent Office in connetion with Opposition filed against EP2405749B.

Apr. 23, 2015 Summons to attend oral proceedings pursuant to Rule 115(1) EPC and Communication accompanied by Summons (EPO form 2906) issued by the European Patent Office in connection with Opposition filed against EP2405749B.

Oct. 7, 2015 Letter accompanied by Comments in advance to Oral Proceedings scheduled for Dec. 7, 2015 filed by Yeda Research Development Co., Ltd. with the European Patent Office in connection with Opposition filed against EP2405749B.

Nov. 9, 2015 Reply, filed by Synthon B.V. with the European Patent Office in connection with Opposition filed against EP2405749B.

U.S. Appl. No. 2007-0161566, published Jul. 12, 2007 (Pinchasi), submitted as Exhibit D1 of Opposition filed against EP2405749B.

Fletcher et al., "Comparison of glatiramer acetate (Copaxone®) and interferon β-1b (Betaferon®) in multiple Sclerosis patients:an open-label 2-year follow-up" J. Neural Sci vol. 197, pp. 51-55, submitted as Exhibit D2 of Opposition filed against EP2405749B.

Fletcher et al., "Copolymer 1 (Glatiranler Acetate) in Relapsing Forms of Multiple Sclerosis: Open Multicenter Study of Alternate-Day Adn1inistration" Clin Neuropharm 2002, vol. 25(1), pp. 11-15, submitted as Exhibit D3 of Opposition filed against EP2405749B.

Khan et al., Randomized, prospective, rater-blinded, four-year, pilot study to compare the effect of daily versus every-other-day glatiramer acetate 20 mg subcutaneous injections in relapsing-remitting multiple sclerosis Multiple Sclerosis 2008, vol. 14. S295, submitted as Exhibit D4 of Opoositon filed against EP2405749B.

Caon et al., "Randomized, Prospective, Rater-Blinded, Four Year Pilot Study To Compare The Effect of Daily Versus Every Other Day Glatiramer Acetate 20 mg Subcutaneous Injections in RRMS" Neurobiology 2008, vol. 68 (12), Suppl 3, submitted as Exhibit D5 of Opposition filed against EP2405749B.

Cohen et al. "Randomized, double-blind, dose-comparision study of glatiramer acetate relapsing-remitting MS", Neurology 2007, vol. 68 (12), pp. 939-944, submitted as Exhibit D6 of Opposition filed against EP2405749B.

Simpson et al., "Glatiramer Acetate: A review of its Use in relapsing-Remitting Multiple Sclerosis" Adis Drug Evaluation, Glatiramer Acetate, 2002, submitted a Exhibit D7 of Opposition filed against EP2405749B.

Teva Provides Update on Forte Trial, published on Jul. 7, 2008 at Jerusalem, Israel by Teva Pharmaceutical Industries Ltd., submitted as Exhibit D8 of Opposition filed against EP2405749B.

"News Release, Teva to Present Positive Data for Glatiramer Acetate 40 mg/1ml Given Three Times Weekly for Relapsing-Remitting MS" [online] Teva Pharmaceutical Industries Ltd. Oct. 10, 2012 [retrieved on Apr. 2, 2013]. Retrieved from the Internet: <URL://www.tevapharm.com/Media/News/Pages/2012/1743500.aspx?year=2012&page . . . >, submitted as Exhibit D9 of Opposition filed against EP2405749B.

Kahn et. al, "Late Breaking News II: A phase 3 trial to assess the efficacy and Safety of glatiramer acetate injections 40mg administered 3 times a week compared to placebo", abstract presented on Oct. 13, 2012 at the 28th Congress of the European Committee for Treatment and Research in Multiple Sclerosis held at Lyon France on Oct. 10-13, 2012, submitted as Exhibit D10 of Opposition filed against EP2405749B.

"Copaxone 20mg/ml, Solution for Injection, Pre-filled Syringe" [online] Teva Pharmaceutical Ltd., Feb. 3, 2009 [retrieved on Jan. 27, 2013]. Retrieved from the Internet:<URL://www.medicines.org.uk/EMC/printfriendlydocument.aspx?documentid=17516>>, submitted as Exhibit D11 of Opposition filed against EP2405749B.

PCT International Application Publication No. WO 2005/0120542, Published Dec. 22, 2005 (Rasmussen at al.), submitted as Exhibit D12 of Opposition filed against EP2405749B.

U.S. Appl. No. 2005-0014696, published Jan. 20, 2005 (Yong et al.), submitted as Exhibit D13 of Opposition filed against EP2405749B.

U.S. Apple No. 2009-0149541, published Jun. 11, 2009 (Stark et al.), submitted as Exhibit D14 of Opposition filed against EP2405749B.

Yong et al. "Immunological response to different doses of GA in MS: Analyses from the Forte trial" dated Apr. 28, 2009, Abstract only, submitted as Exhibit D15 of Opposition flid against EP2405749B.

Jul. 1, 2009 Response to Apr. 2, 2009 Final Office Action filed with the U.S Patent and Trademark Office in connection with U.S. Appl. No. 1/651,212, submitted as Exhibit D16 of Opposition filed against EP2405749B.

PCT International Application Publication No. WO 00/18794, published Apr. 6, 2000 (Gad et al.), submitted as Exhibit D17 of Opposition filed against EP2405749B.

Sep. 13, 2012 Response to Aug. 8, 2015 Communication pursuant to Article 94(3) EPC filed with the European Patent Office in connection with European Patent Application No. 10810282.3, submitted as Exhibit D18 of Opposition filed against EP2405749B.

(56) References Cited

OTHER PUBLICATIONS

Comi et al. "Results from a phase II, 1-year, Randomized, Double-blind, Parallel-Group, Dose Comparison Study with Glatiramer Acetate in Relapsing-remitting Multiple Sclerosis", abstract at the World Congress on Treatment and Research in Multiple Sclerosis—Montreal 2008, presented on Sep. 20, 2008, [online] [retrieved on Aug. 21, 2015]. Retrieved from the Internet:<URL://www.multiwebcast.com/wctrims/2008/msmontreal/2448/chair.giancarlo.comi.r . . .>submitted as Exhibit D19 of Opposition filed against EP2405749B.

Slides of G. Comi, Forte: Results from a phase II, 1-year, Randomized, Double-blind, Parallel-Group, Dose Comarison Study with Glatiramer Acetate in Relapsing-remitting Multiple Sclerosis, Presented at World Congress on Treatment and Research in Multiple Sclerosis: 2008 Joint Meeting of the American, European, and Latin America Committees on Treatment and Research in Multiple Sclerosis, San Raffaele, Italy (ACTRIMS, ECTRIMS, LACTRIMS) (2008), submitted as Exhibit D19a of Opposition filed against EP2405749B.

Oct. 2, 2015 Expert Report of Dr Simon Day, submitted as Exhibit D20 of Opposition filed against EP2405749B.

"News Release: Teva Initiates Phase III Study to Confirm Increased Efficacy of Higher Dose of Glatiramer Acetate for the Treatment of Relapsing-Remitting Multiple Sclerosis" [online] Teva Pharmaceutical Industries Ltd., Jul. 27, 2006 [retrieved on Apr. 6, 2015]. Retrieved from the Internet: <URL://ir.tevapharm.com/phoenix.zhtml?c=73925&p=irol-newsArticle&ID=1557343>, submitted as Exhibit D21 of Opposition filed against EP2405749B.

"News Release: Data Published In Neurology Showed That Higher Dose of Copaxone® Increased Efficacy In Relapsing-Remitting Multiple Sclerosis (Rrms)" [online] Teva Pharmaceutical Industries Ltd., Apr. 17, 2007 [retrieved on Apr. 6, 2015]. Retrieved from the Internet: <URL://ir.tevapharm.com/phoenix.zhtml?c=73925&p=irol-newsArticle&ID=1554611>, submitted as Exhibit D22 of Opposition filed against EP2405749B.

"Medscape Medical News: Doubling the Dose of Glatiramer Acetate Does Not Increase Efficacy" [online] Medscape, Sep. 22, 2008, [retrieved on Jan. 6, 2015] Retrieved from the Internet:<URL://www.medscape.com/viewartice/580865>, submitied as Exhibit D23 of Opposition filed against EP2405749B.

"Daily News: High-dosage Copaxone trial results are bad news for Teva" [online] PharmaTimes, Jul. 7, 2008, [retrieved on Nov. 6, 2015]. Retrieved from the Internet: <URL://http://www.pharmatimes.com/article/08-07-07/High-dosage_Copaxone_trial_results_. . .>, submitted as Exhibit D24 of Opposition filed against EP2405749B.

Committee or Medicinal Products for Human Use (CHMP) "Guidelines on Clinical Investigation of Medicinal Products for the Treatment of Multiple Sclerosis", European Medicines Agency, Nov. 16, 2006, submitted as Exhibit D25 of Opposition filed against EP2405749B.

Varkoni et al. "The glatiramoid class of immunomodulator Drugs" Expert Opinion on Pharmacotherapy 2009 10(4) 657-668, submitted as Exhibit D26 of Opposition filed agaiast EP2405749B.

Meiner et al. In "Frontiers in Multiple Sclerosis: Clinical research and Therapy" Eds Abramsky & Ovadia (1997) 213-221, submitted as Exhibit D27 of Opposition filed against EP2405749B.

McKeage "Glatiramer Acetate 40 mg/mL in Relapsing-Remitting Multiple Sclerosis: A Review" ADIS Drug Evaluation, Apr. 2015, submitted as Exhibt D28 of Opposition filed against EP2405749B.

Wolinski "Reduced frequency severity of injection site reactions with glatiramer acetate 40mg/mL three times weekly dosing" ECTRIMS/ECTRIMS Conference, Sep. 10-13, 2014, poster, submitted as Exhibit D29 of Opposition filed against EP2405749B.

Wolinsky et al. "Reduced frequency severity of injection site reactions with glatiramer acetate 40mg/mL three times weekly dosing", poster presented at the Joint Americas Committee for Treatment and Research in Multiple Sclerosis (ACTRIMS)—European Committee for Treatment and Research in Multiple Sclerosis (ECTRIMS) Meeting, held on Sep. 10-13, 2014, at Boston MA, submitted as Exhibit D30 of Opposition filed against EP2405749B.

Oct. 5, 2015 Expert Report of Professor Wolfgang Bruck, submitted as Exhibit D31 of Opposition filed against EP2405749B.

Multiple Sclerosis Society of Canada "Talking About Clinically Isolated Syndrome or CIS" published by Communications and Services, Multiple Sclerosis Society of Canada, Quebec Division, dated 2009, submitted as Exhibit D32 of Opposition filed against EP2405749B.

Affidavit of Marlene S. Bobka dated Nov. 10, 2014, submitted as Exhibit D35 of Opposition filed against EP2405749B.

Decision rejecting the opposition (Art. 101(2) EPC) issued by the European Patent Office on Jan. 19, 2016 in connection with Opposition filed against EP2405749B.

U.S. Appl. No. 09/359,099, filed Jul. 22, 1999 (Strominger et al.). The specification and claims as originally filed.

U.S. Appl. No. 11/258,850, filed Sep. 14, 2005 (Schwartz et al.). The specification and claims as originally filed.

U.S. Appl. No. 11/654,374, filed Jan. 16, 2007 (Schwartz et al.). The specification and claims as originally filed.

U.S. Appl. No. 14/520,280, filed Oct. 21, 2014 (Tchelet et al.). The specification and claims as originally filed.

Reissue Application in connection with U.S. Appl. No. 13/964,856, filed Aug. 12, 2013 (Konfino et al.).

File history of U.S. Appl. No. 13/964,856, filed Aug. 12, 2013 (Konfino et al.).

Request for Ex Parte Re-examination by Third Party in connection with U.S. Appl. No. 90/013,249, filed May 21, 2014 (Konfino et al.).

File history of U.S. Appl. No. 90/013,249, filed May 21, 2014 (Konfino et al.).

U.S. Appl. No. 14/630,326, filed Feb. 24, 2015 (Klinger) (unpublished U.S. Patent application preserved in confidence under 37 C.F.R. §1.14 accessible to public upon publication).

U.S. Appl. No. 14/673,257, filed Mar. 30, 2015 (Klinger) (unpublished U.S. Patent application preserved in confidence under 37 C.F.R. §1.14, accessible to public upon publication).

U.S. Appl. No 14/720,556, filed May 22, 2015 (Klinger) (unpublished U.S. Patent application preserved in confidence under 37 C.F.R. §1.14, accessible to public upon publication).

Citizen Petition Requesting That FDA Refrain From Approving Any Abbreviated New Drug Application Referencing Copaxone® (glatiramer acetate injection) Until Certain Conditions Are Met, Jul. 2, 2014 [online]. Regulations.gov [retrieved on Feb. 19, 2015], Retrieved from the Internet: <URL:www.regulations.gov/#!documentDetail;D=FDA-2014-P-0933-0001>.

Citizen Petition Requesting That FDA Refrain From Approving Any Abbreviated New Drug Application Referencing Copaxone® (Glatiramer Acetate Injection) Until Certain Conditions Are Met, Dec. 5, 2013 [online]. Regulations.gov [retrieved on Feb. 19, 2015], Retrieved from the Internet: <URL:www.regulations.gov/#!documentDetail;D=FDA-2014-P-1641-0001>.

Feb. 6, 2015 Petition for Inter Partes Review filed in connection with *Mylan Pharmaceuticals Inc.* v. *Yeda Research & Development Co. Ltd.* for U.S. Pat. No. 8,232,250 in the United States Patent and Trademark Office Patent Trial and Appeal Board (Case No. IPR2015-00643).

Declaration of Stephen J. Peroutka, M.D., Ph.D., cited in Feb. 6, 2015 Petition for Inter Partes Review (Case No. IPR2015-00643).

Expert Declaration of Ari Green, M.D. in Support of Petition for Inter Partes Review of U.S. Patent No. 8,232,250, cited in Feb. 6, 2015 Petition for Inter Partes Review (Case No. IPR2015-00643).

Feb. 7, 2015 Petition for Inter Partes Review filed in connection with *Mylan Pharmaceuticals Inc.* v. *Yeda Research & Development Co. Ltd.* for U.S. Pat. No. 8,399,413 in the United States Patent and Trademark Office Patent Trial and Appeal Board (Case No. IPR2015-00644).

Declaration of Stephen J. Peroutka, M.D., Ph.D., cited in Feb. 7, 2015 Petition for Inter Partes Review (Case No. IPR2015-00644).

Expert Declaration of Ari Green, M.D. in Support of Petition for Inter Partes Review of U.S. Pat. No. 8,232,250, cited in Feb. 7, 2015 Petition for Inter Partes Review (Case No. IPR2015-00644).

Affidavit of Marlene S. Bobka dated Dec. 9, 2014 and John J. Jessop, Review and Evaluation of Pharmacology Toxicology Data

(56) References Cited

OTHER PUBLICATIONS

Original NDA Review (1996) ("the 1996 FDA SBOA"), submitted as Exhibit 1007 in Inter Partes Review Case Nos. IPR2015-00643, IPR2015-00644 and IPR2015-00830.
PCT International Application Publication No. WO 2007/081975, published Jul. 19, 2007 (Pinchasi), cited in Feb. 6, 2015 Petition for Inter Partes Review (Case No. 1PR2015-00643) and Feb. 7, 2015 Petition for Inter Partes Review (Case No. IPR2015-00644).
Cohen, et al., "Randomized, double-blind, dose comparison study of glatiramer acetate in relapsing-remitting MS", Neurology, 2007, 68; 939-944, cited in Feb. 6, 2015 Petition for Inter Partes Review (Case No. IPR2015-00643) and Feb. 7, 2015 Petition for Inter Partes Review (Case No. IPR2015-00644).
Flechter S, et al., "Copolymer 1 (Glatiramer Acetate) in Relapsing Forms of Multiple Sclerosis: Open Multicenter Study of Alternate-Day Adlninistration"Clinical Neuropharmacology, 2002, 25: 11-15, cited in Feb. 6, 2015 Petition for Inter Partes Review (Case No. IPR2015-0643) and Feb. 7, 2015 Petition for Inter Partes Review (Case No. IPR2015-00644).
Khan et al., "Randomized, prospective, rater-blinded, four-year, pilot study to compare the effect of daily versus every-other-day injections in relapsing-remitting multiple sclerosis"Mult. Scler. 2008, 14 Suppl. 1 S296, cited in Feb. 6, 2015 Petition for Inter Partes Review (Case No. IPR2015-0643) and Feb. 7, 2015 Petition for Inter Partes Review (Case No. IPR2015-00644).
Caon et al., "Randomized, prospective, rater-blinded, four year pilot study to compare the effect of daily versus every other day glatiramer acetate 20 mg subcutaneous injections in RRMS" Neurology, 2009, vol. 72, No. 11, p. A317, cited in Feb. 6, 2015 Petition for Inter Partes Review (Case No. IPR2015-00643) and Feb. 7, 2015 Petition for Inter Partes Review (Case No. IPR2015-00644).
Teva Provides Update on Forte Trial Jerusalem, Israel (Jul. 7, 2008), cited in Feb. 7, 2015 Petition for Inter Partes Review (Case No. IPR2015-00644).
Copaxone®, Food and Drug Administration Approved Labeling, 2001 (NDA 20-622/S-015/S-015) cited in Feb. 7, 2015 Petition for Inter Partes Review (Case No. IPR2015-00644).
Copaxone®, Food and Drug Administration Approved Labeling, Feb. 2009, cited in Feb. 7, 2015 Petition for Inter Partes Review (Case No. IPR2015-00644).
Jacobs et al., "Intramuscular interferon beta-1a therapy initiated during a first demyelinating event in multiple sclerosis" New Engl. J. med. 2000, 343:898-904, cited in Feb. 7, 2015 Petition for Inter Partes Review (Case No. IPR2015-00644).
Sep. 10, 2014 Complaint, filed in connection with *Teva Pharmaceuticals USA, Inc., et al., v. Sandoz Inc. and Momenta Pharmaceuticals, Inc.* in the the United States District Court for District of Delaware (Case No. 1:14-cv-001171-GMS).
Nov. 3, 2014 Answer, filed in connection with *Teva Pharmaceuticals USA, Inc., et al., v. Sandoz Inc. and Momenta Pharmaceuticals, Inc.* in the United States District Court for District of Delaware (Case No. 1:14-cv-001171-GMS).
Dec. 1, 2014 Answer to Counterclaims, filed in connection with *Teva Pharmaceuticals USA, Inc., et al., v. Sandoz Inc. and Momenta Pharmaceuticals, Inc.* in the United States District Court for District of Delaware (Case No. 1:14-cv-001171-GMS).
Sep. 10, 2014 Complaint, filed in connection with *Teva Pharmaceuticals USA, Inc., et al., v. Doctor Reddy's Laboratories Ltd. and Doctor Reddy's Laboratories, Inc.* in the United States District Court for the District of Delaware (Case No. 1:14-cv-01172-GMS).
Nov. 3, 2014 Answer, filed in connection with *Teva Pharmaceuticals USA, Inc., et al., v. Doctor Reddy's Laboratories Ltd. and Doctor Reddy's Laboratories, Inc.* in the United States District Court for the District of Delaware (Case No. 1:14-cv-01172-GMS).
Dec. 1, 2014 Answer to Counterclaims, filed in connection with *Teva Pharmaceuticals USA, Inc., et al., v. Doctor Reddy's Laboratories Ltd. and Doctor Reddy's Laboratories, Inc.* in the United States District Court for the District of Delaware (Case No. 1:14-cv-01172-GMS).

Sep. 11, 2014 Complaint, filed in connection with *Teva Pharmaceuticals USA, Inc., et al., v. Doctor Reddy's Laboratories Ltd., Doctor Reddy's Laboratories, Inc., Sandoz, Inc., and Momenta Pharmaceuticals* in the United States District Court for the District of New Jersey (Case No. 3:14-cv-05672-MAS-TJB).
Nov. 25, 2014 Plaintiff's Notice of Voluntary Dismissal, filed in connection with *Teva Pharmaceuticals USA, Inc., et al., v. Doctor Reddy's Laboratories Ltd., Doctor Reddy's Laboratories, Inc., Sandoz, Inc., and Momenta Pharmaceuticals* in the United States District Court for the District of New Jersey (Case No. 3:14-cv-05672-MAS-TJB).
Oct. 6, 2014 Complaint, filed in connection with *Teva Pharmaceuticals USA, Inc., et al., v. Mylan Pharmaceuticals Inc., Mylan Inc. and Natco Pharma Ltd.* in the United States District Court for the District of Delaware (Case No. 1:14-cv-01278-GMS).
Oct. 7, 2014 Complaint, filed in connection with *Teva Pharmaceuticals USA, Inc., et al., v. Mylan Pharmaceuticals Inc., Mylan Inc. and Natco Pharma Ltd.* in the United States District Court for the Northern District of West Virginia (Case No. 1:14-cv-00167-IMK).
Nov. 26, 2014 Answer, filed in connection with *Teva Pharmaceuticals USA, Inc., et al., v. Mylan Pharmaceuticals Inc., Mylan Inc. and Natco Pharma Ltd.* in the United States District Court for the Northern District of West Virginia (Case. No. 1:14-cv-00167-IMK).
Nov. 18, 2014 Complaint, filed in connection with *Teva Pharmaceuticals USA, Inc., et al., v. Synthon Pharmaceuticals Inc., et al.* in the United States District Court for the District of Delaware (Case. No. 1:14-cv-0141.9-UNA).
Jan. 23, 2015 Answer, filed in connection with *Teva Pharmaceuticals USA, Inc., et al., v. Synthon Pharmaceuticals Inc,. et al.* in the United States District Court for the District of Delaware (Case. No. 1:14-cv-01419-UNA).
Feb. 17, 2015 Answer to Counterclaims, filed in connection with *Teva Pharmaceuticals USA, Inc., et al., v. Synthon Pharmaceuticals Inc,. et al.* in the United States District Court for the District of Delaware (Case. No. 1:14-cv-01419-UNA).
Nov. 19, 2014 Complaint, filed in connection with *Teva Pharmaceuticals USA, Inc., et al., v. Synthon Pharmaceuticals Inc,. et al.* in the United States District Court for the Middle District of North Carolina (Case. No. 1:14-cv-975).
Feb. 12, 2015 Plaintiff's Notice of Voluntary Dismissal, filed in connection with *Teva Pharmaceuticals USA, Inc., et al., v. Synthon Pharmaceuticals Inc,. et al.* in the United States District Court for the Middle District of North Carolina (Case. No. 1:14-cv-975).
Feb. 3, 2015 Complaint, filed in connection with *Teva Pharmaceuticals USA, Inc., et al., v. Amneal Pharmaceuticals LLC* in the United States District Court for the District Delaware (Case. No. 1:15-cv-00124-GMS).
May 26, 2015 Yeda's Preliminary Patent Owner Response, filed in connection with *Mylan Pharmaceuticals Inc. v. Yeda Research & Development Co. Ltd.* for U.S. Pat. No. 8,232,250 in the United States Patent and Trademark Office Patent Trial and Appeal Board (Case No. IPR2015-00643).
May 26, 2015 Yeda's Preliminary Patent Owner Response, filed in connection with *Mylan Pharmaceuticals Inc. v. Yeda Research & Development Co. Ltd.* for U.S. Pat. No. 8,399,413 in the United States Patent and Trademark Office Patent Trial and Appeal Board (Case No. IPR2015-00644).
Teva Provides Update on Forte Trial (Jul. 7, 2008), submitted as Exhibit 2001 in Inter Partes Review Case Nos. IPR2015-00643 and IPR2015-00644.
Franscisco J. Quintana et al., Systems Biology Approaches for the Study of Multiple Sclerosis, 12 J. Cell. Mol. Med. 4, 1087-93 (2008), submitted as Exhibit 2002 in Inter Partes Review Case Nos. IPR2015-00643 and IPR2015-00644.
David J. Virley, Developing Therapeutics for the treatment of multiple sclerosis, 2 J. Am. Soc. for Exp. Neurotherapeutics, 638-49 (Oct. 2005), submitted as Exhibit 2003 in Inter Partes Review Case Nos. IPR2015-00643 and IPR2015-00644.
Manuel A. Friese, The value of animal models for drug development in multiple sclerosis, 129 Brain, 1940-52 (2006), submitted as Exhibit 2004 in Inter Partes Review Case Nos. IPR2015-00643 and IPR2015-00644.

(56) References Cited

OTHER PUBLICATIONS

Copaxone Prescribing Information (Jan. 2014), submitted as Exhibit 2005 in Inter Partes Review Case Nos. IPR2015-00643 and IPR2015-00644.
Dvora Teitelbaum et al., Suppression of experimental allergic encephalomyelitis by a synthetic polypeptide, 1 Eur. J. Immunol., 242-248 (Aug. 1971), submitted as Exhibit 2006 in Inter Partes Review Case Nos. IPR2015-00643 and IPR2015-00644.
Jill Conner, Glatiramer acetate and therapeutic peptide vaccines for mutiple sclerosis, 1 J. Autoimmunity and Cell Responses 3 (2014), submitted as Exhibit 2007 in Inter Partes Review Case Nos. IPR2015-00643 and IPR2015-00644.
Copaxone, Physicians' Desk Reference 62ed. (2008), submitted as Exhibit 2008 in Inter Partes Review Case Nos. IPR2015-00643 and IPR2015-00644.
Wiebke Schrempf and Tjalf Ziemssen, Glatiramer acetate:Mechanisms of action in multiple sclerosis, 6 Autoimmun. Rev., 469-475 (2007), submitted as Exhibit 2009 in Inter Partes Review Case Nos. IPR2015-00643 and IPR2015-00644.
V. Wee Yong, Differential mechanisms of action of interferon-β and glatiramer acetate in MS, 59 Neurology, 802-8 (Apr. 2002), submitted as Exhibit 2010 in Inter Partes Review Case Nos. IPR2015-00643 and IPR2015-00644.
Suhayl Dhib-Jalbut, Mechanisms of action of interferons and glatiramer acetate in multiple sclerosis, 58 Neurology (8 Suppl 4), S3-9 (2002), submitted as Exhibit 2011 in Inter Partes Review Case Nos. IPR2015-00643 and IPR2015-00644.
Oliver Neuhaus et al., Pharmacokinetics and pharmacodynamics of the interferon-betas, glatiramer acetate, and mitoxantrone in multiple sclerosis, 259 J. Neurol. Sci., 27-37 (2007), submitted as Exhibit 2012 in Inter Partes Review Case Nos. IPR2015-00643 and IPR2015-00644.
Oded Abramsky et al., Effect Of A Synthetic Polypeptide (COP 1) On Patients With Multiple Sclerosis and With Acute Disseminated Encephalomyelitis. Preliminary Report, 31 J. Neurol. Sci., 433-38 (1977), submitted as Exhibit 2013 in Inter Partes Review Case Nos. IPR2015-00643 and IPR2015-00644.
Murry B. Bornstein et al., Treatment of Multiple Sclerosis with a Synthetic Polypeptide: Preliminary Results, 105 Tran Am. Neurol. Assoc., 348-50 (1980), submitted as Exhibit 2014 in Inter Partes Review Case Nos. IPR2015-00643 and IPR2015-00644.
Murry B. Bornstein et al., Multiple Sclerosis: Trial of a Synthetic Polypeptide, 11 Ann. Neurol., 317-19 (Mar. 1982), submitted as Exhibit 2015 in Inter Partes Review Case Nos. IPR2015-00643 and IPR2015-00644.
Murry B. Bornstein et al., A Pilot Trial of COP 1 in Exacerbating-Remitting Multiple Sclerosis, 13 N. Engl. J. Med., 408-14 (Aug. 13, 1987), submitted as Exhibit 2016 in Inter Partes Review Case Nos. IPR2015-00643 and IPR2015-00644.
Sage Journals, msj.sagepub.com/content/14/1_suppl.toc (Sep. 2008), submitted as Exhibit 2017 in Inter Partes Review Case Nos. IPR2015-00643 and IPR2015-00644.
Massimo Filippi et al., Effects of oral glatiramer acetate on clinical and MRI monitored disease activity in patients with relapsing multiple sclerosis: a multicentre, double-blind, randomised, placebocontrolled study, neurology.thelancet.com (Jan. 20, 2006), submitted as Exhibit 2018 in Inter Partes Review Case Nos. IPR2015-00643 and IPR2015-00644.
Yuval Ramot et al., Comparative Long-Term Preclinical Safety Evalution of Two Glatiramoid Compounds (Glatiramer Acetate, Copaxonel, and TV-5010, Protiramer) in Rats and Monkeys, 40 Toxicol. Path., 40-54 (2012), submitted as Exhibit 2019 in Inter Partes Review Case Nos. IPR2015-00643 and IPR 2015-00644.
U.S. Appl. No. 2007/0161566 A1 ("Pinchasi"), submitted as Exhibit 2020 in Inter Partes Review Case Nos. IPR2015-00643 and IPR2015-00644.
Tjalf Ziemssen et al. Risk-Benefit Assessment of Glatiramer Acetate in Multiple Sclerosis, 24 Drug Safety, 13, 979-90 (2001), submitted as Exhibit 2021 in Inter Partes Review Case Nos. IPR2015-00643 and IPR2015-00644.

Teva Press Release, Phase III Data Published in Annals of Neurology Show That a Higher Concentration Dose of Glatiramer Acetate Given Three Times a Week Reduced Annualized Relapse Rates in the Treatment of Relapsing-Remitting Multiple Sclerosis (Jul. 1, 2013), submitted as Exhibit 2022 in Inter Partes Review Case Nos. IPR2015-00643 and IPR2015-00644.
Omar Khan et al., Three Times Weekly Glatiramer Acetate in Relapsing-Remitting Multiple Sclerosis, 73 Ann. Neurol., 705-13 (2013), submitted as Exhibit 2023 in Inter Partes Review Case Nos. IPR2015-00643 and IPR2015-00644.
Teva Press Release, Teva Reports First Quarter 2015 Results (Apr. 30. 2015), submitted as Exhibit 2024 in Inter Partes Review Case Nos. IPR2015-00643 and IPR2015-00644.
Kate McKeage, Glatiramer Acetate 40 mg/mL in Relapsing-Remitting Multiple Sclerosis: A Reviews CNS Drugs (Apr. 24, 2015), submitted as Exhibit 2025 in Inter Partes Review Case Nos. IPR2015-00643 and IPR2015-00644.
K.P. Johnson et al., Copolymer 1 reduces relapse rate and improves disability in relapsing-remitting multiple sclerosis: Results of a phase I11 multicenter, doubleblind, placebo-controlled trial, 45 Neurology, 1268-76 (1995), submitted Exhibit 2026 in Inter Partes Review Case Nos. IPR2015-00643 and IPR2015-00644.
Feb. 24, 2015 Answer, filed in connection with *Teva Pharmaceuticals USA Inc., et al., v. Amneal Pharmaceuticals LLC* in the United States District Court for the District of Delaware (Case. No. 1:15-cv-00124-GMS).
Mar. 20, 2015 Answer to Amneal's Counterclaims, filed in connection with *Teva Pharmaceuticals USA, Inc., et al., v. Sandoz Inc. and Amneal Pharmaceuticals LLC*, in the the United States District Court for District of Delaware (Case No. 1:14-cv-01171-GMS).
May 19, 2015 Answer, Affirmative Defenses and Counterclaims of Amneal Pharmaceuticals LLC to Plaintiff's First Amended Complaint for Patent Infringement, in the United States District Court for the District of Delaware (Case No. 1:14-cv-01171-GMS) (Consolidated).
May 21, 2015 Answer, Affirmative Defenses and Counterclaims of Amneal Pharmaceuticals LLC to Plaintiff's First Amended Complaint for Patent Infringement in the United States District Court for the District of Delaware (Case No. 1:14-cv-01171-GMS) (Consolidated).
May 21, 2015 Synthon's Answer, Affirmative Defenses and Counterclaims to Plaintiff's First Amended Complaint for Patent Infringement in the United States District Court for the District of Delaware (Case No. 1:14-cv-01171-GMS) (Consolidated).
May 21, 2015 Sandoz and Momenta Pharmaceuticals, Inc.'s Answer to Complaint for Patent Infringement and Counterclaims in the United States District Court for the District of Delaware (Case No. 1:14-cv-01171-GMS) (Consolidated).
May 21, 2015 DRL's Answer and Counterclaims to First Amended Complaint in the United States District Court for the District of Delaware (Case No. 1:14-cv-01171-GMS) (Consolidated).
Costello, K. et al., "Recognizing Nonadherence in Patients with Multiple Sclerosis and Maintaining Treatment Adherence in the Long Term,"Medscape J Med., vol. 10(9):225 (2008).
Edgar, C.M. et al., "Lipotrophy in Patients with Multiple Sclerosis on Glatiramer Acetate," Can. J. Neurol. Sci., vol. 31:58-63 (2004).
Ford, CC., et al, "A Prospective open-label study of glatiramer acetate: over a decade of continuous use in multiple sclerosis patients," Multiple Sclerosis, vol. 12:309-320 (2006).
Gagnon, L., "Every-Other-Day Dosing of Giatiramer Acetate Reduces Adverse Reactions With Comparable Efficacy to Daily Dosing: Presented at WCTRMS," PeerView Press, (Sep. 21, 2008).
Ge, Y., et al. "Glatiramer Acetate (Copaxone) Treatment in Relapsing-Remitting Multiple Sclerosis", Neurology, vol. 54:813-817 (Feb. 2000).
Johnson, K.P., et al., "Copolymer 1 reduces relapse rate and improves disability in relapsing-remitting multiple sclerosis: Results of a phase III multicenter, double-blind, placebo-controlled trial," Neurology, vol. 45:1268-1276 (Jul. 1995).
Klauer , T., and Zettl, U.K., "Compliance, adherence, and the treatment of multiple sclerosis," J Neurol. vol. 255 (Suppl. 6):87-92 (2008).

(56) References Cited

OTHER PUBLICATIONS

Lisak, R.P. and Kira, J., "Chapter 100, Multiple Sclerosis," International Neurology, 366-374 (2009).
Manso, P.J., and Sokol., A.L., "Life cycle management of ageing pharmaceutical assets," Pharmaceutical Law Insight, vol. 3 (7) :16-19 (Jul./Aug. 2007).
Copaxone®, Physicians' Desk Reference, 62nd ed. Montvale, NJ, Thomson Healthcare Inc., pp. 3231-3235 (2008).
Rebif®(interferon beta-1a), Product Description, 103795.5062PI final Jun. 7, 2005 (2005).
Betaseron® Interferon beta-1b, Product Label, 2003 (10004938), submitted as Exhibit 1048 in Inter Partes Review Case Nos. IPR2015-00643, IPR2015-00644 and IPR2015-00830.
This is MS Multiple Sclerosis Community: Knowledge & Support [online], ThisIsMS [retrieved on Sep. 3, 2014]. Retrieved from the Internet: URL:www.thisisms.com/forum/copaxonef4/topic5610.html.
Clinical Trial Comparing Treatment of Relapsing-Remitting Multiple Sclerosis (RR-MS) With Two Doses of Glatiramer Acetate (GA) [online]. ClinicalTrials.gov, 1993 [retrieved on Feb. 13, 2015]. Retrieved from the Internet: <URL:clinicaltrials.gov/show/NCT00337779>.
A Study to Test the Effectiveness and Safety of a New Higher 40mg Dose of Copaxone® Compared to Copaxone® 20mg, the Currently Approved Dose [online], ClinicalTrials.gov, 1993 [retrieved on Feb. 13, 2015]. Retrieved from the Internet: <URL:clinicaltrials.gov/show/NCT00202982>.
Safety and Tolerability of Glatiramer Acetate (GLACIER). ClinicalTrials.gov, 1993 [retrieved on Feb. 19, 2015]. Retrieved from the Internet: URL:clinicaltrials.gov/ct2/show/NCT01874145.
Bornstein et al., "A Placebo-controlled, Double-blind, Randomized Two-center, Pilot Trial of Cop 1 in Chronic Progressive Multiple Sclerosis," Neurol., 1991, 41, 533-539.
Bornstein et al., "Rationale for Immunomodulating Therapies of Multiple Sclerosis: Clinical Trial Design in Multiple Sclerosis Therapy," Neurol., 1988, vol. 38 (Suppl. 2), pp. 80-81 [R].
Bornstein, "Clinical Experience: Hopeful Prospects In Multiple Sclerosis," Hospital Practice (Off. Ed.), 1992, vol. 27, No. 5, pp. L135-158, 141-142, 145-158.
Bornstein, "Cop 1 may be Beneficial for Patients with Exacerbating-remitting Form of Multiple Sclerosis," Adv. Ther. (USA), 1987, 4, 206 (Abstract).
Bornstein et al, "Treatment of Multiple Sclerosis with Copolymer 1" in Treatment of Multiple Sclerosis: Trial Design, Results and Future Perspectives (Rudick R.A. & Goodkin D.E., eds., Springer Lerlag, London, 1992) 173-198.
Bornstein et al., "A Pilot Trial of Cop 1 in Exacerbating-remitting Multi Sclerosis," New Eng. J. Med., 1987, 317(7), 408-414.
Bornstein, et al., "Clinical Experience with COP-1 in Multiple Sclerosis," Neurol., 1988, 38(Suppl. 2) 66-69.
Bornstein et al., "Clinical Trials of a Synthetic Polypeptide (Copolymer 1) for the treatment of Multiple Sclerosis" in Gonsett et al., Immunological and Clinical Aspects of Multiple Sclerosis (MTP Press, The Hague, 1984) 144-150.
Bornstein et al., "Clinical Trials of Copolymer 1 in Muitipie Sclerosis," Ann. N.Y. Acad. Sci. (USA), 1984, 366-372.
Bornstein et al., "Multiple Sclerosis: Clinical Trials of a Synthetic Polypeptide, Copolymer 1," Neurol., 1985, 35, (Suppl. 1), 103 (Abstract).
Bornstein et al., "Multiple Sclerosis: Trial of a Synthetic Polypeptide,"Ann. Neurol., 1982, 11, 317-319.
Bornstein et al., "Pilot Trial of COP-1 in Chronic Progressive Multiple Sclerosis: Preliminary Report," from The International Multiple Sclerosis Conference: An Update on Multiple Sclerosis, Roma (Italy), Sep. 15-17, 1988, in Elsevier Science Publisher, 1989, 225-232.
Bornstein et al., "Treatments of Multiple Sclerosis with a Synthetic Polypeptide: Preliminary Results," Ann. Neurol., 1980, 8, 117 (Abstract).

Bornstein et al., "Treatments of Multiple Sclerosis with a Synthetic Polypeptide: Preliminary Results," Trans. Am. Neurol. Assoc., 1980, 105, 348-350.
Bornstein et, al., "Clinical Trials of Cop 1 in Multiple Sclerosis," in Handbook of Multiple Sclerosis (S.D. Cook Marcel Rekker, ed., 1990) 469-480.
Caon et al., "Randomized, prospective, rater-blinded, four year pilot study to compare the effect of daily versus every other day glatiramer acetate 20 mg subcutaneous injections in RRMS" Neurology, 2009, vol. 72, No. 11, p. A3I7.
Clinical Trial Protocol No. 9001, Teva Pharmaceutical Industries, Ltd., first patient enrolled Oct. 23, 1991.
Clinical Trial Protocol No. 9002, Lemmon Co. and Teva Pharmaceutical Industries, Ltd., first patient enrolled Jun. 17, 1993.
Cohen et al., "Randomized, double-blind, dose comparison study of glatiramer acetate in relapsing-remitting MS" Neurology, 2007, 68: 939-944.
Cohen et al., "Identifying and treating patients with suboptimal responses" Neurology, 2004, Dec. 28;63(12 Suppl 6):S33-40.
Comi et al. "Treatment with glatiramer acetate delays conversion to clinically definite multiple sclerosis (CDMS) in patients with clinically isolated syndromes (CIS)" Neurology 2008; 71 (2): 153.
Comi G, Filippi M. Presented at: 60th Annual Meeting of the American Academy of Neurology: Apr. 12-19, 2008; Chicago, IL. Abstract LBS.003.
Comi G. "Treatment with glatiramer acetate delays conversion to clinically definite multiple sclerosis (CDMS) in patients with clinically isolated syndromes (CIS)" Program and abstracts of the American Academy of Neurology 60th Annual Meeting; Apr. 12-19, 2008; Chicago, Illinois. LBS.003.
Comi et al. "European/Canadian multicenter, double-blind, randomized, placebo-controlled study of the effects of glatiramer acetate on magnetic resonance imagine-measured diseased activity and burden in patients with relapsing multiple sclerosis". Ann Neurol., 2001, 49:290-7.
Comi et al., "Results from a phase III, one-year, randomized, double-blind, parallel-group, dose-comparison study with glatiramer acetate in relapsing-remitting multiple sclerosis". Mult Scler., 2008, 14(suppl 1):S299.
Copaxone, Food and Drug Administration Approved Labeling (Reference ID: 3443331) [online], TEVA Pharmaceutical Industries Ltd., 2014 [retrieved on Dec. 24, 2014], Retrieved from the Internet: <URL:www.accessdata.fda.gov/drugsatfda_docs/label/2014/020622s0891bl.pdf>.
Fletcher S, et al., "Copolymer 1 (Glatiramer Acetate) in Relapsing Forms of Multiple Sclerosis: Open Multicenter Study of Alternate-Day Adlninistration". Clinical Neuropharmacology, 2002, 25:11-15.
Flechter S. et al, "Comarison of glatiramer acetate (Copaxone®) and interferon beta-1b (Betaferon®) in multiple sclerosis patients: An open-label 2-year follow up" Journal of the Neurological Sciences, 2002, vol. 197, No. 1-2 pp. 51-55.
Immunological Responses to Different Doses of Glatiramer Acetate in MS: Analyses from the FORTE Trial, Yong W. V., et al., poster session dated Apr. 28, 2009, presented at the 61st Annual American Academy of Neurology meeting in Seattle, Washington U.S.A.
Johnson, et al., "Extented use of glatiramer acetate (Copaxone) is well tolerated and maintains its clinical effect on multiple sclerosis relapse rate and degree of disability". Neurology. 1998, 50:701-8.
Jul. 7, 2008 FORTE Trial Update by Teva Pharmaceutical Industries Ltd.
Khan et al., "Randomized, prospective, rater-blinded, four-year, pilot study to compare the effect of daily versus every-other-day injections in relapsing-remitting multiple sclerosis" Mult. Scler. 2008, 14 Suppl. 1 S296.
Khan et al., "Glatiramer acetate 20mg subcutaneous twice-weekly versus daily injections: results of a pilot, prospective, randomised, and rater-blinded clinical and MRI 2-year study in relapsing-remitting multiple sclerosis" Immunomodulation-2; Friday, Sep. 11, 2009.
Khan O. et al., "Randomized, prospective, rater-blinded, four-year, pilot study to compare the effect of daily versus every-other-day

(56) References Cited

OTHER PUBLICATIONS glatiramer acetate 20 mg subcutaneous injections in relapsing-remitting multiple sclerosis", Multiple Sclerosis. 2008, 14: 5295-5298.

Khan O. et al., "A phase 3 trial to assess the efficacy and safety of glatiramer acetate injections 40mg administered 3 times a week compared to placebo" European Committee for Treatment and Research in Multiple Sclerosis, 2012.

Martinelli BF, Rovaris M, Johnson KP, Miller A, Wolinsky JS, Ladkani D, Shifroni G, Comi G, Filippi M. Effects of glatiramer acetate on relapse rate and accumulated disability in multiple sclerosis: meta-analysis of three double-blind, randomized, placebo-controlled clinical trials. Mult Scler. 2003 Aug; 9(4):349-55.

Wolinsky, et al., "Glatiramer acetate in primary progressive multiple sclerosis: Results of a multinational, multicenter, double-blind, placebo-controlled trial". Ann Neurol., 2007, 61:14-24.

Wolinsky, JS, "The use of glatiramer acetate in the treatment of multiple sclerosis". Adv Neurol., 2006, 273-92.

Goossens et al., "Pressure- and temperature-induced unfolding and aggregation of recombinant human interferon-c: a Fourier transform infrared spectroscopy study"Biochem. J. 2003, 370, 529-535.

Gursky et al., "Terperature-dependent β-sheet formation in β-amyloid Aβ1-40 peptide in water: uncoupling β-structure folding from aggregation" Biochimica et Biophysica Acta, 2000, 1476 93-102.

Kim et al. "Some Factors Determining Protein Aggregation during Ultrafiltration", Biotechnology and Bioengineering, 1993, vol. 42, pp. 260-265.

Celik et al., "Protein fouling behavior of carbon nanotube/polyethersulfone composite membranes during water filtration" Water Research, 2011, 45:5287-94.

Shinchuk et al. "Poly-(L-Alanine) Expansions Form Core -Sheets that Nucleate Amyloid Assembly" Proteins: Structure, Function, and Bioinformatics, 2005, 61:579-589.

Varkony et al. "The glatiramoid class of immunomodulator drugs" Expert Opin. Pharmacother. 2009, 10(4):1-12.

Vrijenhoek et al., "Influence of membrane surface properties on initial rate of colloidal fouling of reverse osmosis and nanofiltration membranes" Journal of Membrane Science, 2001, 188:115-128.

Feb. 8, 2017 Answer, Affirmative Defenses, and Counterclaims, filed by Mylan Pharmaceuticals Inc., et al, in connection with *Teva Pharmaceuticals U.S.A. Inc., et al., v. Doctor Reddy's Laboratories Inc., et al.*, in the United States District Court for the District of Delaware (Case No. 1:16-cv-01267 (GMS)).

Feb. 10, 2017 Answer and Counterclaims, filed by Sandos Inc. and Momenta Pharmaceuticals Inc. in connection with *Teva Pharmaceuticals U.S.A. Inc., et al., v. Doctor Reddy's Laboratories Inc., et al.*, in the United States District Court for the District of Delaware (Case No. 1:16-cv-01267 (GMS)).

Feb. 16, 2017 Answer, Additional Defenses, and Counterclaims, filed by Synthon Pharmaceuticals Inc., et al., and Pfizer Inc. in connection with *Teva Pharmaceuticals U.S.A. Inc., et al., v. Doctor Reddy's Laboratories Inc., et al.*, in the United States District Court for the District of Delaware (Case No. 1:16-cv-01267 (GMS)).

Feb. 16, 2017 Answer, Additional Defenses, and Counterclaims, filed by Doctor Reddy's Laboratories, et al., in connection with *Teva Pharmaceuticals U.S.A. Inc., et al., v. Doctor Reddy's Laboratories Inc., et al.*, in the United States District Court for the District of Delaware (Case No. 1:16-cv-01267(GMS)).

Feb. 16, 2017 Answer, Additional Defenses, and Counterclaims, filed by Pfizer Inc. in connection with *Teva Pharmaceuticals U.S.A. Inc., et al., v. Synthon Pharmaceuticals Inc., et al.*, in the United States District Court for the District of Delaware (Case No. 1:17-cv-345 (LGS)).

Apr. 17, 2017 Answer, Additional Defenses, and Counterclaims, filed by Synthon Pharmaceuticals Inc., et al, in connection with *Teva Pharmaceuticals U.S.A. Inc. et al., v. Synthon Pharmaceuticals Inc., et al.*, in the United States District Court for the District of Delaware (Case No. 1:17-cv-00390 (LPS)).

Apr. 18, 2017 Answer, Affirmative Defenses, and Counterclaims, to Complaint filed by Dr. Reddy's Laboratories, Ltd. and Dr. Reddy's Laboratories, Inc., in connection with *Teva Pharmaceuticals U.S.A. Inc. et al., v. Doctor Reddy's Laboratories Inc., et al.*, in the United States District Court for the District of New Jersey (Case No. 3:17-cv-00517 (FLW)).

Xu-Jiang, Y. et al. (1995) "A technique for the study of the fouling of microfiltration membranes using two membranes in series", Journal of Membrane Science, 105:23-30.

May 4, 2017 Answer, Affirmative Defenses and Counterclaims to Complaint, filed by Mylan Pharmaceuticals Inc. and Mylan Inc. in connection with *Teva Pharmaceuticals U.S.A. Inc., et al., v. Mylan Pharmaceuticals Inc., et al.*, in the United States District Court for the District of Delaware (Case No. 1:17-cv-00249(GMS)).

Jun. 16, 2017 Answer, Defenses and Counterclaims, filed by Sandoz, Inc., in connection with *Teva Pharmaceuticals U.S.A. Inc., et al., v. Sandoz Inc.*, in the United States District Court for the District of Delaware (Case No. 1:17-cv-00597(GMS)) (Public dedacted Version).

Akers, J.A. "Chapter 6: Microbiological Considertions in the Selection and Validation of Filter Sterilization." in: Filtration And Purification In The Biopharmaceutical Industry (New York, 2d ed. 2008), vol. 174(Drugs and Pharmaceutical Sciences), pp. 151-161.

Bowman, F.W. et al. (1967) "Microbiological Methods for Quality Control of Membrane Filters", J. Pharm. Sci. 56(2):222-225.

Brose, D.J. et al. "Chapter 5: Membrane Filtration." in: Development And Manufacture Of Protein Pharmaceuticals (New York, 2002), pp. 213-279.

European Commission (Brussels, Nov. 25, 2008) "Vol. 4: EU Guidelines to Good Manufacturing Practice, Medicinal Products for Human and Veterinary Use", Annex 1(Manufacture of Sterile Medicinal Products, corrected version).

Green H. and Meltzer, T.H. "Chapter 10: Flow and Pressure, Filter Sizing, and Filter System Design." in: Filtration in the Pharmaceutical Industry (New York, 1987), pp. 409-452.

Gsponer, J. and Vendruscolo, M. (2006) "Theoretical Approaches to Protein Aggregation", Protein and Peptide Letters 13(3):287-293.

Jornitz, M.W. and Meltzer, T.H. "Chapter 17: Media and Buffer Filter Implications." in: Filtration And Purification In The Biopharmaceutical Industry (New York, 2d ed. 2008), vol. 174(Drugs and Pharmaceutical Sciences), pp. 439-457.

Martin, J.M. and Manteuffel, R.L. (1988) "Protein Recovery from Effluents of Microporous Membranes", Biopharm 1(10):20-27.

Meltzer, T.H. and Jornitz, M.W. "Chapter 7: Filter Sizing: The Requirements and Their Attainment." in: Filtration And Purification In The Biopharmaceutical Industry (New York, 2d ed. 2008), vol. 174(Drugs and Pharmaceutical Sciences), pp. 163-192.

Meltzer, T.H. "Chapter 10: Protein Adsorption by Polymeric Filters."in: Filtration And Purification In The Biopharmaceutical Industry (New York, 2d ed. 2008), vol. 174(Drugs and Pharmaceutical Sciences), pp. 257-295.

(SPK2049-e140506) Sartorius Stedim Biotech GmbH (Goettingen, Germany, 2014) "Data Sheet: Sartobran® P 0.2 μm Sterilizing Grade Filter Cartridges", version 5.

Stinavage, P.S. "Chapter 13: Validation of the Filter and of the Filtration Process."in: Filtration And Purification In The Biopharmaceutical Industry (New York, 2d ed. 2008), vol. 174(Drugs and Pharmaceutical Sciences), pp. 371-387.

Truskey, G.A. et al. (1987) "The Effect of Membrane Filtration Upon Protein Conformation", J. Parenteral Sci. & Tech. 41(6):180-193.

U.S. Department of Health and Human Services (Sep. 2004) "Sterile Drug Products Produced by Aseptic Procession: Current Good Manufacturing Practice.", Food and Drug Administration.

Zaman, M. et al. (2014) "Nanoparticles in Relation to Peptide and Protein Aggregation", Int'l J. Nanomedicine 9:899-912.

Jornitz, M.W. and Meltzer, T.H. (2011) "Sterile Filtration—A Practical Approach".

Defendants Dr. Reddy's Laboratories Ltd., Dr. Reddy's Laboratories Inc., Sandoz Inc., Momenta Pharmaceuticals Inc., Mylan Pharmaceuticals Inc., Mylan Inc., Synthon Pharmaceuticals Inc., Synthon B.V., Synthon S.R.O., Pfizer Inc., Amneal Pharmaceuticals LLC, and Amneal GMBH's Initial Joint Invalidity Contentions

(56) References Cited

OTHER PUBLICATIONS

Regarding U.S. Pat. No. 9,155,755 B2, filed Jul. 26, 2017 by Dr. Reddy's Laboratories Ltd., Dr. Reddy's Laboratories Inc., Sandoz Inc., Momenta Pharmaceuticals Inc., Mylan Pharmaceuticals Inc., Mylan Inc., Synthon Pharmaceuticals Inc., Synthon B.V., Synthon S.R.O., Pfizer Inc., Amneal Pharmaceuticals LLC, and Amneal GMBH in connection with *Teva Pharmaceuticals USA Inc., Teva Pharmaceuticals Industries Ltd., Teva Neuroscience, Inc., and Yeda Research and Development Co., Ltd. v. Dr. Reddy's Laboratories Ltd., Dr. Reddy's Laboratories Ltd., Dr. Reddy's Laboratories Inc., Sandoz Inc., Momenta Pharmaceuticals Inc., Mylan Pharmaceuticals Inc. Mylan Inc., Synthon Pharmaceuticals Inc., Synthon B.V., Synthon S.R.O., Pfizer Inc., Amneal Pharmaceuticals LLC, and Amneal GMBH*, in the United States District Court for the District of Delaware (Case Nos. 16-cv1267-GMS, 17-cv-074-GMS, 17-cv-109-GMS, 17-cv-249-GMS, 17-cv-390-GMS, 17-cv-597-GMS, 17-cv-693-GMS).
Afzal et al. (2013) "Nanolipodendrosome-loaded glatiramer acetate and myogenic differentiation I as augmentation therapeutic strategy approaches in muscular dystrophy" International Journal of Nanomedicine 8:2943-60.
Akers, M.J. Sterile Drug Products: Formulation, Packaging, Manufacturing and Quality, Drugs and the Pharmaceuticals Sciences (2010) Chapter 12.
Copaxone® Label (revised Aug. 2012), at Supplement 087.
Conner J.B. et al. "Copaxone® in the Era of Biosimilars and Nanosimilars: Nanoparticles, Imaging, Therapy, and Clinical Applications." in : Handbook of Clinical Nanomedicine (1st ed. 2016) 1:783.
Detroy, A. et al. "Single-Use Technology in Parenteral Filling." in: Biopharm International (2014) 27(3).
Dosmar M. and Pinto M. "Chapter 19: Crossflow Filtration." in: Filtration And Purification In The Biopharmaceutical Industry (New York, 2d ed. 2008), vol. 174(Drugs and Pharmaceutical Sciences), pp. 495-542.
Fritch, J. and Moraru, C.I. (2008) "Development and Optimization of a Carbon Dioxide-Aided Cold Microfiltration Process for the Physical Removal of Microorganisms and Somatic Cells from Skim Milk", J. Dairy Sci 94:3744-60.
Graves, K. et al. (2006) "Broth Conditions Determining Specific Cake Resistance During Microfiltration of Bacillus subtilis", Biotechnology and Bioengineering 94(2):346-52.
Jornitz, M.W. and Meltzer, T.H. "Filtration And Purification In The Biopharmaceutical Industry" (New York, 2d ed. 2008), vol. 174(Drugs and Pharmaceutical Sciences).
Jornitz, M.W. and Meltzer, T.H. "Chapter 2: Adsorption." in: Sterile Filtration—A Practical Approach (New York, 2011), pp. 108-122.
Lehman, E.D. et al. (1992) "Large-scale purification and characterization of recombinant tick anticoagulant peptide", Journal of Chromatography 574:225-35.
Levy R. "Chapter 40: Sterile Filtration of Liquids and Gases." in: Disinfection, Sterilization, and Preservation (Philadelphia, 5th ed. 2001), pp. 795-822.

Letter from J. Michael Nicholas to J. Woodcock, Citizen Petition, Docket No. FDA-2009-P-0555 (Nov. 13, 2009).
Martinez V.P.M. et al. (2014) "Comparability of a Three-Dimensional Structure in Biopharmaceuticals Using Spectroscopic Methods", J Anal Methods Chem 2014:1-11.
Meireles M. et al. (1991) "Albumin Denaturation During Ultrafiltration: Effects of Operating Conditions and Consequences on Membrane Fouling", Biotechnology and Bioengineering 38:528-34.
(DS1428EN00) MilliporeSigma (United States 2017) "Data Sheet: Millipore Express® SHC Hydrophilic Filters", version 10, available at <http://www.emdmillipore.com/US/en/product/Millipore-Express-SHC-0.5%2F0.2%C2%A0%CE%BCm-Hydrophilic-Filters,MM_NF-C9146#documentation>.
Mo, H. et al. (2008) "Fouling of reverse osmosis membrane by protein (BSA): Effects of pH calcium, magnesium, ionic strength and temperature", Journal of Membrane Science 315:28-35.
Peinemann K.V. and Nunes S.P. "Membranes for Life Sciences" (Germany, 2008) Chapter 4.
Ponnusamy, E. (2011) "A new and greener method to manufacture copolymer-1" Sustainable Chemistry 154:33-38.
Schwartz J.B. (1998) "Technical Report No. 26: Sterilizing Filtration of Liquids", PDA J. Pharmaceutical Sci. and Tech. 52(May/Jun. Supp.):1.
Sharif, N.A. and Burt, D.R. (1983) "Rat brain TRH receptor: kinetics, pharmacology, distribution and ionic effects", Regulatory Peptides 7:399-411.
Sigma-Aldrich Co., LLC (United States 2017) "Amino Acids Reference Chart", [online], 2017 [retrieved Mar. 23, 2017]. Retrieved from the internet: available at <http://www.sigmaaldrich.com/life-science/custom-oligos/custom-peptides/learning-center/peptide-stability.html>.
Sigma-Aldrich Co., LLC (United States 2017) "Peptide Stability", [online], 2017 [retrieved May 30, 2017]. Retrieved from the internet: available at <http://www.sigmaaldrich.com/life-science/metabolomics/learning-center/amino-acid-reference-chart.html>.
Steinhauer T. et al. (2015) "Temperature Dependent Membrane Fouling During Filtration of Whey and Whey Proteins", J. Membrane Sci. 492:364.
Suvarna, K. et al. (2011) "Case Studies of Microbial Contamination in Biologic Product Manufacturing", J. Am. Pharmaceutical Rev. Jan./Feb.:50-56.
The European Agency for the Evaluation of Medicinal Products, Committee for Proprietary Medicinal Products (CPMP) (London, Apr. 1996) "Note for Guidance: Manufacture of the Finished Dosage Form" 486/95. Re-Issue.
The European Agency for the Evaluation of Medicinal Products, Committee for Veterinary Medicinal Products (London, Jun. 1996) "Note for Guidance: Manufacture of the Finished Dosage Form" 126/95.
United States Pharmacopeial Convention, Counsel of Experts and its Expert Committees "United States Pharmacopeia 36" The National Formulary 31, vol. 1:, May 1, 2013, pp. 33-37, 539-540.
United States Pharmacopeial Convention, Counsel of Experts and its Expert Committees "United States Pharmacopeia 36" The National Formulary 31, vol. 3:, May 1, 2013, pp. 4200-4201.

\* cited by examiner

PROCESS FOR MANUFACTURING GLATIRAMER ACETATE PRODUCT

RELATED APPLICATIONS

This application is a continuation of U.S. Ser. No. 14/608,126, filed Jan. 28, 2015, now allowed, the contents of which are hereby incorporated by reference in their entirety into this application.

The disclosures of various publications in their entireties are hereby incorporated by reference into this application in order to more fully describe the state of the art to which this invention pertains.

BACKGROUND OF THE INVENTION

Glatiramer acetate (GA), the active ingredient of Copaxone®, consists of the acetate salts of synthetic polypeptides, containing four naturally occurring amino acids: L-glutamic acid, L-alanine, L-tyrosine, and L-lysine with an average molar fraction of 0.141, 0.427, 0.095, and 0.338, respectively. The peak average molecular weight of glatiramer acetate is between 5,000 and 9,000 daltons. Glatiramer acetate is identified by specific antibodies (Copaxone, Food and Drug Administration Approved Labeling (Reference ID: 3443331) [online], TEVA Pharmaceutical Industries Ltd., 2014 [retrieved on Dec. 24, 2014], Retrieved from the Internet: <URL: www.accessdata.fda.gov/drugsatfda_docs/label/2014/020622s0891bl.pdf>).

Chemically, glatiramer acetate is designated L-glutamic acid polymer with L-alanine, L-lysine and L-tyrosine, acetate (salt). Its structural formula is:

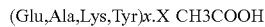

(Glu,Ala,Lys,Tyr)$x$.X CH3COOH

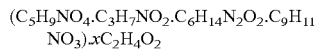

($C_5H_9NO_4.C_3H_7NO_2.C_6H_{14}N_2O_2.C_9H_{11}NO_3$)$.xC_2H_4O_2$

CAS-147245-92-9

Copaxone® is a clear, colorless to slightly yellow, sterile, nonpyrogenic solution for subcutaneous injection. Each 1 mL of Copaxone® solution contains 20 mg or 40 mg of GA, the active ingredient, and 40 mg of mannitol. The pH of the solutions is approximately 5.5 to 7.0. Copaxone® 20 mg/mL in a prefilled syringe (PFS) is an approved product, the safety and efficacy of which are supported by over two decades of clinical research and over a decade of post-marketing experience. Copaxone® 40 mg/mL in a PFS was developed as a new formulation of the active ingredient GA. Copaxone® 40 mg/mL is a prescription medicine used for the treatment of people with relapsing forms of multiple sclerosis (Copaxone, Food and Drug Administration Approved Labeling (Reference ID: 3443331) (online), TEVA Pharmaceutical Industries Ltd., 2014 [retrieved on Dec. 24, 2014], Retrieved from the Internet: <URL: www.accessdata.fda.gov/drugsatfda_docs/label/2014/020622s0891bl.pdf>).

It is an object of the present invention to provide an improved process for manufacturing GA drug products.

SUMMARY OF THE INVENTION

The patent provides a process of preparing a pharmaceutical preparation of glatiramer acetate and mannitol in a suitable container comprising the steps of:

(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

This patent also provides a prefilled syringe containing 40 mg of glatiramer acetate and 40 mg mannitol, which syringe is prepared by a process of the invention.

This patent further provides an aqueous pharmaceutical solution comprising 40 mg/ml glatiramer acetate and 40 mg/ml mannitol, wherein the aqueous pharmaceutical solution
 a) has a viscosity in the range of 2.0-3.5 cPa; or
 b) has an osmolality in the range of 275-325 mosmol/Kg.

This patent also provides a prefilled syringe containing 1 ml of an aqueous pharmaceutical solution prepared by a process of the invention.

This patent also provides an automated injector comprising the prefilled syringe prepared by a process of the invention.

Aspects of the present invention relate to a method of treatment of a human patient suffering from a relapsing form of multiple sclerosis comprising administration to the human patient of three subcutaneous injections of a 40 mg/ml dose of glatiramer acetate per week using the prefilled syringe of this invention, using the aqueous pharmaceutical solution of this invention, or using the automated injector of this invention so as to treat the human patient.

DETAILED DESCRIPTION OF THE INVENTION

Figure 1:
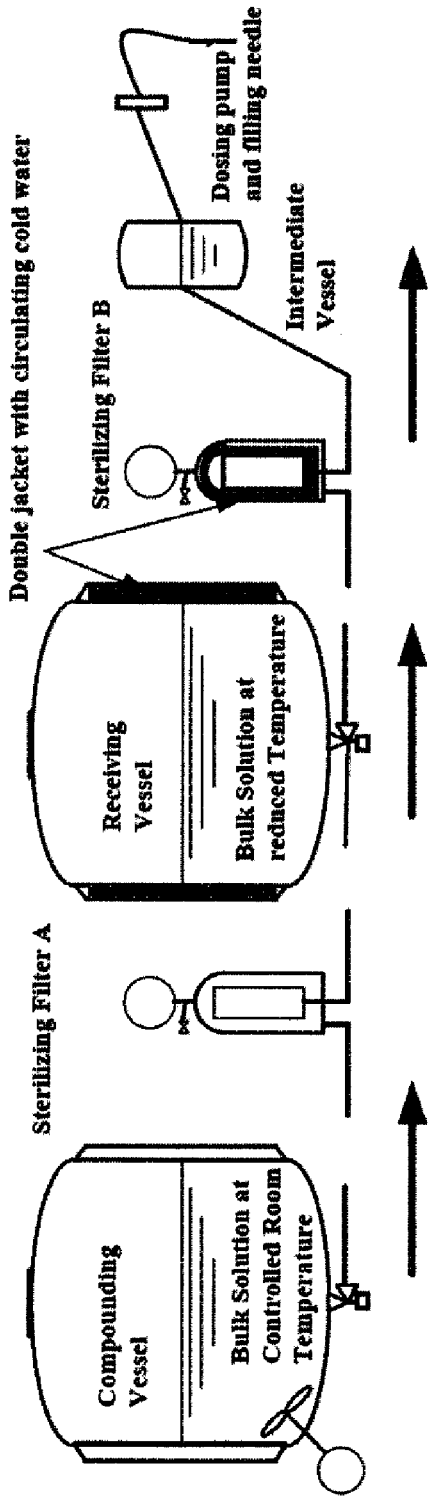
FIG. 1. Schematic description of filtration process by cooled receiving vessel and filter housing.

This invention provides a process of preparing a pharmaceutical preparation of glatiramer acetate and mannitol in a suitable container comprising the steps of:

(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

In some embodiments the filtering step (ii) comprises filtering the aqueous pharmaceutical solution through a first filter, or a first filter and a second filter.

In some embodiments the process further comprises the step of reducing the temperature of the second filter to a temperature from above 0° C. up to 17.5° C.

In some embodiments the process further comprises the step of reducing the temperature of the aqueous pharmaceutical solution to a temperature from above 0° C. up to 17.5° C. before passing through the second filter.

In some embodiments the filtering step (ii) further comprises the step of receiving the aqueous pharmaceutical solution filtered through the first filter in a receiving vessel.

In same embodiments the process further comprises the step of reducing the temperature of the aqueous pharmaceutical solution to a temperature from above 0° C. up to 17.5° C. after leaving the receiving vessel and before entering into the second filter.

In some embodiments the process further comprises the step of reducing the temperature of the aqueous pharmaceutical solution to a temperature from above 0° C. up to 17.5° C. while in the receiving vessel.

In some embodiments the process further comprises the step of reducing the temperature of the first filter to a temperature from above 0° C. up to 17.5° C.

In some embodiments the process further comprises the step of reducing the temperature of the aqueous pharmaceutical solution to a temperature from above 0° C. up to 17.5° C. before passing through the first filter.

In some embodiments the obtaining step (i) comprises compounding the aqueous pharmaceutical solution in a compounding vessel.

In some embodiments the process further comprises the step of reducing the temperature of the aqueous pharmaceutical solution to a temperature from above 0° C. up to 17.5° C. after leaving the compounding vessel and before entering into the first filter.

In some embodiments the process further comprises the step of reducing the temperature of the aqueous pharmaceutical solution to a temperature from above 0° C. up to 17.5° C. while in the compounding vessel.

In some embodiments the aqueous pharmaceutical solution is passed through the second filter at a rate of 3-25 liters/hour.

In some embodiments the aqueous pharmaceutical solution is passed through the second filter preferably at a rate of 3-22 liters/hour.

In some embodiments the aqueous pharmaceutical solution is passed through the second filter more preferably at a rate of 3-15 liters/hour.

In some embodiments the aqueous pharmaceutical solution is passed through the second filter at a rate more preferably at a rate of 3-10 liters/hour.

In some embodiments the pressure during the filtering step (ii) and the pressure during the filling step (iii) is maintained below 5.0 bar.

In some embodiments the pressure during the filtering step (ii) and the pressure during the filling step (iii) is maintained preferably below 3.0 bar.

In some embodiments the pressure during the filtering step (ii) and the pressure during the filling step (iii) is maintained below 2.0 bar.

In some embodiments the temperature of the aqueous pharmaceutical solution is between 0° C. and 14° C., or the temperature of the aqueous pharmaceutical solution is reduced to a temperature between 0° C. and 14° C.

In some embodiments the temperature of the aqueous pharmaceutical solution is between 0° C. and 12° C., or the temperature of the aqueous pharmaceutical solution is reduced to a temperature between 0° C. and 12° C.

In some embodiments the temperature of the aqueous pharmaceutical solution is 2° C.-12° C., or the temperature of the aqueous pharmaceutical solution is reduced to 2° C.-12° C.

In some embodiments the temperature of the aqueous pharmaceutical solution is 4° C.-12° C., or the temperature of the aqueous pharmaceutical solution is reduced to 4° C.-12° C.

In some embodiments the filtering is performed using a sterilizing filter having a pore size of 0.2 µm or less, wherein the first, the second or both filters are a sterilizing filter having a pore size of 0.2 µm or less.

In some embodiments the pharmaceutical preparation in the suitable container is an aqueous pharmaceutical solution comprising 20 mg/ml glatiramer acetate and 40 mg/ml mannitol.

In some embodiments the pharmaceutical preparation in the suitable container is an aqueous pharmaceutical solution comprising 40 mg/ml glatiramer acetate and 40 mg/ml mannitol.

In some embodiments the pharmaceutical preparation in the suitable container is an aqueous pharmaceutical solution having a pH in the range of 5.5-7.0.

In some embodiments the pharmaceutical preparation in the suitable container is an aqueous pharmaceutical solution which is a sterilized aqueous solution which has been sterilized by filtration and without subjecting the aqueous pharmaceutical solution to heat, chemicals, or radiation exposure.

In some embodiments the pharmaceutical preparation is a lyophilized powder of glatiramer acetate and mannitol.

In some embodiments the process further comprises a step of lyophilizing the filtrate after it has been filled into the suitable container so as to form a lyophilized powder of glatiramer acetate and mannitol in the suitable container.

In some embodiments the suitable container is a syringe, vial, ampoule, cartridge or infusion.

In some embodiments the suitable container is a syringe.

In some embodiments the syringe contains 1 ml of an aqueous pharmaceutical solution.

This invention provides a prefilled syringe containing 40 mg of glatiramer acetate and 40 mg mannitol, which syringe is prepared by a process of the invention.

According to any embodiment of the prefilled syringe disclosed herein, the prefilled syringe contains 1 ml of an aqueous pharmaceutical solution of 40 mg/ml of glatiramer acetate and 40 mg/ml mannitol.

According to any embodiment of the prefilled syringe disclosed herein, the aqueous pharmaceutical solution
a) has a viscosity in the range of 2.0-3.5 cPa; or
b) has an osmolality in the range of 270-330 mosmol/Kg.

According to any embodiment of the prefilled syringe disclosed herein, the aqueous pharmaceutical solution a) has a viscosity in the range of 2.2-3.0 cPa; or b) has an osmolality in the range of 275-325 mosmol/Kg.

This invention provides an aqueous pharmaceutical solution comprising 40 mg/ml glatiramer acetate and 40 mg/ml mannitol, wherein the aqueous pharmaceutical solution a) has a viscosity in the range of 2.0-3.5 cPa; or b) has an osmolality in the range of 275-325 mosmol/Kg.

According to some embodiments of the aqueous pharmaceutical solution, the aqueous pharmaceutical solution has a viscosity in the range of 2.0-3.5 cPa.

According to some embodiments of the aqueous pharmaceutical solution, the aqueous pharmaceutical solution has a viscosity in the range of 2.61-2.92 cPa.

According to some embodiments of the aqueous pharmaceutical solution, the aqueous pharmaceutical solution has an osmolality in the range of 275-325 mosmol/Kg.

According to some embodiments of the aqueous pharmaceutical solution, the aqueous pharmaceutical solution has an osmolality in the range of 300-303 mosmol/Kg.

According to some embodiments of the aqueous pharmaceutical solution, the aqueous pharmaceutical solution comprises glatiramer acetate having a viscosity in the range of 2.3-3.2 cPa.

According to some embodiments of the aqueous pharmaceutical solution, the aqueous pharmaceutical solution comprises glatiramer acetate having a viscosity in the range of 2.6-3.0 cPa.

According to some embodiments of the aqueous pharmaceutical solution, the aqueous pharmaceutical solution comprises glatiramer acetate having an osmolality in the range of 290-310 mosmol/Kg.

According to some embodiments of the aqueous pharmaceutical solution, the aqueous pharmaceutical solution comprises glatiramer acetate having an osmolality in the range of 295-305 mosmol/Kg.

According to some embodiments of the aqueous pharmaceutical solution, the aqueous pharmaceutical solution has a pH in the range of 5.5-7.0.

This invention provides a prefilled syringe containing 1 ml of an aqueous pharmaceutical solution prepared by the invention.

This invention provides an automated injector comprising the prefilled syringe prepared by the invention.

This invention provides a method of treatment of a human patient suffering from a relapsing form of multiple sclerosis comprising administration to the human patient of three subcutaneous injections of a 40 mg/ml dose of glatiramer acetate per week using the prefilled syringe of this invention, using the aqueous pharmaceutical solution of this invention, or using the automated injector of this invention so as to treat the human patient.

In some embodiments, the human patient is suffering from relapsing-remitting multiple sclerosis.

In some embodiments, the human patient has experienced a first clinical episode and has MRI features consistent with multiple sclerosis.

This invention provides a process of preparing a pharmaceutical preparation of glatiramer acetate and mannitol in a suitable container comprising the steps of:

(i) obtaining an aqueous pharmaceutical solution of glatiramer acetate and mannitol;

(ii) filtering the aqueous pharmaceutical solution at a temperature of from above 0° C. up to 17.5° C. to produce a filtrate; and (iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the obtaining step (i) comprises compounding the aqueous pharmaceutical solution in a compounding vessel.

In an embodiment, the process further comprises the step of reducing the temperature of the aqueous pharmaceutical solution to a temperature from above 0° C. up to 17.5° C. while in the compounding vessel.

In an embodiment, the process further comprises the step of reducing the temperature of the first filter to a temperature from above 0° C. up to 17.5° C.

In an embodiment, the process further comprises the step of reducing the temperature of the second filter to a temperature from above 0° C. up to 17.5° C.

This invention provides a process of preparing a pharmaceutical preparation of glatiramer acetate and mannitol in a suitable container comprising the steps of:

(i) obtaining an aqueous pharmaceutical solution of glatiramer acetate and mannitol;

(ii) filtering the aqueous pharmaceutical solution at a temperature of from above 0° C. up to 17.5° C. to produce a filtrate; and (iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the obtaining step (i) comprises compounding the aqueous pharmaceutical solution in a compounding vessel.

In an embodiment, the process further comprises the step of reducing the temperature of the aqueous pharmaceutical solution to a temperature from above 0° C. up to 17.5° C. after leaving the compounding vessel and before entering into the first filter.

In an embodiment, the process further comprises the step of reducing the temperature of the first filter to a temperature from above 0° C. up to 17.5° C.

In an embodiment, the process further comprises the step of reducing the temperature of the second filter to a temperature from above 0° C. up to 17.5° C.

This invention provides a process of preparing a pharmaceutical preparation of glatiramer acetate and mannitol in a suitable container comprising the steps of:

(i) obtaining an aqueous pharmaceutical solution of glatiramer acetate and mannitol;

(ii) filtering the aqueous pharmaceutical solution at a temperature of from above 0° C. up to 17.5° C. to produce a filtrate; and (iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the process further comprises the step of reducing the temperature of the second filter to a temperature from above 0° C. up to 17.5° C.

This invention provides a process of preparing a pharmaceutical preparation of glatiramer acetate and mannitol in a suitable container comprising the steps of:
(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the process further comprises the step of reducing the temperature of the first filter to a temperature from above 0° C. up to 17.5° C.

In an embodiment, the process further comprises the step of reducing the temperature of the second filter to a temperature from above 0° C. up to 17.5° C.

This invention provides a process of preparing a pharmaceutical preparation of glatiramer acetate and mannitol in a suitable container comprising the steps of:
(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the obtaining step (i) comprises compounding the aqueous pharmaceutical solution in a compounding vessel.

In an embodiment, the process further comprises the step of reducing the temperature of the aqueous pharmaceutical solution to a temperature from above 0° C. up to 17.5° C. while in the compounding vessel.

This invention provides a process of preparing a pharmaceutical preparation of glatiramer acetate and mannitol in a suitable container comprising the steps of:
(i) obtaining an aqueous pharmaceutical solution of glatiramer acetate and mannitol;
(ii) filtering the aqueous pharmaceutical solution at a temperature of from above 0° C. up to 17.5° C. to produce a filtrate; and
(iii) filling the suitable container with the filtrate obtained after performing step (ii), so as to thereby prepare the pharmaceutical preparation of glatiramer acetate and mannitol in the suitable container.

In an embodiment, the filtering step (ii) comprises filtering the aqueous pharmaceutical solution through a first filter, and a second filter.

In an embodiment, the filtering step (ii) further comprises the step of receiving the aqueous pharmaceutical solution filtered through the first filter in a receiving vessel.

In an embodiment, the process further comprises the step of reducing the temperature of the aqueous pharmaceutical solution to a temperature from above 0° C. up to 17.5° C. while in the receiving vessel.

Automated Injection Device

The mechanical workings of an automated injection assisting device can be prepared according to the disclosure in European application publication No. EP0693946 and U.S. Pat. No. 7,855,176, which are incorporated herein by reference.

All combinations of the various elements described herein are within the scope of the invention.

DEFINITIONS

As used herein, "glatiramer acetate" is a complex mixture of the acetate salts of synthetic polypeptides, containing four naturally occurring amino acids: L-glutamic acid, L-alanine, L-tyrosine, and L-lysine. The peak average molecular weight of glatiramer acetate is between 5,000 and 9,000 daltons. Chemically, glatiramer acetate is designated L-glutamic acid polymer with L-alanine, L-lysine and L-tyrosine, acetate (salt). Its structural formula is:

(Glu,Ala,Lys,Tyr)$_x$.X CH3COOH

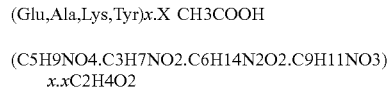

x.xC2H4O2

CAS-147245-92-9

As used herein "glatiramer acetate drug substance" is the glatiramer acetate active ingredient prior to its formulation into a glatiramer acetate drug product.

As used herein, a "glatiramer acetate drug product" is a formulation for pharmaceutical use which contains a glatiramer acetate drug substance. Copaxone® is a commercial glatiramer acetate drug product manufactured by TEVA Pharmaceutical Industries Ltd. (Israel), which is described in Copaxone, Food and Drug Administration Approved Labeling (Reference ID: 3443331) [online], TEVA Pharmaceutical Industries Ltd., 2014 [retrieved on Dec. 24, 2014], Retrieved from the Internet: <URL: www.accessdata.fda.gov/drugsatfda_docs/label/2014/020622s0891bl.pdf>, the contents of which are hereby incorporated by reference. Copaxone® is available as 20 mg/mL administered once per day, and/or 40 mg/ml administered three times per week.

As used herein, a "sterilizing filter" is a filter with a pore size of 0.2 μm or less which will effectively remove microorganisms.

By any range disclosed herein, it is meant that all hundredth, tenth and integer unit amounts within the range are specifically disclosed as part of the invention. Thus, for example, 1 mg to 50 mg means that 1.1, 1.2 . . . 1.9; and 2, 3 . . . 49 mg unit amounts are included as embodiments of this invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Methods

Glatiramer Acetate (GA) Injection 40 mg/mL in a prefilled syringe (GA injection 40 mg/mL in PFS or Copaxone® 40 mg/mL) was developed as a new formulation of the active ingredient glatiramer acetate, which is also used in the marketed product Copaxone 20 mg/mL solution for injection in a prefilled syringe. Copaxone® 40 mg/mL is to be administered three times a week by subcutaneous injection to patients with Relapsing Remitting Multiple Sclerosis. The new formulation is based on the formulation of the marketed Copaxone® 20 mg/mL solution for injection in a prefilled syringe. Copaxone® 20 mg/mL is an approved product, the safety and efficacy of which are supported by over two decades of clinical research and over a decade of post-marketing experience. The only difference between the formulations is the double amount of the active substance used, which results in a solution with double the concentration of glatiramer acetate (40 mg/mL vs. 20 mg/mL). The amount of mannitol in both Copaxone® formulations remains unchanged (40 mg/mL).

The compositions of Copaxone® 20 mg/mL and Copaxone® 40 mg/mL are detailed in Table 1.

TABLE 1

Compositions of Copaxone ® 20 mg/mL and Copaxone ® 40 mg/mL

| Components | Copaxone ® 20 mg/mL Content per mL | Copaxone ® 40 mg/mL |
|---|---|---|
| Glatiramer Acetate[1] | 20.0 mg | 40.0 mg |
| Mannitol USP/Ph. Eur. | 40.0 mg | 40.0 mg |
| Water for Injection USP/Ph. Eur/JP | q.s. to 1.0 mL | q.s. to 1.0 mL |

[1]Calculated on the dry basis and 100% assay

Studies were conducted in order to verify that the formulation of Copaxone® 40 mg/mL, its manufacturing process and chemical, biological and microbiological attributes are appropriate for commercialization. Studies were also conducted to confirm the suitability of the proposed container closure system for packaging Copaxone® 40 mg/mL.

Mannitol was chosen as the tonicity agent for the initially formulated Copaxone® (freeze dried product, reconstituted prior to administration) as it is also a bulking agent. When the currently marketed ready-to-use formulation of Copaxone® 20 mg/mL solution for injection prefilled syringe was developed, mannitol was used in this formulation as well, as the osmoregulator. Finally, when the new 40 mg/mL formulation was developed, based on the Copaxone® 20 mg/mL formulation, mannitol remained as the osmoregulator.

Mannitol is widely used in parenteral formulations as an osmoregulator. It is freely soluble in water and stable in aqueous solutions. Mannitol solutions may be sterilized by filtration. In solution, mannitol is not affected by atmospheric oxygen in the absence of catalysts. The concentration of mannitol in the Copaxone® 40 mg/mL is 40 mg/mL. Maintaining the mannitol concentration in Copaxone® 40 mg/mL resulted in an essentially isotonic solution.

Water for injection (WFI) is the most widely used solvent and inert vehicle in parenteral formulations. Water is chemically stable in all physical states. It is the base for many biological life forms, and its safety in pharmaceutical formulations is unquestioned.

Example 1

The manufacturing process of Copaxone® 40 mg/mL comprises:
  Compounding a bulk solution of GA and mannitol in water for injections (WFI).
  Sterilizing filtration of the bulk solution yielding the sterile GA solution in bulk.
  Aseptic filling of sterile bulk solution into syringe barrels and stoppering.
  Inspection and final assembly of the filled syringes.

Initially, filtration of bulk solution from the compounding vessel was performed through a sequential filter train consisting of two sequential sterilizing filters (filters named $A_1$ and $A_2$, respectively) to a receiving vessel. From the receiving vessel it was transferred to the intermediate vessel in the filling machine and further through dosing pumps and needles into prefilled syringes. However, due to a Health Authority request to place the sterilizing filter as close as possible to the filling point, the second sterilizing filter was moved between the receiving and intermediate vessels. In the current filtration train, the first sterilizing filter was named Filter A, and the second relocated sterilizing filter was named Filter B. See, FIG. 1.

In line with the process for the approved Copaxone® 20 mg/mL formulation, all processing steps of the new Copaxone® 40 mg/mL formulation were originally conducted at controlled room temperature. However, filtration of the higher concentration solution resulted in a pressure build-up on the second filter, Filter B. Despite the observed pressure increase on Filter B, a high-quality drug product could be obtained by filtration of GA 40 mg/mL at controlled room temperature, as confirmed by release and stability data. Nevertheless, an improved filtration process was needed which avoided the build-up on the second filter.

Flow rate for fluids can be defined by the differential pressure, and inversely moderated by viscosity. Viscosity, in turn, is usually reciprocal in relation to temperature (Meltzer and Jornitz, *Filtration and Purification in the Biopharmaceutical Industry*, Second Edition, CRC Press, 2007, page 166). Increasing the temperature of a solution will normally decrease the viscosity, thereby enhancing the flow rate.

In an attempt to solve the pressure build-up problem on the second filter, the temperature condition of the filtration was raised above controlled room temperature. Although the viscosity decreased, the filterability decreased, resulting in a failed attempt.

The following studies were performed:
  Filter Validation Study: Determination of ranges for the manufacturing parameters related to sterilizing Filter A and sterilizing Filter B of the bulk solution, as well as confirmation of filter compatibility with the drug product.
  Filtration Process: Selection of the sterilizing filtration conditions best suitable for the manufacturing process and the quality of the drug product.
  Filters Used for Copaxone® 20 mg/mL and Copaxone® 40 mg/mL Manufacturing The manufacturing process of Copaxone® 40 mg/mL was based on the process used to produce the marketed Copaxone® 20 mg/mL solution for injection in a prefilled syringe. Therefore the same filters used for filtration of marketed product were used.

Two sterilizing filters were used, each of which having a pore size of 0.2 μm or less, to effectively remove microorganisms. Sterilization is achieved only by filtration using sterilizing filters and not by using other methods, e.g. sterilization is achieved without using heat, chemicals, or radiation exposure.

Filter Validation Study—Confirmation and Setting of Parameters Associated with Filter Compatibility and with Sterilizing Filtration The following tests were performed in order to confirm the filter validity:
  Extractables testing—assessment of extractables released from the filter upon steam sterilization and their removal from the filter by a model solvent, thus assessing the volume to be discarded after the filtration through the Filter B, prior to beginning of the aseptic filling.

Compatibility/adsorption testing—assessment of the chemical compatibility of GA 20 mg/mL and GA 40 mg/mL solution with the filter material and the extent of its adsorption to the filter, thus assessing the volume to be discarded after the filtration through Filter B, prior to beginning of the aseptic filling in order to provide assay within specifications.

Residual effect—To ensure that no significant residual GA 20 mg/mL or GA 40 mg/mL solution that might affect the post use integrity test remains on the filter after filtration.

Bacterial challenge—To ensure that the filtration process does not affect the ability of the filter to provide a sterile solution.

The above tests were conducted using maximum pressure (up to 5.0 bar). The validation study demonstrated that the selected filtration system is capable of providing a high quality Copaxone® 20 mg/mL and Copaxone® 40 mg/mL.

Given the strict and well-defined operational and equipment parameters of the GA 40 mg/mL solution filtration process, a plan to mitigate the potential increase in pressure by reducing the filtration temperature was developed.

Without much expectations, it was decided to examine the filtration process of GA 40 mg/mL sterile bulk solution through Filter B under reduced temperature conditions, using the same filters and filtration train as for the filtration at controlled room temperature.

Accordingly, experiments were performed in order to compare the filtration of GA 40 mg/mL sterile bulk solution through Filter B under reduced temperature and controlled room temperature in the production environment and to ensure that there is no difference with regard to the quality and stability profiles of the filtered solutions. In all experiments, the sterile bulk solution was prepared according to the standard compounding and filtration train (see FIG. 1) and filtered through two filters: Filter A and Filter B.

Figure 2:
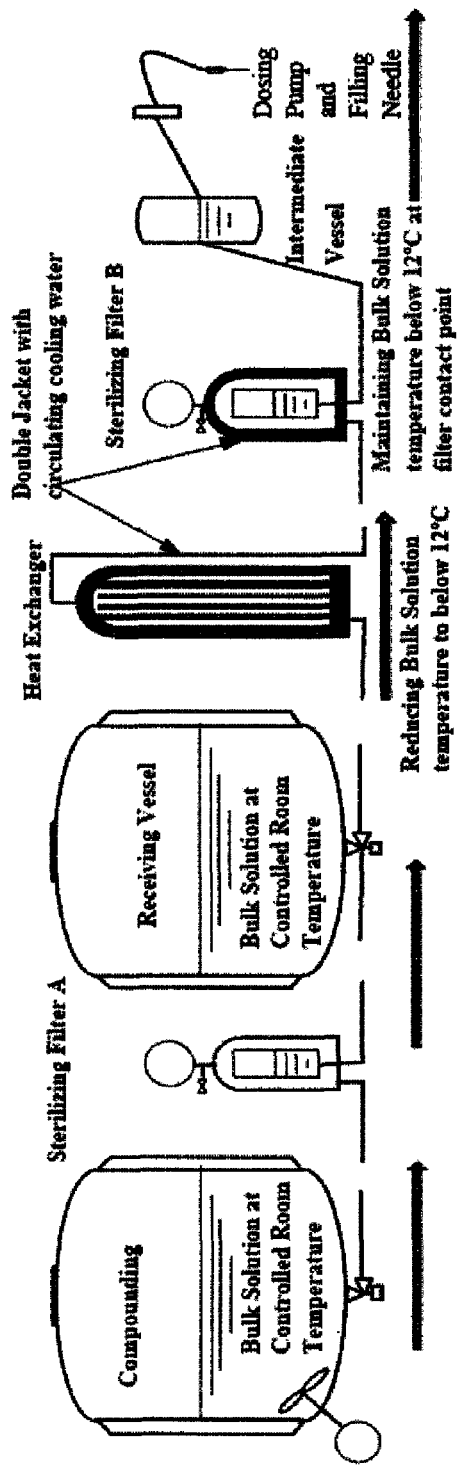
FIG. 2. Schematic description of filtration process by heat exchanger and cooled filter housing.

The experiments tested two different cooling technologies (cooled receiving vessels vs heat exchanger) with cooled filter. The studies are schematically depicted in FIG. 1 and FIG. 2. Further details about these experiments and their outcomes are provided hereafter.

Filtration Process—Experiment No. 1

The objective of Experiment No. 1 was to compare the filterability of a batch of bulk solution held and filtered through Filter B at either controlled room temperature or under reduced temperature conditions (cooling by double-jacketed receiving vessel and cooled Filter B housing).

Figure 3:
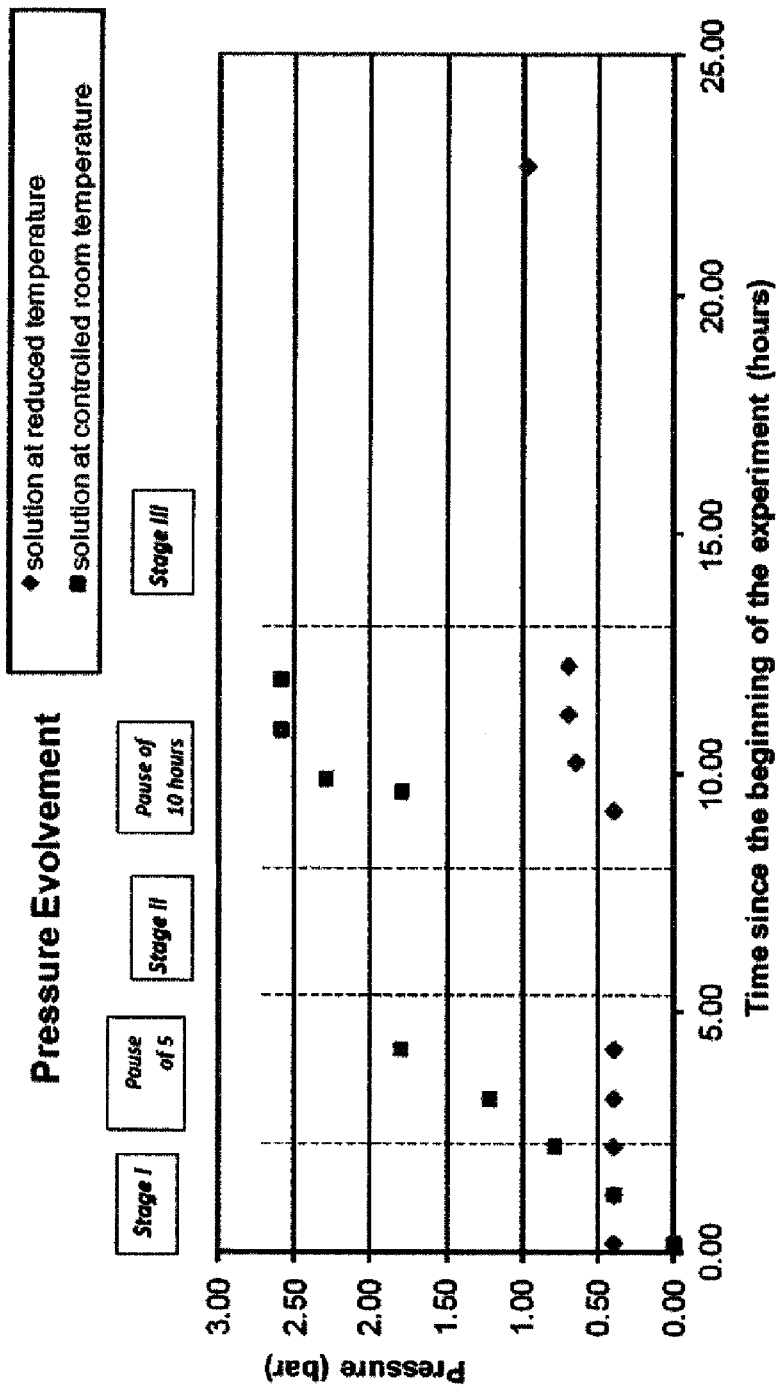
FIG. 3. Pressure record for Experiment No. 1. * Filtration of GA solution at controlled room temperature was stopped and the remaining solution was transferred to the cooled receiving vessels.

The study is schematically depicted in FIG. 1. The experimental design and the obtained results are summarized in Table 2 and FIG. 3.

TABLE 2

Experimental Design and Results for Experiment No. 1.

| Experiment Outline | Reduced Temperature Filtration | Controlled Room Temperature Filtration |
|---|---|---|
| Compounding | According to standard manufacturing procedure[1] | |
| Holding time in the receiving vessel | 13 hours | 13 hours |
| Temperature of solution held in the receiving vessel | 6.6-10.7° C.[2] | 17.8-24.6° C. |
| Planned regimen for filtration though Filter B[3] | Intermittent filtration: Stage I - 5 filtration steps of filtration of about 10 liters of bulk solution - followed by pauses of about 50 minutes each, followed by a pause of 5 hours. Stage II - 4 filtration steps of filtration of about 10 liters of bulk solution - followed by pauses of about 50 minutes each, followed by a pause of about 10 hours. Stage III - Filtration of remaining solution. | |
| Total volume of bulk solution filtered | About 125 L. Filtration was completed. | About 85 liters. Filtration was stopped due to increase in pressure on Filter B. |

[1]One bulk solution was prepared and divided into two portions. Bulk solution size: 230 liters. Filtration of solution at controlled room temperature was stopped after 85 liters have been pushed through the filter due to increased pressure and the remaining solution was transferred to the cooled receiving vessels.
[2]The temperature increased (to 14.9° C.) once during the filtration following the addition of the remaining solution kept at ambient temperature.
[3]The filtrations were carried out in parallel.

Surprisingly, filtration at reduced temperature allowed filtration to be completed without the pressure increase associated with filtration at controlled room temperature.

Example 2

Filtration Process—Experiment No. 2

The first objective of Experiment No. 2 was to evaluate whether local cooling of GA 40 mg/mL solution using a Heat Exchanger (HE) could improve the filterability through cooled Filter B compared to filterability of the same bulk solution at controlled room temperature.

The second objective of Experiment No. 2 was to confirm that there is no difference in the quality of the drug product filled into syringes at controlled room temperature and drug product filled into syringes at reduced temperature.

Cooling by heat exchanger was evaluated as it seemed to be much easier to steam sterilize than using the double jacketed receiving vessels. The HE was located between the receiving vessel and Filter B. Consequently, as opposed to Experiment No. 1 (in which the solution was cooled by the double-jacketed receiving vessels following filtration through Filter A and kept cooled prior to filtration through Filter B), the solution in this experiment was held at controlled room temperature prior to filtration of the locally cooled (by HE) GA solution through Filter B.

Figure 4:
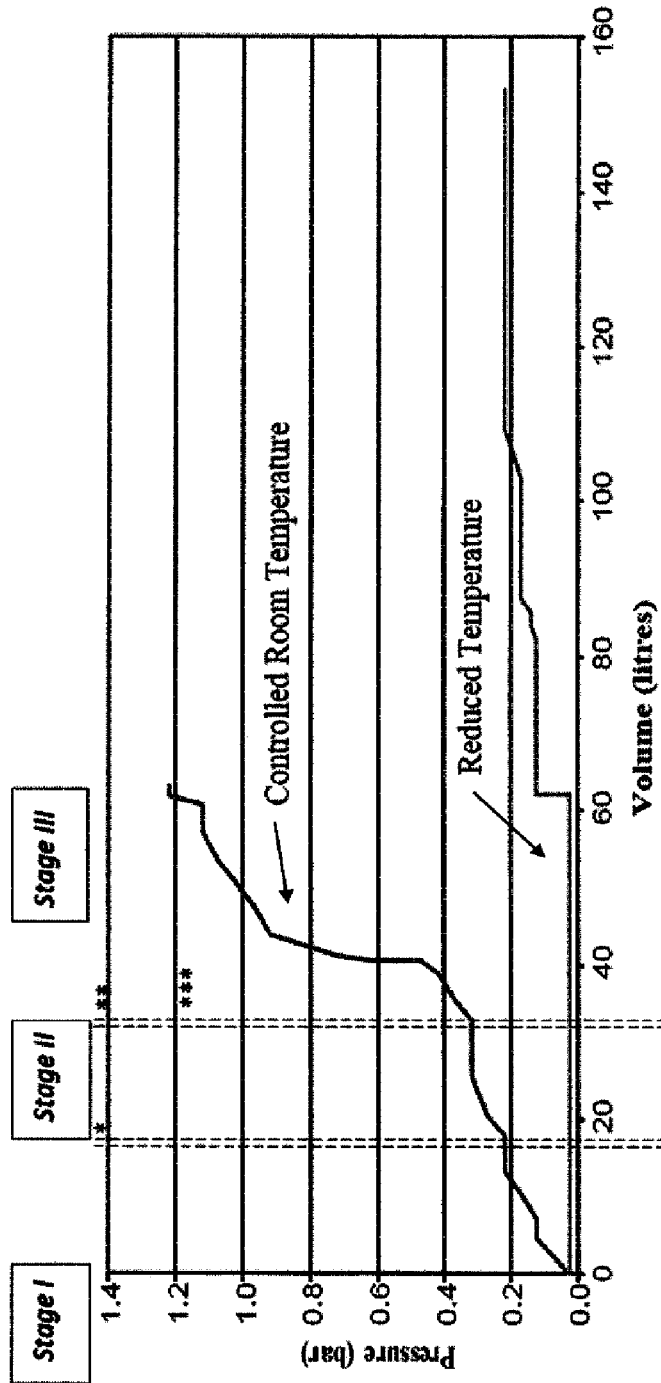
FIG. 4. Pressure record for Experiment No. 2. * Pauses of 3 hours and 5 hours for GA solutions filtered at controlled room temperature and at reduced temperature, respectively.  Pause of 10 hours for both GA solutions. * Filtration of GA solution at controlled room temperature was stopped. Remaining GA solution was filtered at reduced temperature.
Figure 5:
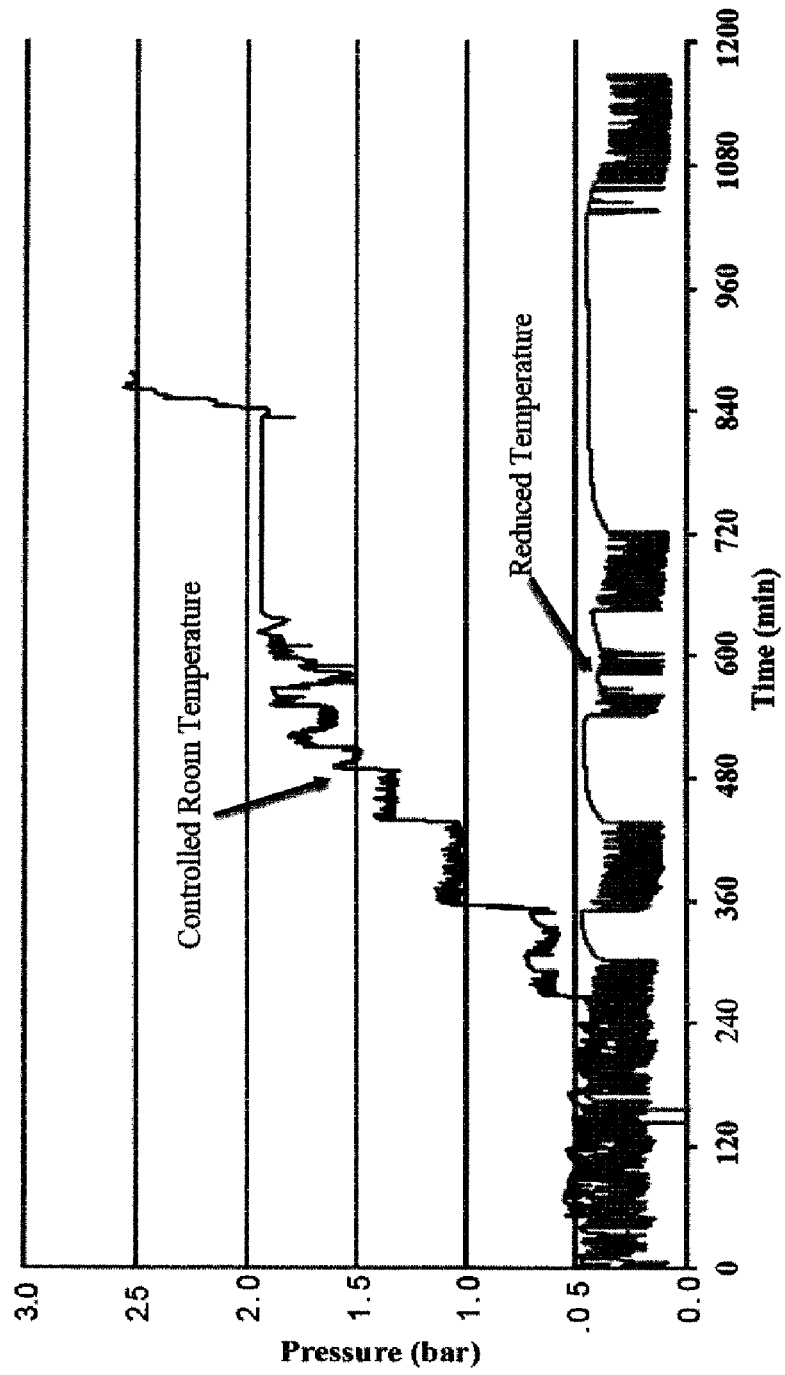
FIG. 5. Pressure record for Experiment No. 3.

The study is schematically depicted in FIG. 2. The experimental design and the obtained results are summarized in Table 3. The pressure observed over the course of the filling process of Experiment No. 2 is shown in FIG. 4.

TABLE 3

Experimental Design and Results for Experiment No. 2.

| Experiment Outline | Reduced Temperature Filtration | Controlled Room Temperature Filtration |
|---|---|---|
| Compounding | According to standard manufacturing procedure[1] | |
| Filtration into a receiving vessel | Filtration of all the bulk solution through Filter A into a receiving vessel held at controlled room temperature | |
| Temperature of solution held in the receiving vessel | Controlled room temperature | |
| Holding time in the receiving vessel | 19 hours | |
| Planned regimen for filtration through Filter B | The solution is locally cooled as it is transferred through a HE and filtered through cooled Filter B. Three consecutive filtration and filling stages. About 3 hours break between Stage I and Stage II and about 10 hours break between Stage II and Stage III. | The solution is filtered through Filter B at controlled room temperature. Three consecutive filtration and filling stages. About 5 hours break between Stage I and Stage II and about 10 hours break between Stage II and Stage III. |
| Temperature of solution transferred through the HE | 6.4-12° C. | No use of HE |
| Duration of filtration through Filter B[2] | 24 hours | 19 hours |
| Temperature of solution transferred through Filter B | 5.7-8.8° C. | Ambient temperature |
| Total volume of bulk solution filtered and filled into syringes | 154 L | 63 L[3] |
| Storage conditions during stability studies | Long term (2-8° C.) Accelerated (25° C./60% RH) - completed 6 months Stress (40° C./75% RH) - completed 3 months | |
| Stability data | The stability data showed that the drug product has a similar stability profile when it is filtered at controlled room temperature or under reduced temperature conditions. Both filtration processes demonstrate similar impurity profiles. | |

[1]One bulk solution was prepared and divided into two portions. Bulk solution size: 230 liters.
[2]Both filtration processes (reduced and controlled room temperature) were carried out in parallel for comparison. At each stage, filtration was carried out at controlled room temperature, followed by filtration at reduced temperature.
[3]Filtration of solution at controlled room temperature was stopped due to pressure increase and the remaining solution was filtered at reduced temperature.

Example 3

Filtration Process—Experiment No. 3

One objective of Experiment No. 3 was to confirm whether cooling of GA 40 mg/mL bulk solution prior to filtration, using HE and cooled filter housing, allows filtration and filling of batches of 130 L size within various manufacturing regimens.

Another objective of Experiment No. 3 was to evaluate the influence of holding time at various stages of the manufacturing process on filterability of GA 40 mg/mL.

Another objective of Experiment 3 was to demonstrate with a high degree of assurance that locally cooled GA 40 mg/mL solution filtered through Filter B is not different in its quality and stability profile from GA 40 mg/mL solution filtered through Filter B at controlled room temperature conditions with regard to pre-determined parameters and limits.

A series of three batches of bulk solution, manufactured at various regimens, were prepared. Each bulk solution was prepared from an identical combination of the same three drug substance batches.

The experimental design and results are summarized in Table 4.

TABLE 4

Experimental Design and Results for Experiment No. 3

| Experiment Outline | Reduced Temperature Filtration | Controlled Room Temperature Filtration | Reduced Temperature Filtration | Controlled Room Temperature Filtration |
|---|---|---|---|---|
| Batch No. | A | A-2[1] | B | C |
| Compounding | Standard compounding | Standard compounding | Standard compounding | Standard compounding |
| Batch size | First 130 L from bulk solution A | Remaining 50 L from bulk solution A | 180 L | 180 L |
| Holding time in the compounding vessel[2] | 4 hours | 4 hours (same bulk solution as A) | 8 hours | 3.5 hours |
| Holding time in the receiving vessel[3] | 1.5 hours | 10.5 hours[4] | 16 hours | 13 hours |
| Duration of filtration through Filter B | 7 hours | 3 hours | 19.5 hours | 13 hours |
| Total duration of entire process (total holding time) | 12.5 hours | 17.5 hours | 43.5 hours | 29.5 hours |

TABLE 4-continued

Experimental Design and Results for Experiment No. 3

| Experiment Outline | Reduced Temperature Filtration | Controlled Room Temperature Filtration | Reduced Temperature Filtration | Controlled Room Temperature Filtration |
|---|---|---|---|---|
| Temperature range before Filter B | 10.4-12.2° C. | Controlled room temperature | 10.2-11.7° C. | Controlled room temperature |
| Temperature range after Filter B | 9.3-11.0° C. | Controlled room temperature | 9.0-10.2° C. | Controlled room temperature |
| Maximum pressure before Filter B | 0.6 bar | 0.3 bar | 0.6 bar | 2.5 bar[5] |
| Total volume filled into syringes | 130 L | 50 L | 180 L | 134 L |
| Storage conditions during stability studies | Long term (2-8° C.) Accelerated (25° C./60% RH) Stress (40° C./60% RH) | Stress (40° C./60% RH) | Long term (2-8° C.) Accelerated (25° C./60% RH) Stress (40° C./60% RH) | Long term (2-8° C.) Accelerated (25° C./60% RH) Stress (40° C./60% RH) |
| Stability data and conclusions | Stability data showed that the drug product has a similar stability profile at all three storage conditions, regardless of whether it is filtered at controlled room temperature or under reduced temperature conditions. Both filtration processes result in product having substantially the same degradation and impurity profile at stress conditions. | | | |

[1]Batches A and A-2 are from the same bulk solution. Filter B was replaced with a new filter prior to filtration of A-2.
[2]Compounding and subsequent holding time in the compounding vessel (incl. filtration through filter A).
[3]Time from end of filtration through Filter A to beginning of filtration through Filter B and filling.
[4]Since A-2 was filtered and filled into syringes subsequent to the filtration and filling of A, the stated holding time represents the sum of the holding time of A in addition to the time A-2 was held until the filtration at controlled room temperature was initiated.
[5]Throughout the filling, gradual increase of filtration pressure was required in order to maintain flow rate that would correspond to the rate required for continuous filling.

Based on the results of Experiment No. 3, it was confirmed that local cooling by heat exchanger is sufficient in order to enable filtration of a 130 L batch. In addition, the quality and stability profile of GA 40 mg/mL solutions filtered at controlled room temperature and reduced temperature were found to be substantially identical.

Example 4

Figure 6:
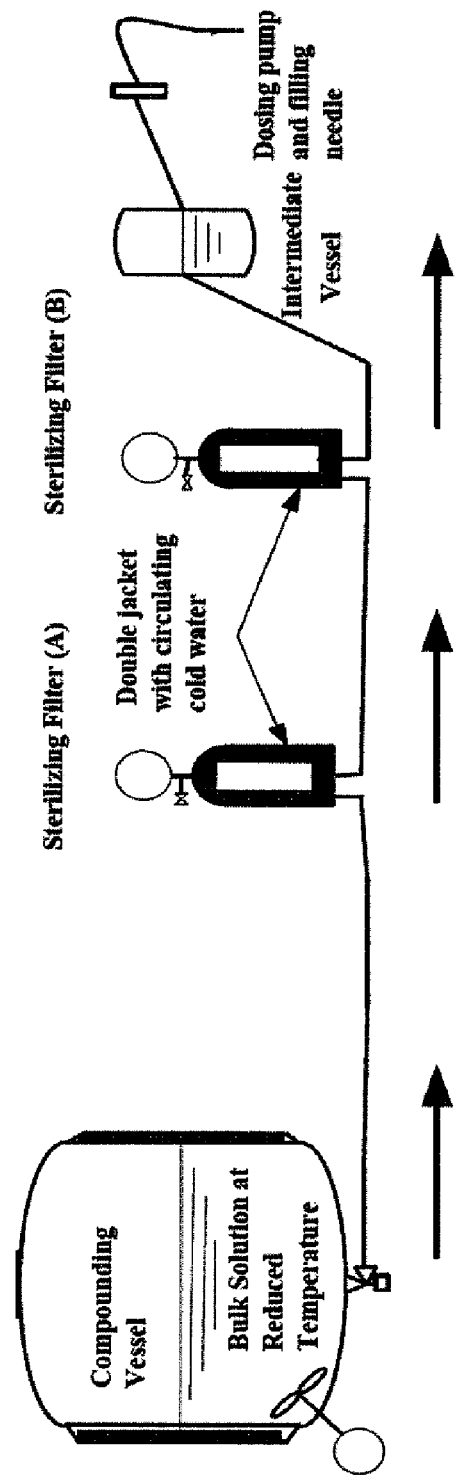
FIG. 6. Schematic description of filtration process by cooled compounding vessel and cooled filter housings on both Filter A and Filter B.

Cooling of GA 40 mg/mL bulk solution below 17.5° C. in the compounding vessel before passing through cooled Filter A and cooled Filter B in sequence (see FIG. 6) results in lower pressure during the filtration step of both Filter A and Filter B as compared to the holding the same bulk solution in the compounding vessel and passing it through Filter A and Filter B at controlled room temperature (Cooling of the bulk solution by using double jacketed compounding vessel and cooling the filters by using double jacketed filter housings).

Reducing the temperature of the GA 40 mg/mL bulk solution in the compounding vessel and passing it through cooled Filter A and Filter B in sequence (see FIG. 6) significantly reduces impairment of filterability caused by the total duration of the process (holding time) as well as by filtering larger volume, compared to the same bulk solution held and filtered under controlled room temperature.

Example 5

Figure 7:
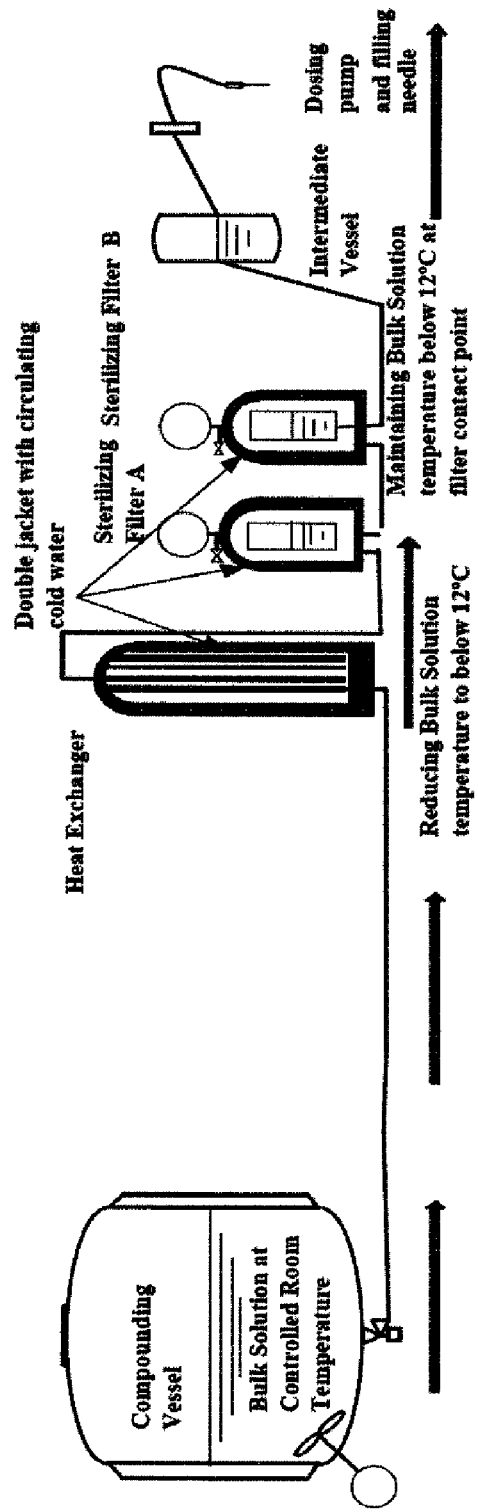
FIG. 7. Schematic description of filtration process by heat exchanger and cooled filter housings on both Filter A and Filter B.

Local cooling of GA 40 mg/mL bulk solution by a heat exchanger and passing the solution through cooled Filter A and cooled Filter B in sequence (see FIG. 7) results in lower pressure during the filtration step of both Filter A and Filter B as compared to passing the same bulk solution held and filtered under controlled room temperature.

Reducing the temperature of the GA 40 mg/mL bulk solution using a heat exchanger and passing it through cooled Filter A and cooled Filter B in sequence (see FIG. 7) significantly reduces impairment of filterability caused by the total duration of the process (holding time) as well as by filtering larger volume, compared to the same bulk solution held and filtered under controlled room temperature.

Example 6

Figure 8:
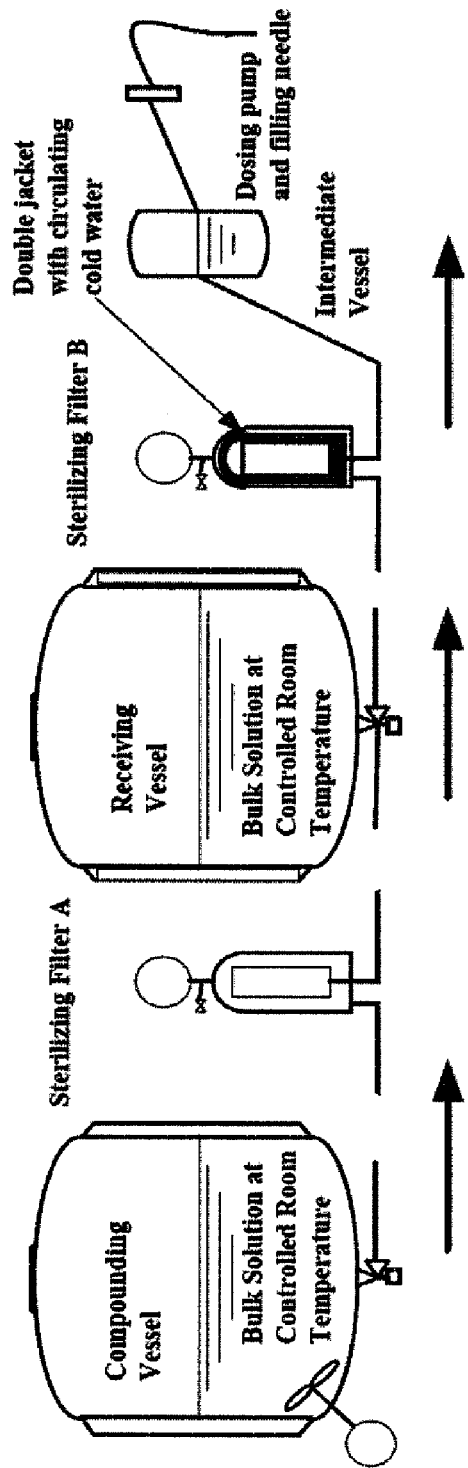
FIG. 8. Schematic description of filtration process by cooled filter housing on only Filter B.

Passing the sterilized GA 40 mg/mL bulk solution from the receiving vessel through cooled Filter B (see FIG. 8) significantly results in lower pressure during the filtration step compared to passing the same bulk solution filtered through Filter B under controlled room temperature.

Passing the sterilized GA 40 mg/mL bulk solution from the receiving vessel through cooled Filter B (see FIG. 8) significantly reduces impairment of filterability caused by the total duration of the process (holding time) as well as by filtering larger volume, compared to the same bulk solution held and filtered under controlled room temperature.

Example 7

Figure 9:
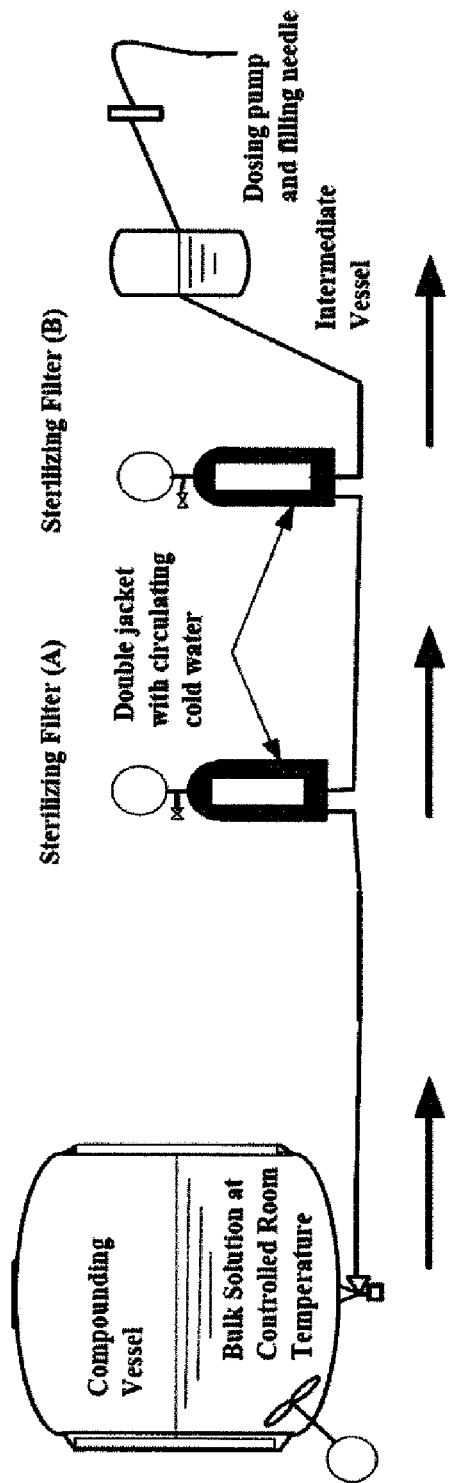
FIG. 9. Schematic description of filtration process by cooled filter housings on both Filter A and Filter B.

Passing GA 40 mg/mL bulk solution from the compounding vessel through cooled Filter A and cooled Filter B in sequence (see FIG. 9) results in lower pressure during the filtration step of both Filter A and Filter B as compared to passing the same bulk solution filtered under controlled room temperature.

Passing GA 40 mg/mL bulk solution from the receiving vessel through cooled Filter A and Filter B in sequence (see FIG. 9) significantly reduces impairment of filterability caused by the total duration of the process (holding time) as well as by filtering larger volume, compared to the same bulk solution filtered under controlled room temperature.

Example 8

Figure 10:
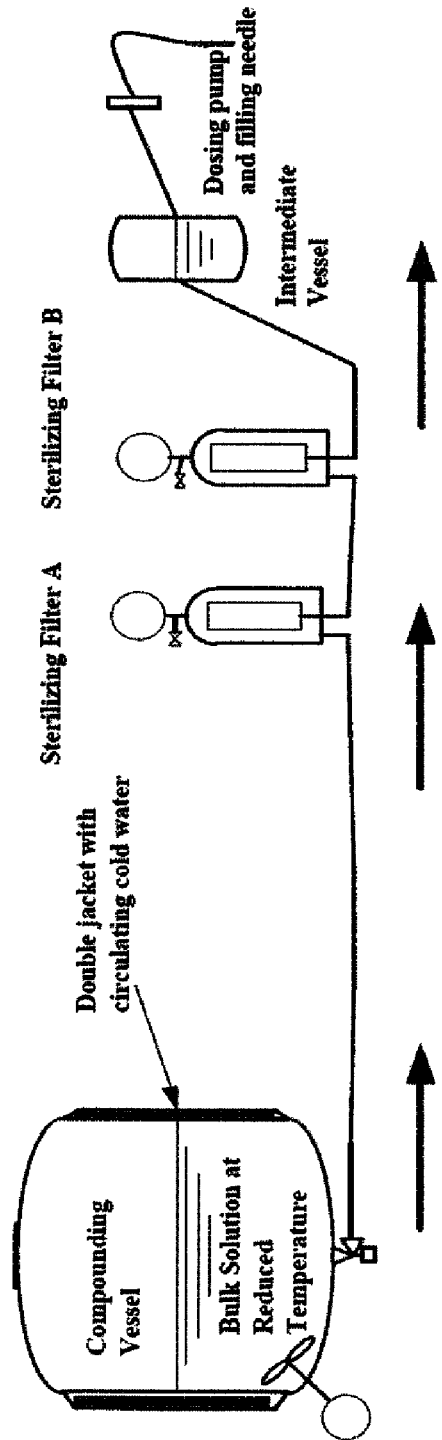
FIG. 10. Schematic description of filtration process by cooled compounding vessel.

Cooling of GA 40 mg/mL bulk solution below 17.5° C. in the compounding vessel before passing through Filter A and Filter B in sequence (see FIG. 10) results in lower pressure during the filtration step of both Filter A and Filter B as compared to the holding the same bulk solution in the compounding vessel and passing it through Filter A and Filter B at controlled room temperature (Cooling of the bulk solution by using double jacketed compounding vessel).

Reducing the temperature of the GA 40 mg/mL bulk solution in the compounding vessel and passing it through Filter A and Filter B in series (see FIG. 10) significantly reduces impairment of filterability caused by the total duration of the process (holding time) as well as by filtering larger volume, compared to the same bulk solution held and under controlled room temperature.

Example 9

Figure 11:
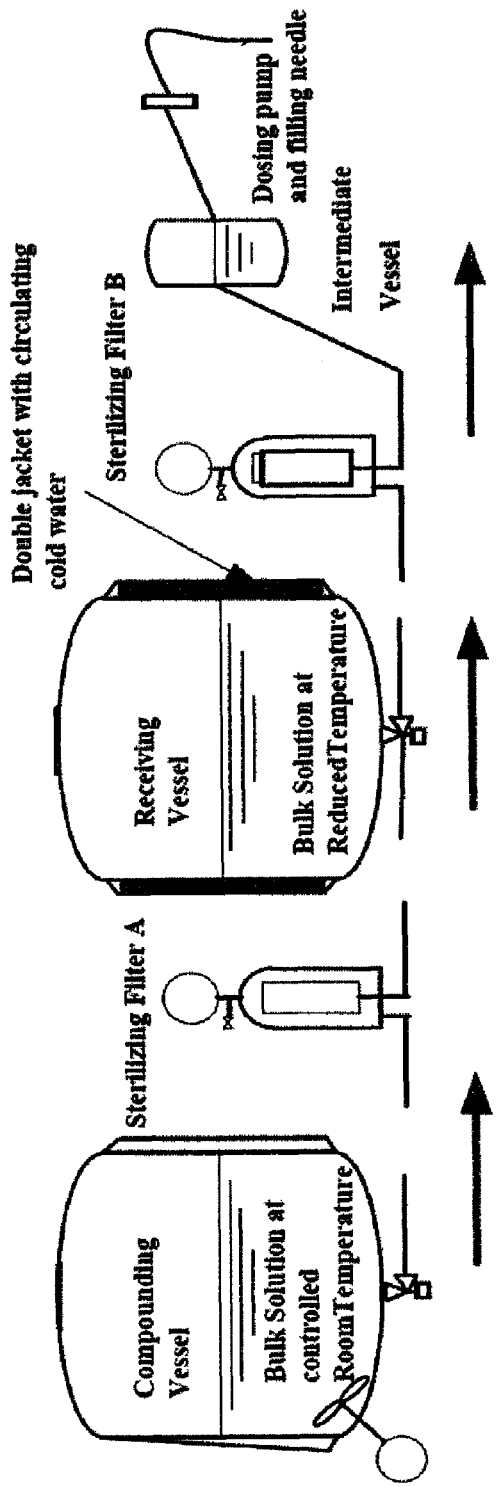
FIG. 11. Schematic description of filtration process by cooled receiving vessel.

Cooling of GA 40 mg/mL bulk solution below 17.5° C. in the receiving vessel before passing through Filter B (see FIG. 11) results in lower pressure during the filtration step of Filter B as compared to the holding the same bulk solution in the compounding vessel at controlled room temperature (Cooling of the bulk solution by using double jacketed compounding vessel).

Reducing the temperature of the GA 40 mg/mL bulk solution in the receiving vessel (see FIG. 10) significantly reduces impairment of filterability caused by the total duration of the process (holding time) as well as by filtering larger volume, compared to the same bulk solution held under controlled room temperature.

Discussion of Examples 1-9

Reducing the temperature of GA 40 mg/mL sterile bulk solution significantly improved its filterability, as demonstrated by the much lower increase in pressure on Filter B during filtration and filling and by the larger volume that can be filtered at reduced temperature. Pressure increases were observed when the sterile bulk solution was held and filtered at controlled room temperature, while there was no significant increase in the pressure when the solution was filtered under reduced temperature conditions.

The holding time of the bulk solution during filtration through Filter B negatively affects the filterability of the solution. However, the total duration of the process (holding time) impaired the filterability significantly less when filtration was performed under reduced temperature conditions. Consequently, longer holding time can be used with reduced temperature filtration.

Both cooling of the solution by passing it through a heat exchanger (local cooling) and/or cooling of the whole bulk (e.g. by double-jacketed receiving vessel) before filtration through cooled Filters A or B or A and B were found to be suitable solutions for reduced temperature filtration.

Accumulated stability data indicate that there is no substantial difference with regard to quality and stability profile between the solution filtered under reduced temperature conditions and the solution filtered at controlled room temperature.

In sum, the performed experiments show that reduced temperature filtration through Filter B significantly improved the filterability of GA 40 mg/mL solution compared to the filterability of the solution when filtered at controlled room temperature. Moreover, reducing the temperature of the bulk solution during the compounding stage or before passing through Filter A, or reducing the temperature of Filter A also improves the filterability of GA 40 mg/mL solution compared to the filterability of the solution at controlled room temperature.

Consequently, the proposed manufacturing process for commercial batches of GA 20 mg/mL and GA 40 mg/mL includes cooling of the solution prior to filtration of the bulk solution through Filter B.

Example 10

Container Closure System

The container closure systems selected for the Copaxone® 40 mg/mL are the same as those used for the marketed product Copaxone® 20 mg/mL PFS. The container closure system consists of a colorless glass barrel, a plastic plunger rod and a grey rubber stopper.

Long Term and Accelerated Stability Studies

Satisfactory stability data after up to 36 months storage under long-term storage conditions (5° C.±3° C.) and after 6 months storage under accelerated conditions (25°±2° C./60±5% RH) are available. The data demonstrate that the proposed container closure systems are suitable for protection and maintenance of the drug product quality throughout its proposed shelf-life.

Protection from Light

Marketed Copaxone® should be stored protected from light. Based on this recommendation, it is proposed that Copaxone® 40 mg/mL be similarly packed in PVC transparent blisters inside a carton box, which provides light protection. The light protection of the proposed packaging when used for the Copaxone® 40 mg/mL is recommended in accordance with the results obtained from a photostability study comparing the following packaging configurations:

1. Glass barrel syringe and plunger rod (Primary package);
  Glass barrel syringe and plunger rod in a transparent blister (partial secondary package);
  Glass barrel syringe and plunger rod in a transparent blister inside carton box (complete intended packaging configuration).

As a reference, the following configurations were added:
2. Glass barrel syringe and plunger rod wrapped in aluminum foil;
  Glass barrel and plunger rod in a transparent blister wrapped in aluminum foil.

All packages were simultaneously exposed to standardized sunlight (5 KLUX) for 10 days and to near UV light for additional 5 days.

All the obtained results from the photostability study are within the specifications. However, the impurity peak detected is lower when the drug product is packed in its complete packaging configuration. The carton box was shown to improve the photostability and gives light protection as good as that of aluminum foil, which is regarded as a complete light protector. The intended packaging configuration is therefore considered suitable for its use.

A storage statement to protect the product from light exposure should be added to the product label.

Microbiological Attributes

The medicinal product is a sterile, single dose, parenteral dosage form. Sterilization is achieved by sterile filtration.

A microbial limits test is performed for the drug substance. The sterility and bacterial endotoxins are monitored upon release and throughout stability studies of the drug product, using pharmacopoeia methods. The limits applied are identical to those applied for the marketed Copaxone®.

The same container closure systems are used for the Copaxone® 20 mg/mL and Copaxone® 40 mg/mL. The integrity testing studies performed to demonstrate the efficacy of the container closure systems on use for the marketed product are also considered relevant for Copaxone® 40 mg/mL.

Example 11

Viscosity

The average viscosity of batches of Copaxone® 20 mg/mL filtered under controlled room temperature and the average viscosity of batches of Copaxone® 40 mg/mL filtered under reduced temperature were obtained and compared. The average viscosity of different batches of Copaxone® 20 mg/mL filtered under controlled room temperature are reported in Table 5. The average viscosity of different batches of Copaxone® 40 mg/mL filtered under reduced temperature are reported in Table 6.

TABLE 5

Viscosity of Batches of Copaxone ® 20 mg/mL Filtered Under Controlled Room Temperature

| Batch No. | Average Viscosity [cPa] | Standard Deviation |
|---|---|---|
| 1 | 1.92[1] | 0.03 |
| 2 | 1.58[1] | 0.00 |
| 3 | 1.58[1] | 0.00 |
| 4 | 1.57[2] | 0.00 |
| 5 | 1.67[2] | 0.01 |
| Water for Injection | 0.93[2] | 0.00 |
| Average | 1.664 | |

[1]Each value is an average of 3 individual results. Values obtained using Rheocalc V2.5 Model LV, Spindle CP40, speed 80 rpm, Shear Rate 600 1/sec, Temperature 25° C. ± 0.1
[2]Each value is an average of 6 individual results. Values obtained using Rheocalc V2.5 Model LV, Spindle CP40, speed 80 rpm, Shear Rate 600 1/sec, Temperature 25° C. ± 0.1

TABLE 6

Viscosity of Batches of Copaxone ® 40 mg/mL Filtered Under Reduced Temperature

| Batch No. | Average Viscosity [cPa][1] | Standard Deviation |
|---|---|---|
| 1 | 2.82 | 0.000 |
| 2 | 2.92 | 0.008 |
| 3 | 2.91 | 0.010 |
| 4 | 2.61 | 0.012 |
| 5 | 2.61 | 0.004 |
| 6 | 2.73 | 0.021 |
| 7 | 2.61 | 0.016 |
| Average | 2.743 | 0.007 |

[1]Each value is an average of 6 individual results. Values obtained using Rheocalc V2.5 Model LV, Spindle CP40, speed 80 rpm, Shear Rate 600 1/sec, Temperature 25° C. ± 0.1

The osmolality of batches of Copaxone® 20 mg/mL filtered under controlled room temperature and the osmolality of batches of Copaxone® 40 mg/mL filtered under reduced temperature were measured.

Samples from each batch were tested in triplicates. The results are reported in Table 7.

TABLE 7

Osmolality of Batches of Copaxone ® 20 mg/mL Filtered Under Controlled Room Temperature and Batches of Copaxone ® 40 mg/mL Filtered Under Reduced Temperature

| Batch No. | GA Dose | Mannitol Dose | Average Osmolality | Relative Standard Deviation (RSD) |
|---|---|---|---|---|
| Copaxone ® 40 mg/mL No. 1 | 40 mg/ml | 40 mg/ml | 303 mosmol/Kg | 1.2 |
| Copaxone ® 40 mg/mL No. 2 | 40 mg/ml | 40 mg/ml | 300[1] mosmol/Kg | 1.7 |
| Copaxone ® 40 mg/mL No. 3 | 40 mg/ml | 40 mg/ml | 302 mosmol/Kg | 2.1 |
| Copaxone ® 20 mg/mL No. 1 | 20 mg/ml | 40 mg/ml | 268 mosmol/Kg | 2.6 |
| Copaxone ® 20 mg/mL No. 2 | 20 mg/ml | 40 mg/ml | 264 mosmol/Kg | 1.2 |
| Placebo | 0 mg/ml | 40 mg/ml | 227 mosmol/Kg | 0 |

[1]Calculated from 4 measurements.

The results show that the osmolality of batches of Copaxone® 40 mg/mL were well within the ranges of an isotonic solution. The results also show that the batches of Copaxone® 40 mg/mL conformed to the general parenteral drug product osmolality limits of 300±30 mosmol/Kg. Further, the results indicate that batches of Copaxone® 20 mg/mL were slightly hypotonic.

What is claimed:

1. A process of preparing a pharmaceutical preparation of glatiramer acetate and mannitol in a suitable container comprising the steps of:
   (i) obtaining an aqueous pharmaceutical solution of glatiramer acetate and mannitol;
   (ii) filtering the aqueous pharmaceutical solution through a first filter to produce a first filtrate;
   (iii) filtering the first filtrate at a temperature of above 0° C. to 17.5° C. through a second filter to produce a second filtrate; and
   (iv) filling the suitable container with the second filtrate obtained after performing step (iii), so as to thereby prepare the pharmaceutical preparation of glatiramer acetate and mannitol in the suitable container.

2. The process of claim 1 further comprising the step of reducing the temperature of the second filter to a temperature of above 0° C. to 17.5° C.

3. The process of claim 1 further comprising the step of reducing the temperature of the aqueous pharmaceutical solution to a temperature of above 0° C. to 17.5° C. before passing through the second filter.

4. The process of claim 1 further comprising the step of receiving the first filtrate in a receiving vessel and reducing the temperature of the first filtrate to a temperature of above 0° C. to 17.5° C. after leaving the receiving vessel and before entering into the second filter.

5. The process of claim 1 further comprising the step of receiving the first filtrate in a receiving vessel and reducing the temperature of the first filtrate to a temperature of above 0° C. to 17.5° C. while in the receiving vessel.

6. The process of claim 1 further comprising the step of reducing the temperature of the first filter to a temperature of above 0° C. to 17.5° C.

7. The process of claim 1 further comprising the step of reducing the temperature of the aqueous pharmaceutical solution to a temperature of above 0° C. to 17.5° C. before passing through the first filter.

8. The process of claim 1, wherein the obtaining step (i) comprises compounding the aqueous pharmaceutical solution in a compounding vessel.

9. The process of claim 8 further comprising the step of reducing the temperature of the aqueous pharmaceutical solution to a temperature of above 0° C. to 17.5° C. after leaving the compounding vessel and before entering into the first filter.

10. The process of claim 8 further comprising the step of reducing the temperature of the aqueous pharmaceutical solution to a temperature of above 0° C. to 17.5° C. while in the compounding vessel.

11. The process of claim 1, wherein the first filtrate is passed through the second filter at a rate of 3-25 liters/hour; at a rate of 3-22 liters/hour; at a rate of 3-15 liters/hour; or at a rate of 3-10 liters/hour.

12. The process of claim 1, wherein the pressure during the filtering of step (iii) and the pressure during the filling of step (iv) is maintained below 2.0 bar.

13. The process of claim 1, wherein the temperature of the first filtrate in step (iii) is between 0° C. and 14° C., or the temperature of the first filtrate in step (iii) is reduced to a temperature between 0° C. and 14° C.

14. The process of claim 1, wherein the temperature of the first filtrate in step (iii) is between 0° C. and 12° C., or the temperature of the first filtrate in step (iii) is reduced to a temperature between 0° C. and 12° C.

15. The process of claim 1, wherein the temperature of the first filtrate in step (iii) is between 2° C. and 12° C., or the temperature of the first filtrate in step (iii) is reduced to a temperature between 2° C. and 12° C.

16. The process of claim 1, wherein the temperature of the first filtrate in step (iii) is between 4° C. and 12° C., or the temperature of the first filtrate in step (iii) is reduced to a temperature between 4° C. and 12° C.

17. The process of claim 1, wherein the filtering in step (ii), in step (iii) or both are performed using a sterilizing filter having a pore size of 0.2 μm or less.

18. The process of claim 1, wherein the pharmaceutical preparation in the suitable container is an aqueous pharmaceutical solution comprising 40 mg/ml glatiramer acetate and 40 mg/ml mannitol.

19. A process of preparing a pharmaceutical product comprising 40 mg/ml glatiramer acetate and 40 mg/ml mannitol which comprises the steps of:
(i) obtaining an aqueous pharmaceutical solution of glatiramer acetate and mannitol;
(ii) filtering the aqueous pharmaceutical solution at a temperature of above 0° C. to 17.5° C. to produce a filtrate; and
(iii) filling a suitable container with the filtrate obtained after performing step (ii), so as to thereby prepare the pharmaceutical product comprising 40 mg/ml glatiramer acetate and 40 mg/ml mannitol.

20. The process of claim 2, wherein the pharmaceutical preparation in the suitable container is an aqueous pharmaceutical solution comprising 40 mg/ml glatiramer acetate and 40 mg/ml mannitol.

21. The process of claim 3, wherein the pharmaceutical preparation in the suitable container is an aqueous pharmaceutical solution comprising 40 mg/ml glatiramer acetate and 40 mg/ml mannitol.

22. The process of claim 4, wherein the pharmaceutical preparation in the suitable container is an aqueous pharmaceutical solution comprising 40 mg/ml glatiramer acetate and 40 mg/ml mannitol.

23. The process of claim 5, wherein the pharmaceutical preparation in the suitable container is an aqueous pharmaceutical solution comprising 40 mg/ml glatiramer acetate and 40 mg/ml mannitol.

24. The process of claim 6, wherein the pharmaceutical preparation in the suitable container is an aqueous pharmaceutical solution comprising 40 mg/ml glatiramer acetate and 40 mg/ml mannitol.

25. The process of claim 7, wherein the pharmaceutical preparation in the suitable container is an aqueous pharmaceutical solution comprising 40 mg/ml glatiramer acetate and 40 mg/ml mannitol.

26. The process of claim 8, wherein the pharmaceutical preparation in the suitable container is an aqueous pharmaceutical solution comprising 40 mg/ml glatiramer acetate and 40 mg/ml mannitol.

27. The process of claim 9, wherein the pharmaceutical preparation in the suitable container is an aqueous pharmaceutical solution comprising 40 mg/ml glatiramer acetate and 40 mg/ml mannitol.

28. The process of claim 10, wherein the pharmaceutical preparation in the suitable container is an aqueous pharmaceutical solution comprising 40 mg/ml glatiramer acetate and 40 mg/ml mannitol.

29. The process of claim 11, wherein the pharmaceutical preparation in the suitable container is an aqueous pharmaceutical solution comprising 40 mg/ml glatiramer acetate and 40 mg/ml mannitol.

30. The process of claim 12, wherein the pharmaceutical preparation in the suitable container is an aqueous pharmaceutical solution comprising 40 mg/ml glatiramer acetate and 40 mg/ml mannitol.

31. The process of claim 13, wherein the pharmaceutical preparation in the suitable container is an aqueous pharmaceutical solution comprising 40 mg/ml glatiramer acetate and 40 mg/ml mannitol.

32. The process of claim 14, wherein the pharmaceutical preparation in the suitable container is an aqueous pharmaceutical solution comprising 40 mg/ml glatiramer acetate and 40 mg/ml mannitol.

33. The process of claim 15, wherein the pharmaceutical preparation in the suitable container is an aqueous pharmaceutical solution comprising 40 mg/ml glatiramer acetate and 40 mg/ml mannitol.

34. The process of claim 16, wherein the pharmaceutical preparation in the suitable container is an aqueous pharmaceutical solution comprising 40 mg/ml glatiramer acetate and 40 mg/ml mannitol.

35. The process of claim 17, wherein the pharmaceutical preparation in the suitable container is an aqueous pharmaceutical solution comprising 40 mg/ml glatiramer acetate and 40 mg/ml mannitol.

* * * * *